(12) United States Patent
Sugiyama et al.

(10) Patent No.: US 10,265,389 B2
(45) Date of Patent: Apr. 23, 2019

(54) CANCER ANTIGEN EEF2

(75) Inventors: Haruo Sugiyama, Minoo (JP); Yusuke Oji, Osaka (JP)

(73) Assignee: INTERNATIONAL INSTITUTE OF IMMUNOLOGY, INC., Osaka (JP)

( * ) Notice: Subject to any disclaimer, the term of this patent is extended or adjusted under 35 U.S.C. 154(b) by 1537 days.

(21) Appl. No.: 13/143,492

(22) PCT Filed: Jan. 8, 2010

(86) PCT No.: PCT/JP2010/050174
§ 371 (c)(1),
(2), (4) Date: Sep. 29, 2011

(87) PCT Pub. No.: WO2010/079833
PCT Pub. Date: Jul. 15, 2010

(65) Prior Publication Data
US 2012/0021994 A1 Jan. 26, 2012

(30) Foreign Application Priority Data
Jan. 8, 2009 (JP) .................................. 2009-002608

(51) Int. Cl.
| | | |
|---|---|---|
| *A61K 38/00* | (2006.01) | |
| *A61K 39/00* | (2006.01) | |
| *A61K 31/713* | (2006.01) | |
| *A61K 38/08* | (2019.01) | |
| *C07K 14/82* | (2006.01) | |
| *C12N 15/113* | (2010.01) | |
| *C12Q 1/6886* | (2018.01) | |
| *G01N 33/574* | (2006.01) | |
| *C07K 14/47* | (2006.01) | |

(52) U.S. Cl.
CPC ........ *A61K 39/0011* (2013.01); *A61K 31/713* (2013.01); *A61K 38/08* (2013.01); *C07K 14/47* (2013.01); *C07K 14/82* (2013.01); *C12N 15/113* (2013.01); *C12N 15/1135* (2013.01); *C12Q 1/6886* (2013.01); *G01N 33/57484* (2013.01); *A61K 38/00* (2013.01); *C12N 2310/11* (2013.01); *C12N 2310/14* (2013.01); *C12N 2310/531* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 7,521,195 | B1 * | 4/2009 | Joseloff et al. | 435/7.1 |
| 2002/0151681 | A1 * | 10/2002 | Rosen et al. | 530/350 |
| 2007/0184022 | A1 | 8/2007 | Wang et al. | |
| 2008/0207497 | A1 | 8/2008 | Ramakrihna et al. | |
| 2008/0286312 | A1 | 11/2008 | Gross et al. | |
| 2009/0232768 | A1 | 9/2009 | Wang et al. | |

FOREIGN PATENT DOCUMENTS

| | | |
|---|---|---|
| EP | 1 536 009 A1 | 6/2005 |
| EP | 1 548 032 A1 | 6/2005 |
| WO | WO 02/094981 A2 | 11/2002 |
| WO | WO 2005/011730 A1 | 2/2005 |
| WO | WO 2008/041231 A2 | 4/2008 |
| WO | 2008/109833 * | 9/2008 |

OTHER PUBLICATIONS

Engelhard, Current Opinion in Immunology vol. 6 p. 13 (1994).*
Guo, et al Nature vol. 360 p. 384 (1992).*
Rammensee et al, Immunogenetics vol. 41 p. 178 (1995).*
Shastri et al J. Immunol. vol. 1995 vol. 155 p. 4339.*
Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
Ezzell (J. NIH Res. 1995 7:46).*
Spitler (Cancer Biotherapy, 1995, 10:1-3).*
Boon (Adv. Can. Res. 1992 58:177-210).*
Bocchia et al Lancet vol. 365 p. 657 (2005).*
Oka et al PNAS vol. 101 p. 13885 (2004).*
Takahashi et al Eur. J. Cancer vol. 49 p. 852 (2013).*
Nishida et al J Immunother vol. 37 p. 105 (2014.*
Haigh et al Oncology vol. 13 p. 1561 (1999).*
Robert-Tissot et al, Expert Review of Vaccines vol. 12 p. 1325 (2013).*
Craig et al Cancer Journal, vol. 17 p. 343 (2011).*
Brinckerhoff, L. H. et al., "Melanoma Vaccines," *Current Opinion in Oncology*, Current Science LTD, 2000, vol. 12, No. 2, pp. 163-173.
Novellino, L. et al., "A listing of human tumor antigens recognized by T cells: Mar. 2004 update," *Cancer Immunology, Immunotherapy*, 2005, vol. 54, No. 3, pp. 187-207.
Partial European Search Report for EP Application No. 13188341.5, dated Mar. 3, 2014, (8 pages).
Li, Lan et al., "Identification of Hepatocellular-Carcinoma-Associated Antigens and Autoantibodies by Serological Proteome Analysis Combined With Protein Microarray," Journal of Proteome Research, vol. 7, No. 2, Feb. 1, 2008, pp. 611-620.

(Continued)

*Primary Examiner* — Sheela J. Huff
(74) *Attorney, Agent, or Firm* — Finnegan, Henderson, Farabow, Garrett & Dunner LLP

(57) ABSTRACT

The present invention provides a method for detecting cancer using a protein expressed in various cancers, and a pharmaceutical composition for the treatment or prevention of such cancer using the protein as an indicator. Furthermore, the present invention provides a pharmaceutical composition containing a cancer antigen peptide derived from the protein. More particularly, the method comprises the step of determining the presence or amount of an eEF2 polypeptide or an eEF2 antibody in a sample obtained from a subject.

5 Claims, 13 Drawing Sheets
Specification includes a Sequence Listing.

(56) References Cited

OTHER PUBLICATIONS

Fernández-Madrid, Felix et al., "Autobodies to Annexin XI-A and Other Autoantigens in the Diagnosis of Breast Cancer," Cancer Research, vol. 64, No. 15, Aug. 1, 2004, pp. 5089-5096.

Pogue-Geile, Kay et al., "A New Microarray, Enriched in Pancreas and Pancreatic Cancer cDNAs to Identify Genes Relevant to Pancreatic Cancer," Cancer Genomics & Proteomics, vol. 1, Jan. 1, 2004, pp. 371-386.

Suehara, Yoshiyuki et al., "Proteomic Signatures Corresponding to Historical Classification and Grading of Soft-Tissue Sarcomas," Proteomics, vol. 6, No. 15, Aug. 1, 2006, pp. 1814-1836.

Suehara, Yoshiyuki et al., "Proteomic Signatures Corresponding to Historical Classification and Grading of Soft-Tissue Sarcomas," Proteomics, vol. 6, No. 15, Aug. 1, 2006, pp. 4402-4409.

Wolf, Philipp et al., "Anti-PSMA Immunotoxin as Novel Treatment for Prostate Cancer? High and Specific Antitumor Activity on Human Prostrate Xenograft Tumors in SCID, Mice," The Prostrate, vol. 68, No. 2, Feb. 1, 2008, pp. 129-138.

Wüllner, Ulrich, "Cell-Surface Receptor Specific Delivery of Short Interfering RNAs Via Bivalent Aptamer-siRNA Transcripts or Covalent Antibody-siRNA Conjugates," Aachen, Jan. 1, 2008, pp. 1-121.

Extended European Search Report for EP Application No. 10729253.4 dated Mar. 13, 2013.

Office Action for corresponding JP Patent Application No. 2010-545797 dated May 27, 2014.

International Search Report dated Mar. 30, 2010 issued in corresponding International Application No. PCT/JP2010/050174.

International Preliminary Report on Patentability dated Aug. 25, 2011 issued in corresponding International Application No. PCT/JP2010/050174.

K. T. Hogan et al., "The Peptide Recognized by HLA-A68.2-restricted, Squamous Cell Carcinoma of the Lung-specific Cytotoxic T Lymphocytes Is Derived from a Mutated Elongation Factor 2 Gene," Cancer Research, 1998, vol. 58, pp. 5144-5150.

Mian Zhou et al., Analysis of responsible genes for progression in CML by cDNA-RDA, International Journal of Hematology, 2001, vol. 73, Supplement No. 1, p. 121.

Ulrich Wullner et al., "Cell-Specific Induction of Apoptosis by Rationally Designed Bivalent Aptamer-siRNA Transcripts Silencing Eukaryotic Elongation Factor 2," Current Cancer Drug Targets, 2008, vol. 8, No. 7, pp. 554-565.

Junya Nakamura et al., "Overexpression of eukaryotic elongation factor eEF2 in gastrointestinal cancers and its involvement in G2/M progression in the cell cycle," International Journal of Oncology, 2009, vol. 34, pp. 1181-1189.

Odd Nygård et al., "Kinetic Determination of the Effects of ADP-ribosylation on the Interaction of Eukaryotic Elongation Factor 2 with Ribosomes," The Journal of Biological Chemistry, 1990, vol. 265, No. 11, pp. 6030-6034.

Hawkins, Oriana E. et al., "Identification of Breast Cancer Peptide Epitopes Presented by HLA-A*0201," Journal of Proteorne Research, Apr. 1, 2008, vol. 7, No. 4, pp. 1445-1457.

Hunt, D. F. et al., "Characterization of Peptides Bound to the Class I MHC Molecule HLA-A2.1 by Mass Spectrometry," Science, Mar. 6, 1992, vol. 255, pp. 1261-1263.

Ramakrishna, Venkatesh et al., "Naturally Occurring Peptides Associated With HLA-A2 in Ovarian Cancer Cell Lines Identified by Mass Spectrometry are Targets of HLA-A2-Restricted Cytotoxic T Cells," International Immunology, Jun. 1, 2003, vol. 15, No. 6, pp. 751-763.

Zhu, Bo et al., "Identification of HLA-A*0201-Restricted Cytotoxic T Lymphocyte Epitope from TRAG-3 Antigen," Clinical Cancer Research, May 1, 2003, vol. 9, No. 5, pp. 1850-1857.

Extended European Search Report dated Jun. 2, 2014 issued in corresponding European Patent Application No. 13188341.5.

Summons to attend oral proceedings pursuant to Rule 115(1) EPC for corresponding EP Application No. 13188341.5 dated May 23, 2016.

\* cited by examiner

[Fig 1.]
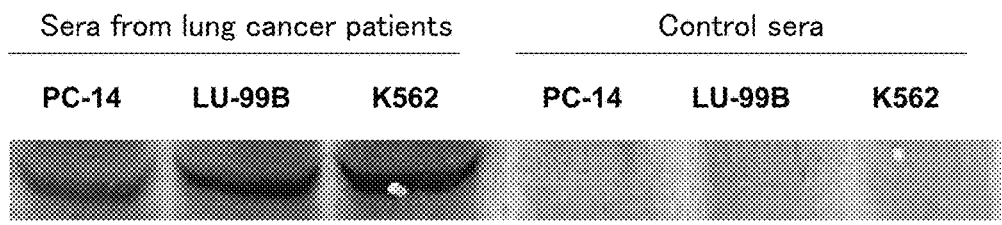
[Fig 2.]
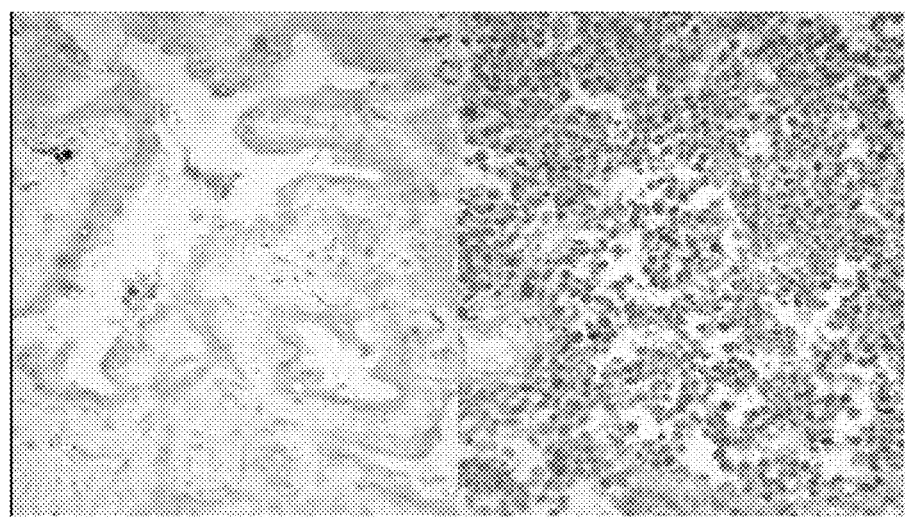
[Fig 3.]
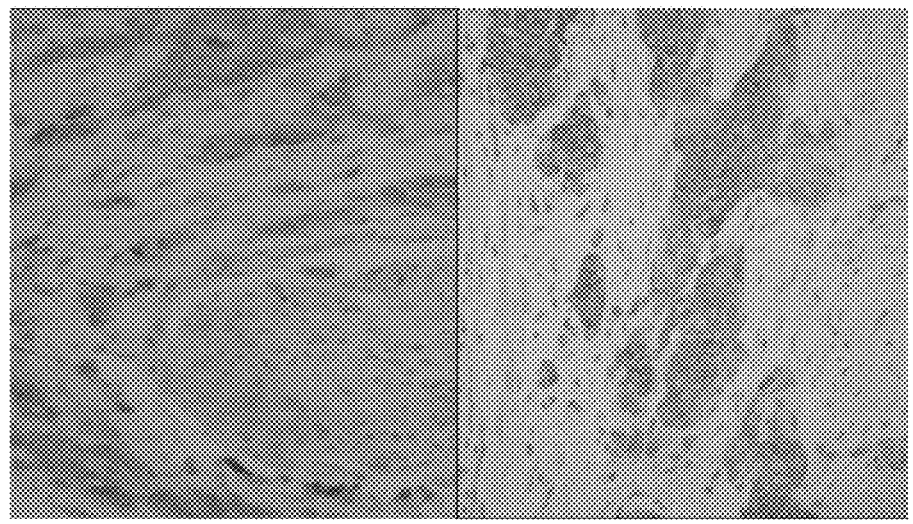

[Fig 4.]
[Fig 5.]
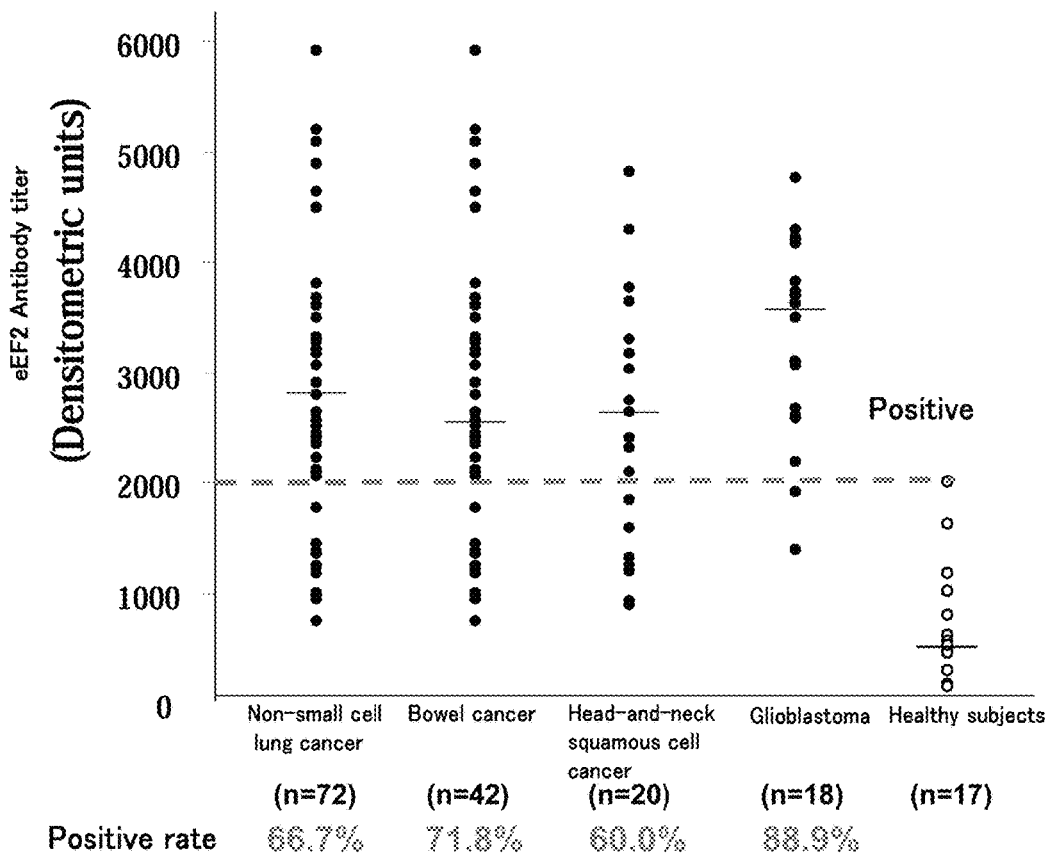

[Fig 6.]
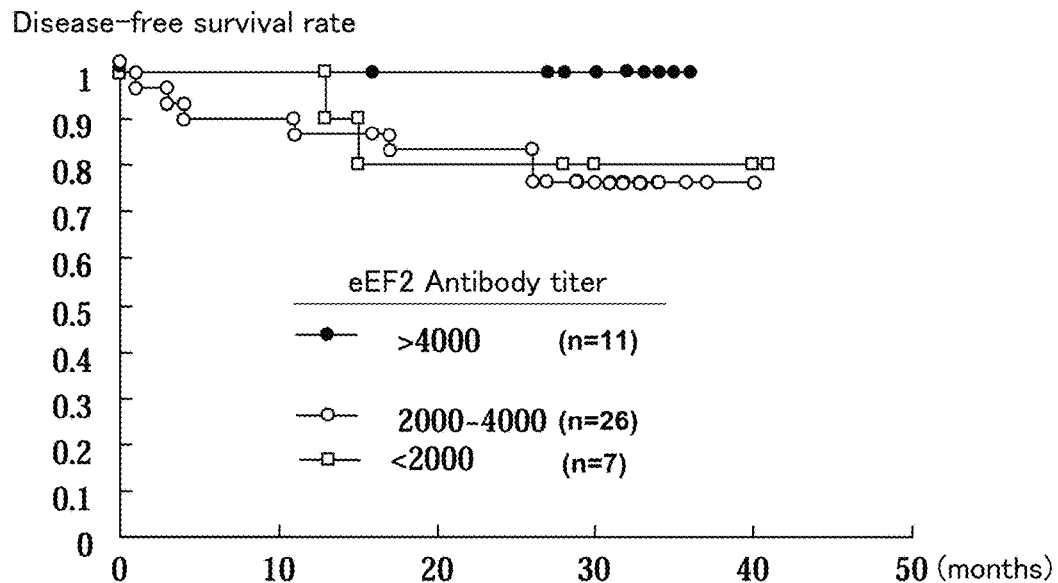
[Fig 7.]
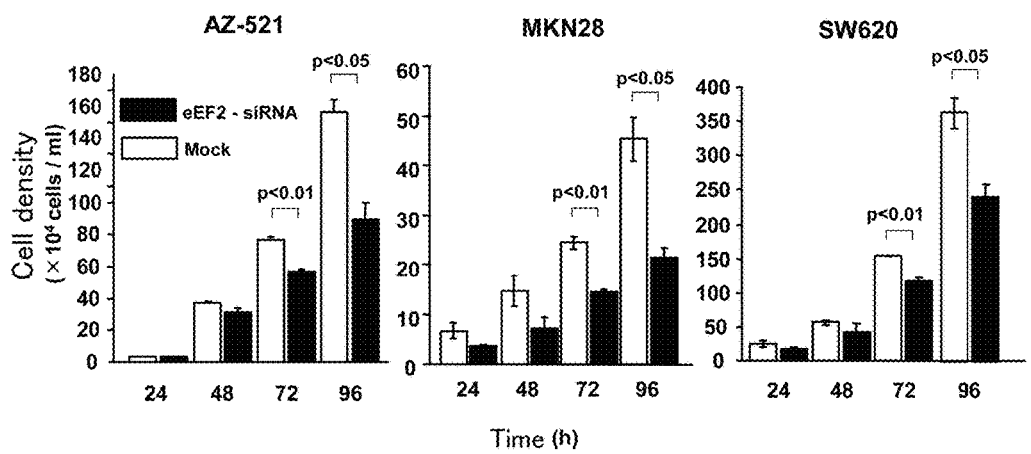

[Fig 8.]
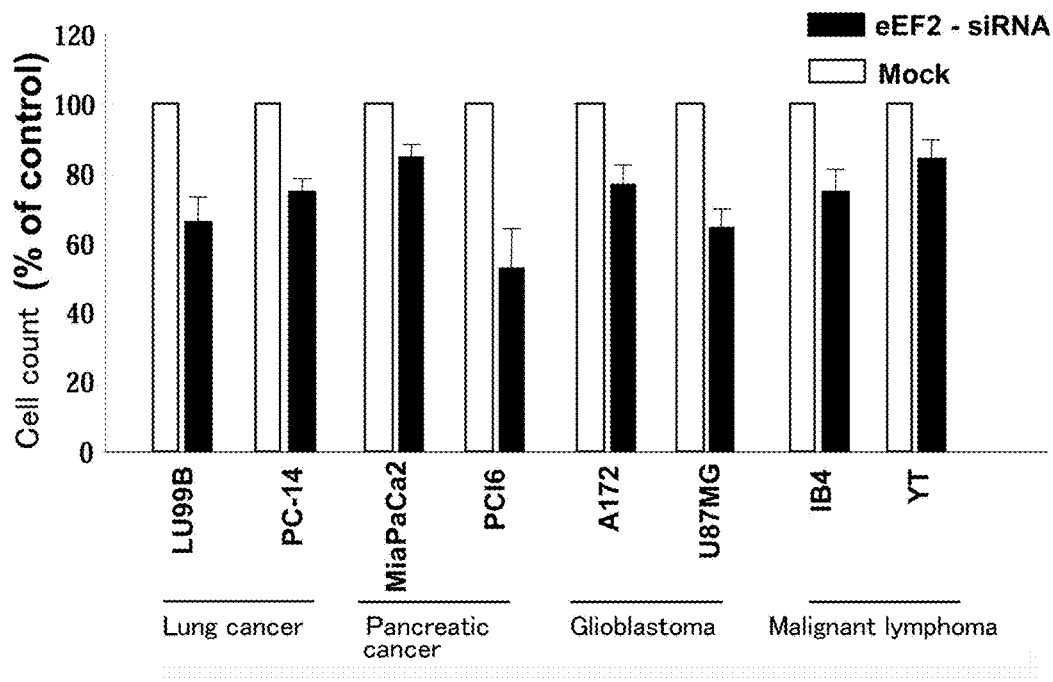
[Fig 9.]
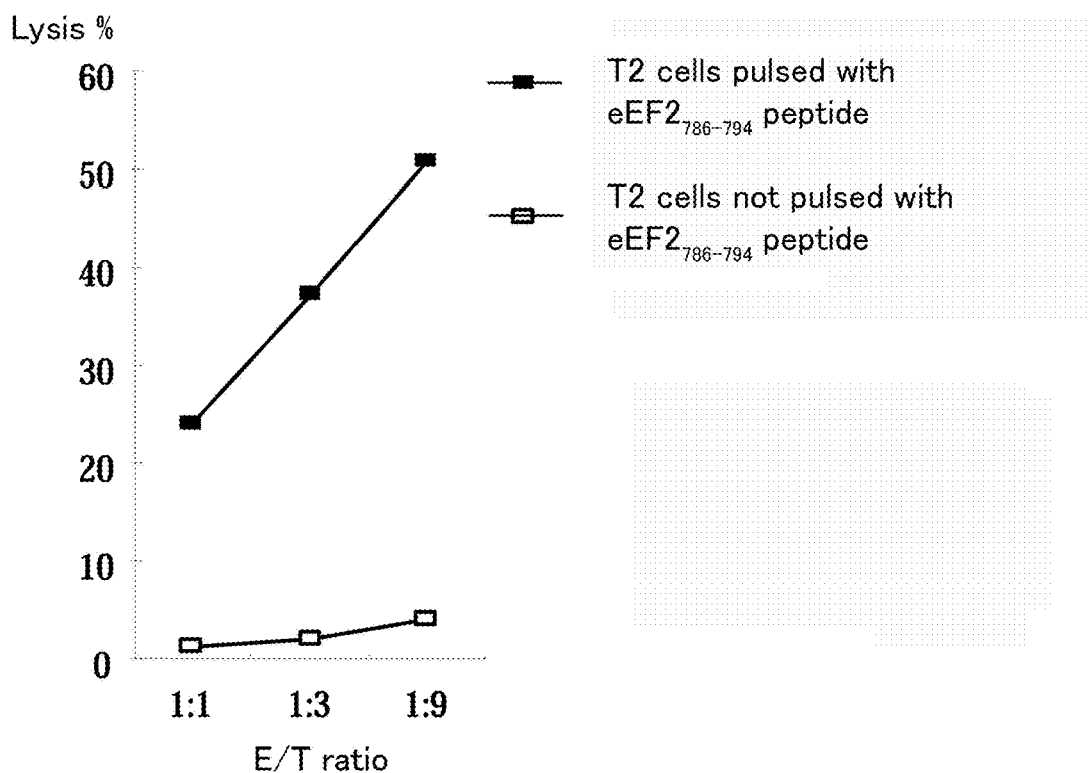

[Fig 10.]
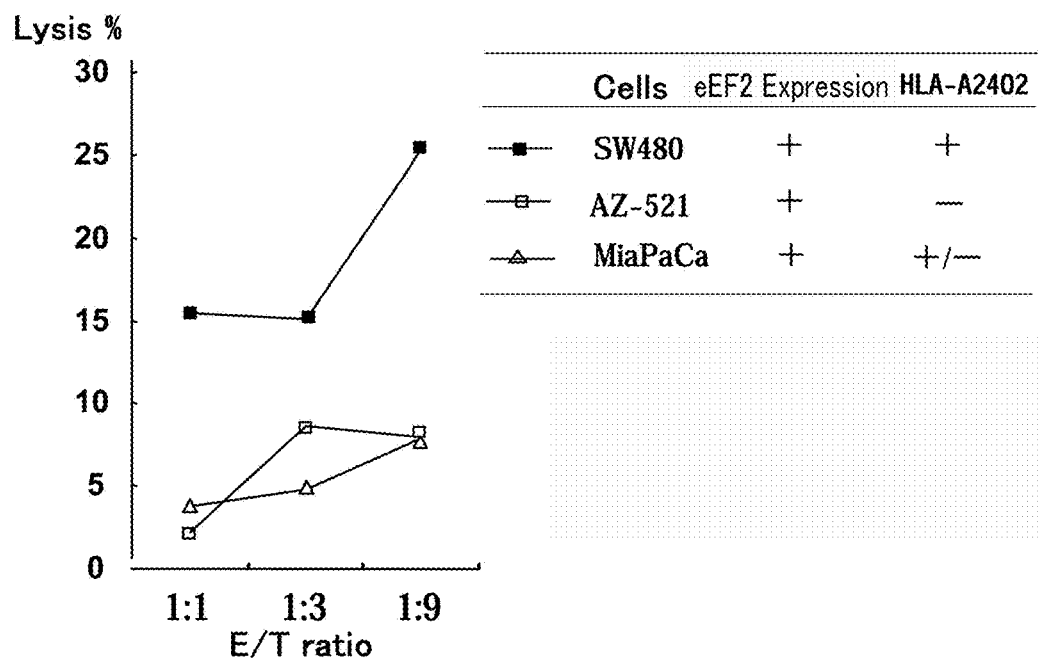
[Fig 11.]
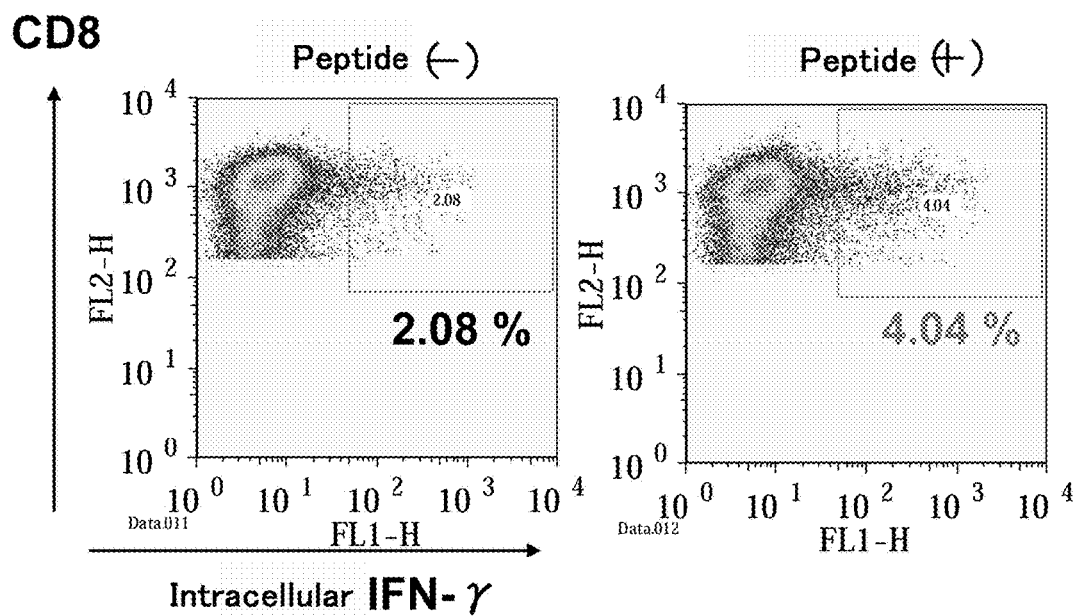

[Fig 12.]
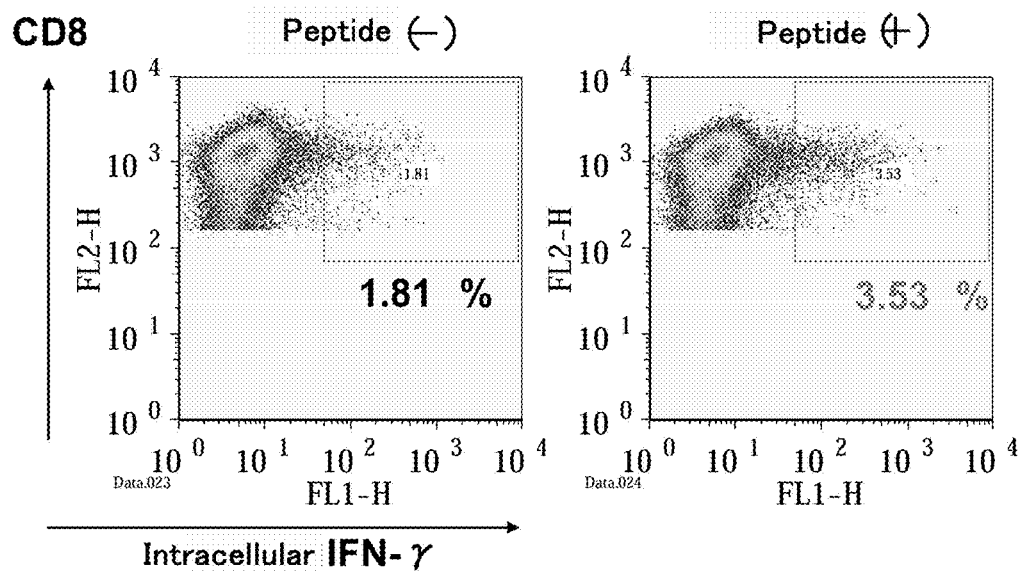
[Fig 13.]
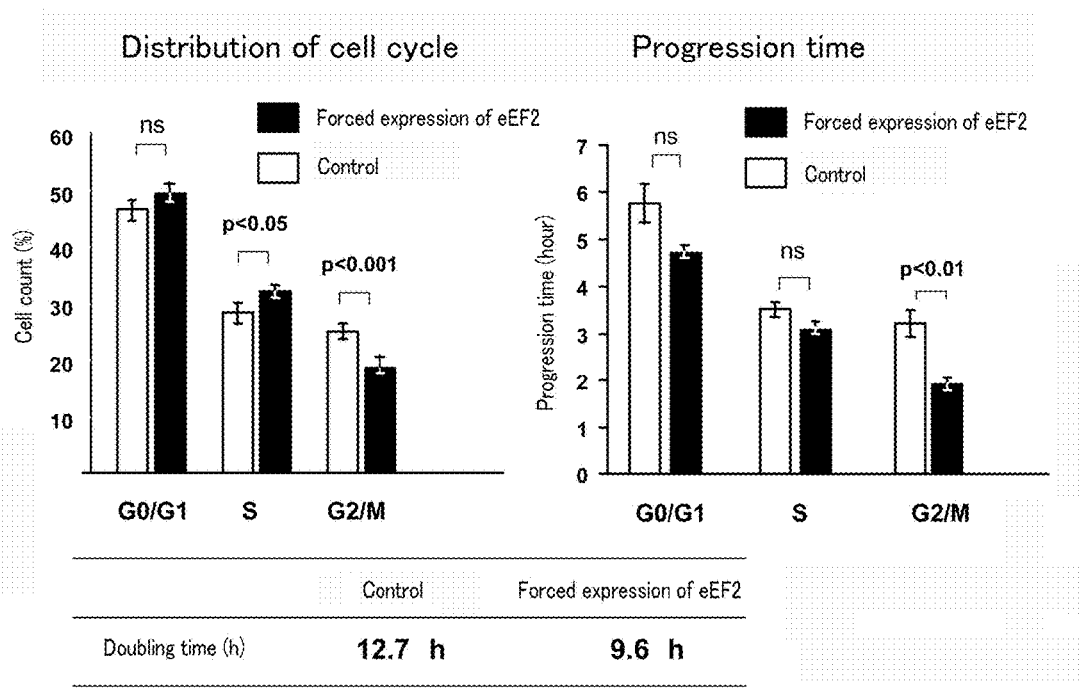

[Fig 14.]
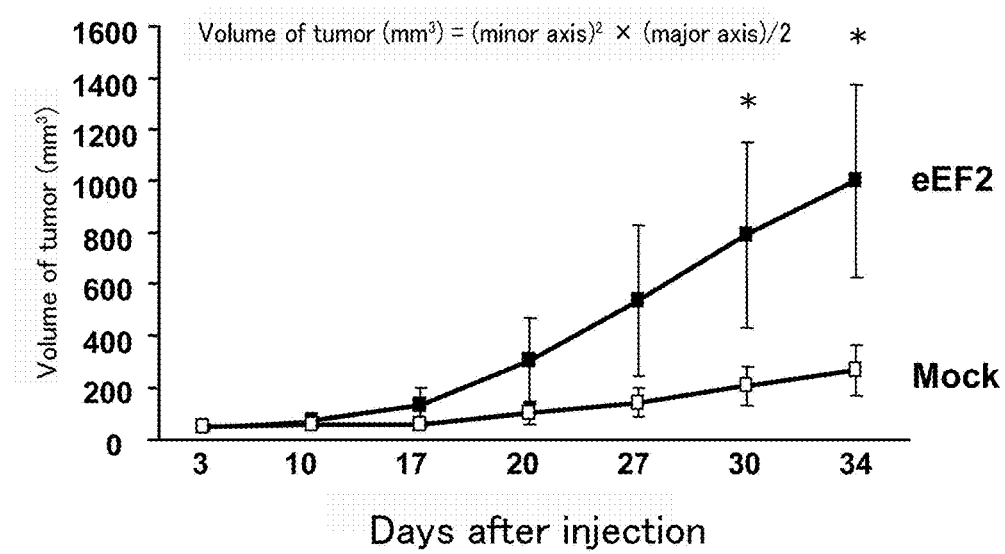
[Fig 15.]
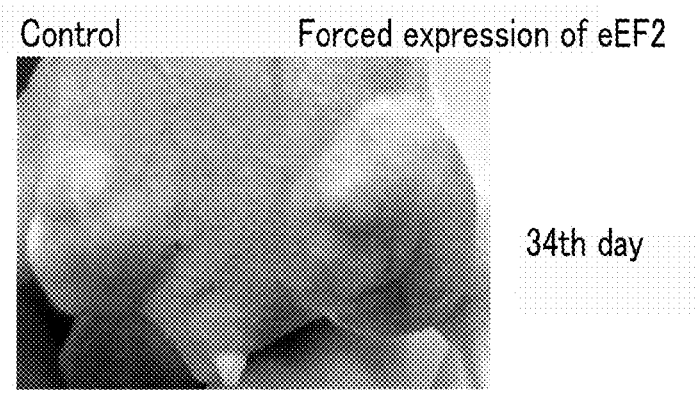

[Fig 16.]
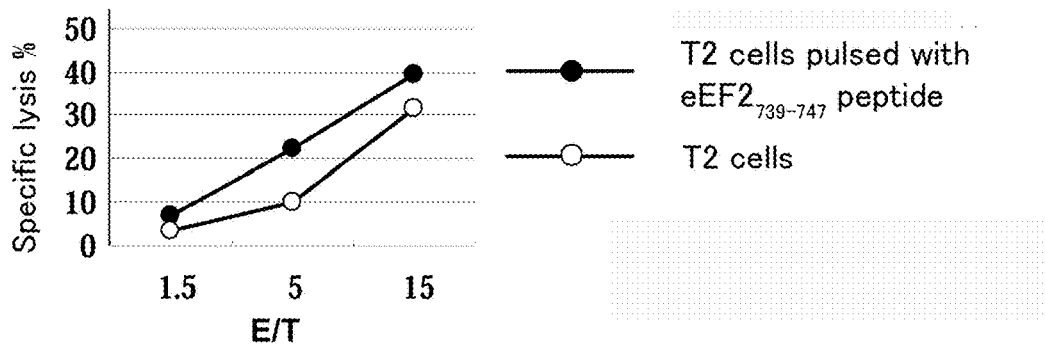
[Fig 17.]
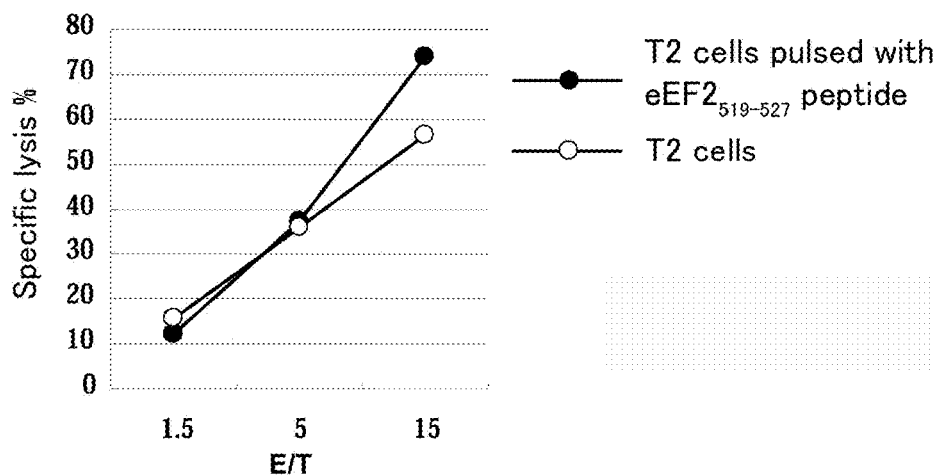
[Fig 18.]
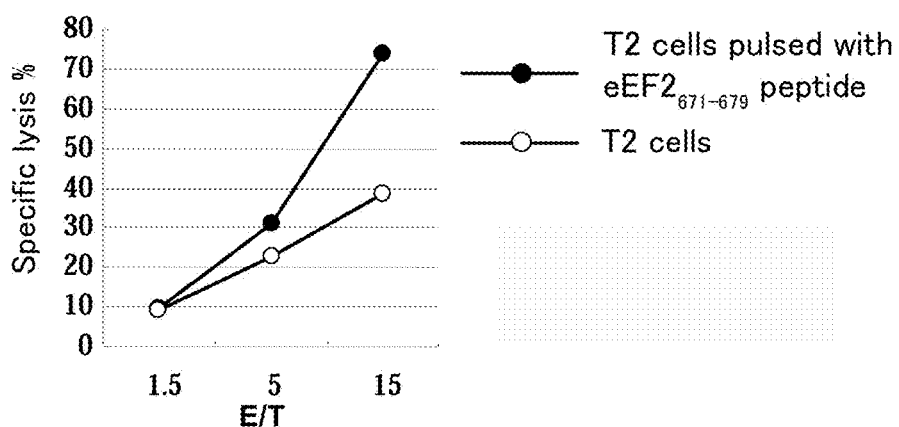

[Fig 19.]
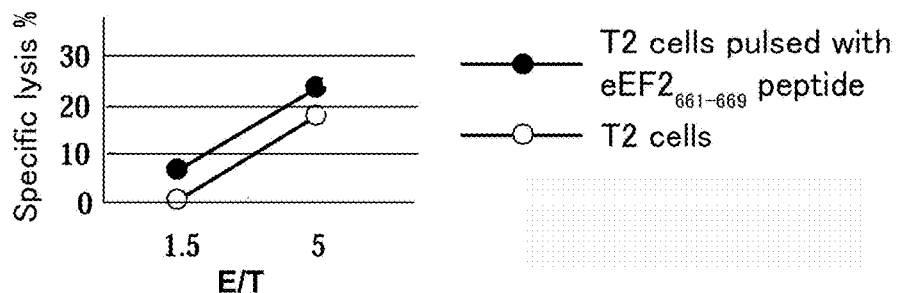
[Fig 20.]
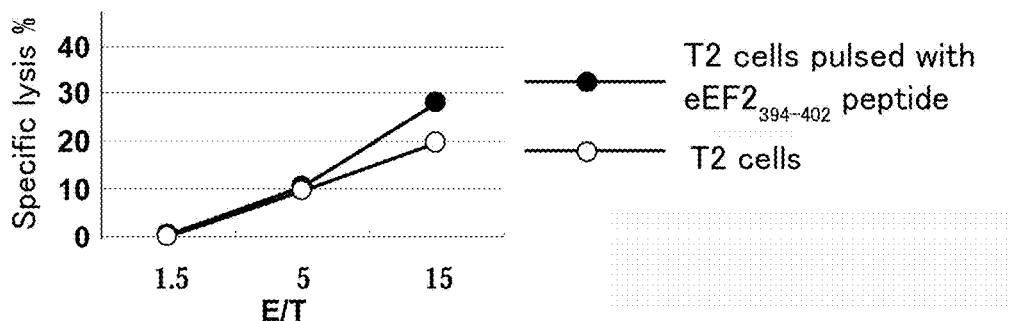
[Fig 21.]
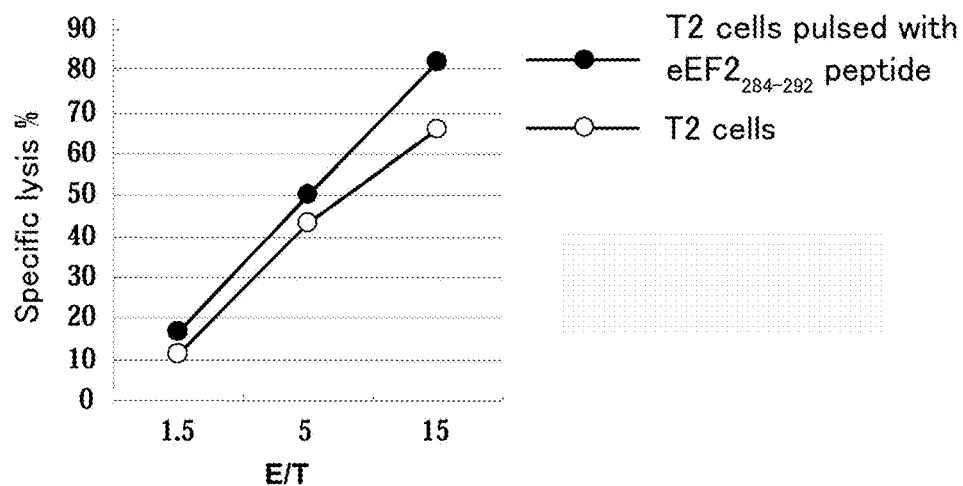

[Fig 22.]
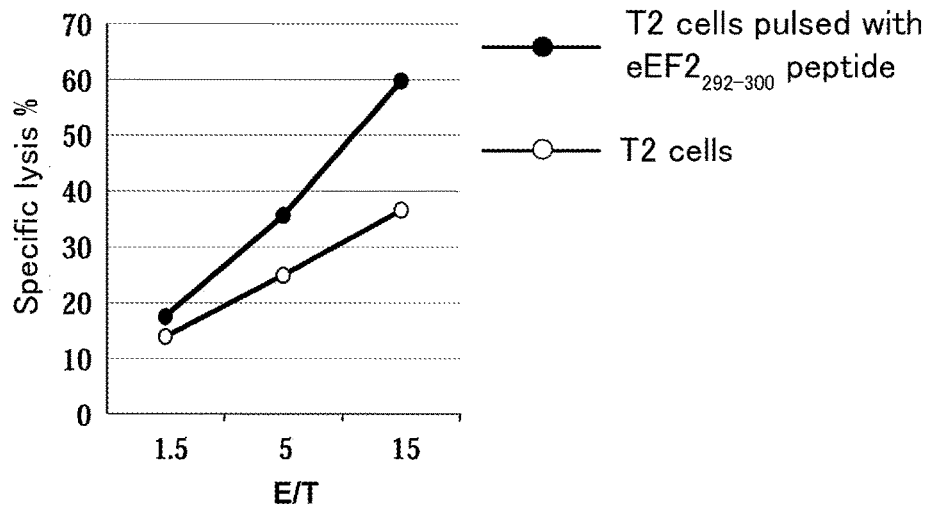
[Fig 23.]
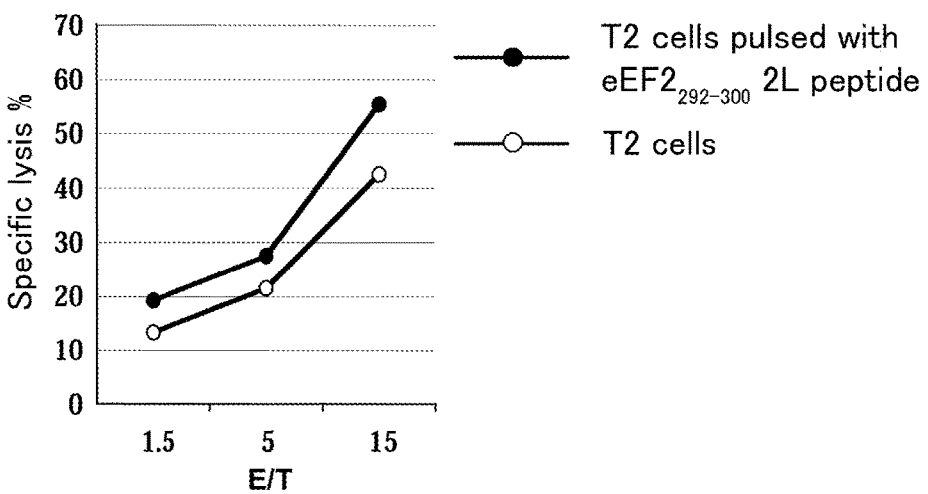

[Fig 24.]
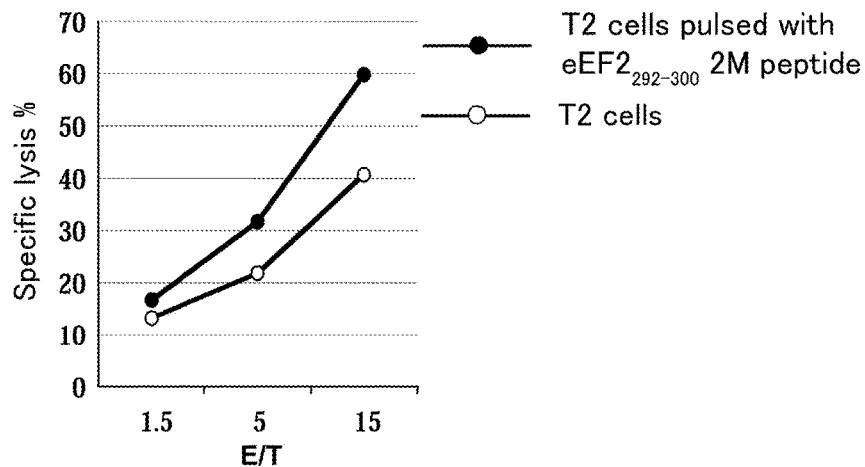
[Fig 25.]
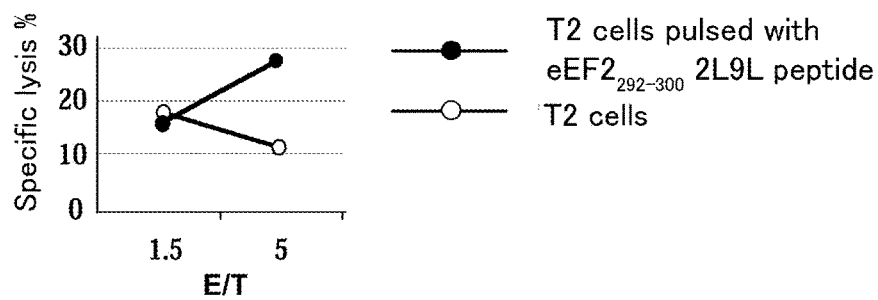
[Fig 26.]
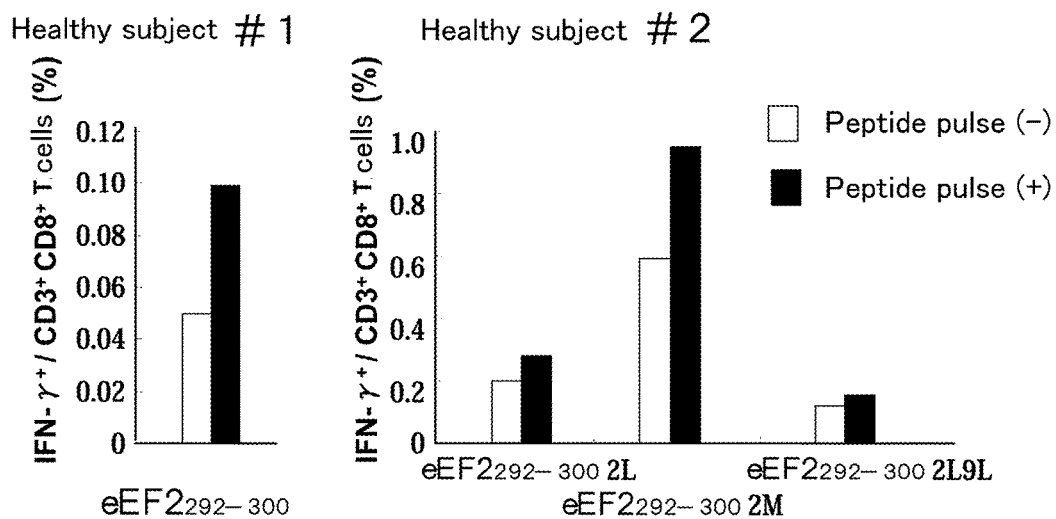

[Fig 27.]
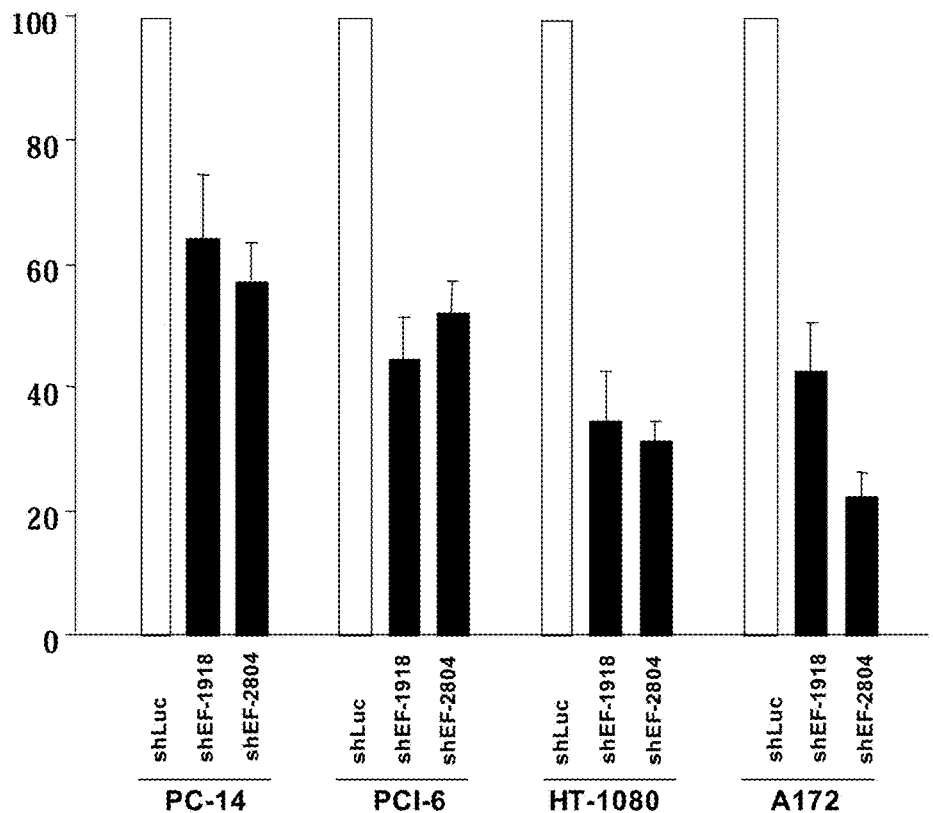
[Fig 28.]
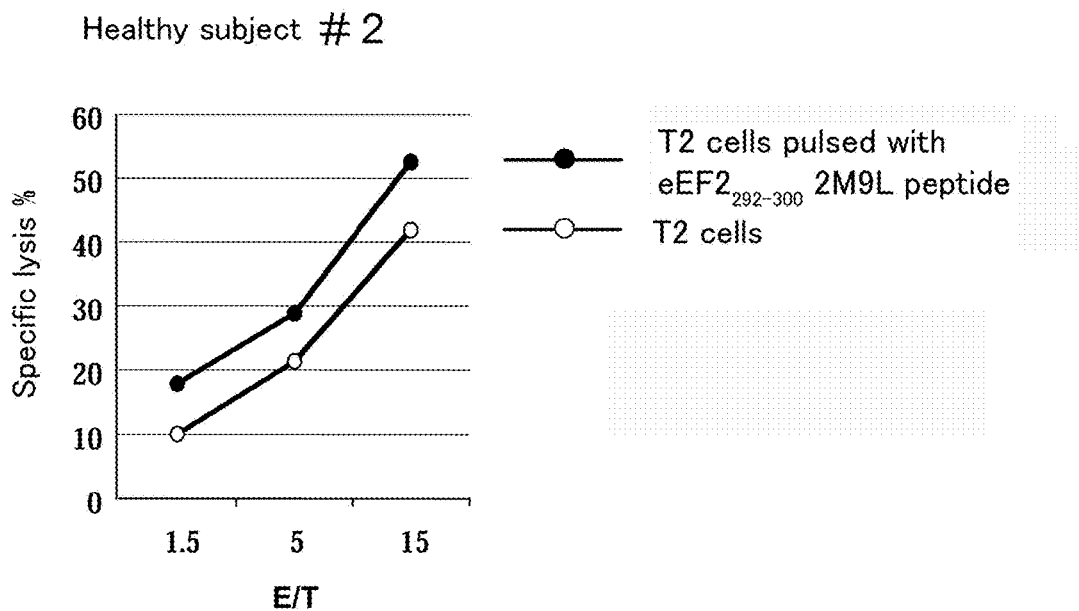

[Fig 29.]
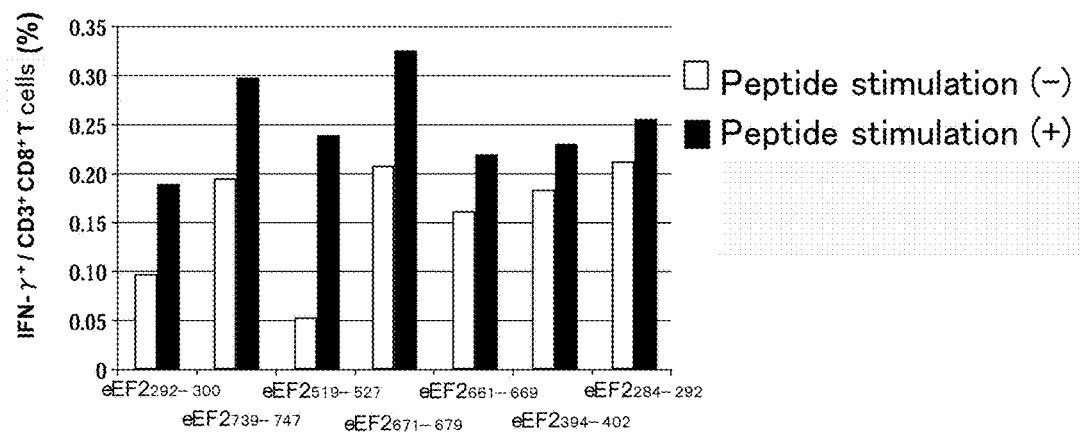
[Fig 30.]
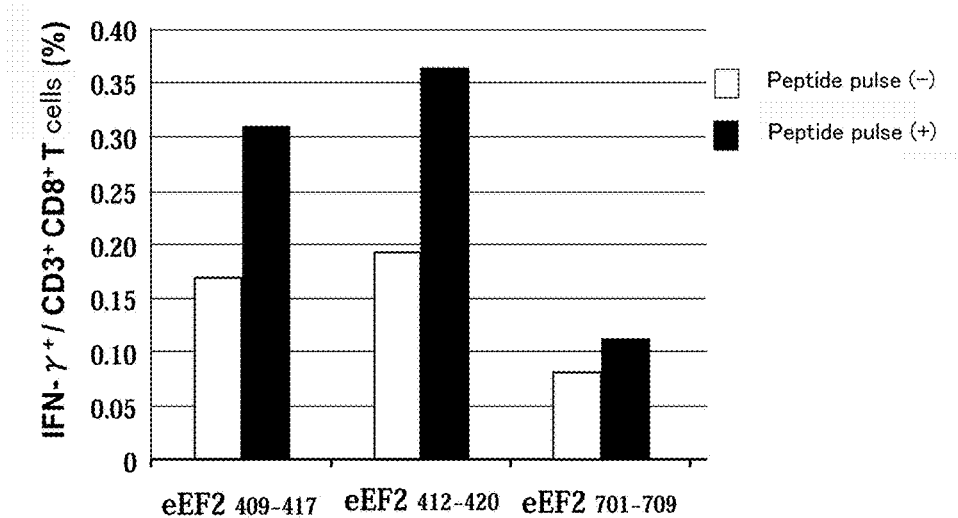

CANCER ANTIGEN EEF2

TECHNICAL FIELD

The present invention provides a method for detecting cancer and a pharmaceutical composition for the treatment and prevention of such cancer. Furthermore, the present invention provides a peptide containing contiguous amino acids derived from an eEF2 protein having a binding ability to an HLA molecule, and a pharmaceutical composition for the treatment and prevention of cancer, which contains such a peptide, particularly, an HLA-A*2402-restricted eEF2 peptide, an HLA-A*0201-restricted eEF2 peptide, or an HLA-A*0206-restricted eEF2 peptide, and a pharmaceutical composition for the treatment and prevention of cancer, which contains such a peptide, and others. The present application claims priority to Japanese Patent Application No. 2009-002608, the whole disclosure of which is incorporated herein by reference.

BACKGROUND ART

Various cancer markers have hitherto been known. However, there are few cancer markers which can diagnose various cancers using one marker, and such cancer markers are intently searched. On the other hand, molecularly-targeted drugs against cancer such as trastuzumab targeting at HER2, imatinib targeting at one of tyrosine kinases, gefitinib targeting at EGFR, and rituximab targeting at a CD20 antigen are now developed continuously, but even now there is no pharmaceutical composition for the treatment and prevention of cancer, which targets at eEF2 known as a translation elongation factor (eukaryotic translation elongation factor 2) (Non-Patent Document 1). Also, search of antigenic proteins is carried out with respect to various cancers, but only a few proteins are proved to be a cancer antigen.

Non-Patent Document 1: Nygard O, Nilsson L., "Kinetic determination of the effects of ADP-ribosylation on the interaction of eukaryotic elongation factor 2 with ribosomes", J Biol. Chem. 1990; 265:6030-4

DISCLOSURE OF THE INVENTION

Problems to be Solved by the Invention

Thus, an object to be achieved by the present invention is to provide a method for detecting cancer using a protein expressed in various cancers as an indicator, and a pharmaceutical composition for the treatment or prevention of such cancer detected by the method. Another object of the present invention is to provide a pharmaceutical composition containing a cancer antigen peptide derived from such a protein.

Means for Solving the Problems

The present inventors have devoted themselves to much research so as to achieve the above objects. As a result, the present inventors have found one marker protein eEF2 which is highly expressed in various cancer tissues, and accomplished a method for detecting cancer using, as an indicator, expression of the marker protein and an antibody produced in the body against the marker protein and a pharmaceutical composition for the treatment and prevention of such cancer which targets at the eEF2 protein. Also, the present inventors have found that a part of a contiguous amino acid sequence encoding the eEF2 protein functions as a cancer antigen peptide, and proved that such a part can be used in a pharmaceutical composition for the treatment and prevention of such cancer.

Thus, the present invention provides:
(1) A method for detecting cancer in a subject, which comrises the step of determining the presence or amount of an eEF2 polypeptide, an eEF2 antibody or a transcript of an eEF2 gene in a sample obtained from the subject;
(2) The method according to (1), wherein the cancer is selected from the group consisting of lung adenocarcinoma, non-small cell lung cancer, small-cell lung cancer, head-and-neck squamous cell cancer, esophageal cancer, esophageal squamous cell cancer, stomach cancer, colon cancer, pancreatic duct cancer, glioblastoma, and malignant lymphoma;
(3) A double-stranded siRNA inhibiting cancer cell proliferation, wherein the sense strand consists of the RNA sequence shown in SEQ ID NO:2 and the antisense strand consists of the RNA sequence shown in SEQ ID NO:3;
(4) The double-stranded siRNA according to (3), wherein the cancer cell is derived from cancer selected from the group consisting of stomach cancer, lung cancer, pancreatic cancer, glioblastoma and malignant lymphoma;
(5) A pharmaceutical composition for the treatment or prevention of cancer, comprising the double-stranded siRNA according to (3) or (4) as an active ingredient;
(6) A method for the treatment or prevention of cancer, which comprises administering an effective amount of the pharmaceutical composition according to (5) to a subject;
(7) Use of the double-stranded siRNA according to (3) or (4) for the production of a pharmaceutical for the treatment or prevention of cancer;
(8) An shRNA inhibiting cancer cell proliferation, which targets at an mRNA transcribed from the DNA sequence shown in SEQ ID NO:18 or 19;
(9) A nucleic acid from which the shRNA according to (8) is transcribed, which has the DNA sequence shown in SEQ ID NO:20 or 22;
(10) A vector comprising the nucleic acid according to (9);
(11) A pharmaceutical composition for the treatment or prevention of cancer, which comprises the shRNA according to (8), the nucleic acid according to (9) or the vector according to (10);
(12) A method for the treatment or prevention of cancer, which comprises administering an effective amount of the pharmaceutical composition according to (11) to a subject;
(13) Use of the shRNA according to (8), the nucleic acid according to (9) or the vector according to (10) for the production of a pharmaceutical for the treatment or prevention of cancer;
(14) A pharmaceutical composition for the treatment or prevention of cancer in an HLA-A*2402-positive subject, comprising an eEF2 peptide having an amino acid sequence composed of contiguous amino acids derived from an eEF2 protein, wherein the amino acid sequence is selected from the group consisting of:
(a) Arg Phe Tyr Ala Phe Gly Arg Val Phe (SEQ ID NO:4);
(b) Ala Phe Gly Arg Val Phe Ser Gly Leu (SEQ ID NO:5);
(c) Arg Phe Asp Val H is Asp Val Thr Leu (SEQ ID NO:6);
(d) Ala Tyr Leu Pro Val Asn Glu Ser Phe (SEQ ID NO:7); and
(e) an amino acid sequence having substitution, deletion or addition of one or several amino acids in the amino acid sequences as shown in (a) to (d);
(15) The pharmaceutical composition according to (14), wherein the amino acid sequence is Ala Tyr Leu Pro Val Asn Glu Ser Phe (SEQ ID NO:7);

(16) A pharmaceutical composition for the treatment or prevention of cancer in a subject, comprising a polynucleotide encoding the peptide according to (14);
(17) The pharmaceutical composition according to any one of (14) to (16), wherein the cancer is selected from the group consisting of lung adenocarcinoma, small-cell lung cancer, esophageal cancer, stomach cancer, colon cancer, pancreatic duct cancer, malignant glioblastoma, malignant lymphoma and head-and-neck squamous cell cancer;
(18) A method for the treatment or prevention of cancer, which comprises administering an effective amount of the pharmaceutical composition according to any one of (14) to (17) to an HLA-A*2402-positive subject;
(19) Use of the peptide according to (14) for the production of a pharmaceutical for the treatment or prevention of cancer;
(20) A pharmaceutical composition for the treatment or prevention of cancer in an HLA-A*0201-positive subject, comprising an eEF2 peptide having an amino acid sequence composed of contiguous amino acids derived from an eEF2 protein, wherein the amino acid sequence is selected from the group consisting of:
(a) Arg Leu Met Glu Pro Ile Tyr Leu Val (SEQ ID NO:8);
(b) Lys Leu Val Glu Gly Leu Lys Arg Leu (SEQ ID NO:9);
(c) Tyr Leu Asn Glu Ile Lys Asp Ser Val (SEQ ID NO:10);
(d) Ile Leu Thr Asp Ile Thr Lys Gly Val (SEQ ID NO:11);
(e) Leu Met Met Tyr Ile Ser Lys Met Val (SEQ ID NO:12);
(f) Lys Leu Pro Arg Thr Phe Cys Gln Leu (SEQ ID NO:13);
(g) Leu Ile Leu Asp Pro Ile Phe Lys Val (SEQ ID NO:14); and
(h) an amino acid sequence having substitution, deletion or addition of one or several amino acids in the amino acid sequences as shown in (a) to (g);
(21) The pharmaceutical composition according to (20), wherein the amino acid sequence is Arg Leu Met Glu Pro Ile Tyr Leu Val (SEQ ID NO:8) or Ile Leu Thr Asp Ile Thr Lys Gly Val (SEQ ID NO:11);
(22) The pharmaceutical composition according to (20), wherein the amino acid sequence has, in the Leu Ile Leu Asp Pro Ile Phe Lys Val (SEQ ID NO:14), a substitution of the amino acid Ile at position 2 with Leu or Met, and/or a substitution of the amino acid Val at position 9 with Leu;
(23) A pharmaceutical composition for the treatment or prevention of cancer in a subject, comprising a polynucleotide encoding the peptide according to (20);
(24) The pharmaceutical composition according to any one of (20) to (23), wherein the cancer is selected from the group consisting of lung adenocarcinoma, small-cell lung cancer, esophageal cancer, stomach cancer, colon cancer, pancreatic duct cancer, malignant glioblastoma, malignant lymphoma and head-and-neck squamous cell cancer;
(25) A method for the treatment or prevention of cancer, which comprises administering an effective amount of the pharmaceutical composition according to any one of (20) to (24) to a subject; and
(26) Use of the peptide according to (20) for the production of a pharmaceutical for the treatment or prevention of cancer.

Effects of the Invention

According to the present invention, it is possible to detect, in a subject having cancer, or a possibility of cancer, or a prognosis of cancer, various cancers, for example, lung adenocarcinoma, non-small cell lung cancer, small-cell lung cancer, head-and-neck squamous cell cancer, esophageal cancer, esophageal squamous cell cancer, stomach cancer, colon cancer, pancreatic duct cancer, glioblastoma, malignant lymphoma and the like in a high sensitivity. Also, it is possible to inhibit proliferation of cancer cells detected by the above method. Furthermore, the present invention provides an HLA-A*2402-restricted eEF2 peptide or an HLA-A*0201-restricted eEF2 peptide, a pharmaceutical composition for the treatment and prevention of cancer, which comprises such a peptide, and others.

Accordingly, it is possible to induce eEF2-specific CTL in vivo and in vitro in a subject having HLA-A*2402 or HLA-A*0201. In particular, since about 55% of Japanese have at least one HLA-A*2402 molecule, and about 19.9% have at least one HLA-A*0201 molecule, it is possible to induce the eEF2-specific CTL in a very wide range of subjects.

BRIEF DESCRIPTION OF THE DRAWINGS

FIG. 1 shows that an eEF2 IgG antibody was detected in sera from lung cancer patients.
FIG. 2 shows the results of immunostaining with an anti-eEF2 antibody in lung tissue sections obtained from patients having non-small cell lung cancer (left) and small-cell lung cancer (right).
FIG. 3 shows the results of immunostaining with an anti-eEF2 antibody in tissue sections of head-and-neck squamous epithelium and esophageal squamous epithelium obtained from patients having head-and-neck squamous cell cancer (left) and esophageal squamous cell cancer (right).
FIG. 4 shows the results of immunostaining with an anti-eEF2 antibody in stomach and large colon tissue sections obtained from patients having stomach cancer (left) and colon cancer (right).
FIG. 5 shows the detection of an eEF2 antibody in sera obtained from patients having various types of cancers and healthy subjects.
FIG. 6 shows that, in patients having non-small cell lung cancer, subjects indicating a high eEF2 antibody titer in sera have a good prognosis.
FIG. 7 shows that the double-stranded siRNA targeting at an mRNA of an eEF2 gene inhibits proliferation of stomach cancer cell lines.
FIG. 8 shows that the double-stranded siRNA targeting at an mRNA of an eEF2 gene inhibits cell proliferation of various cancer cell lines.
FIG. 9 shows the cytotoxic activity of CTL induced using an $eEF2_{786-794}$ peptide.
FIG. 10 shows the cytotoxic activity of CTL induced using an $eEF2_{786-794}$ peptide against endogenous eEF2 gene-expressing cells.
FIG. 11 is a graph showing the results obtained by analyzing interferon-γ induced using an $eEF2_{739-747}$ peptide by FACS.
FIG. 12 is a graph showing the results obtained by analyzing interferon-γ induced using an $eEF2_{661-669}$ peptide by FACS.
FIG. 13 is a graph showing that forced expression of an eEF2 protein accelerates progression of G2/M phase in a cell cycle.
FIG. 14 is a graph showing that forced expression of an eEF2 protein accelerates tumorigenesis in vivo.
FIG. 15 is a graph showing that forced expression of an eEF2 protein accelerates tumorigenesis in vivo.
FIG. 16 is a graph showing a cytotoxic activity of CTL induced using an $eEF2_{739-747}$ peptide.
FIG. 17 is a graph showing a cytotoxic activity of CTL induced using an $eEF2_{519-527}$ peptide.

FIG. 18 is a graph showing a cytotoxic activity of CTL induced using an eEF2$_{671-679}$ peptide.

FIG. 19 is a graph showing a cytotoxic activity of CTL induced using an eEF2$_{661-669}$ peptide.

FIG. 20 is a graph showing a cytotoxic activity of CTL induced using an eEF2$_{394-402}$ peptide.

FIG. 21 is a graph showing a cytotoxic activity of CTL induced using an eEF2$_{284-292}$ peptide.

FIG. 22 is a graph showing a cytotoxic activity of CTL induced using an eEF2$_{292-300}$ peptide.

FIG. 23 is a graph showing a cytotoxic activity of CTL induced using an eEF2$_{292-300}$ 2L peptide.

FIG. 24 is a graph showing a cytotoxic activity of CTL induced using an eEF2$_{292-300}$ 2M peptide.

FIG. 25 is a graph showing a cytotoxic activity of CTL induced using an eEF2$_{292-300}$ 2L9L peptide.

FIG. 26 is a graph showing the results obtained by measuring the interferon-γ activity when pulsed with an eEF2$_{292-300}$ peptide or modified-type eEF2$_{292-300}$ peptides (eEF2$_{292-300}$ 2L, eEF2$_{292-300}$ 2M, and eEF2$_{292-300}$ 2L9L peptide).

FIG. 27 is a graph showing inhibition of cancer cell proliferation by novel shRNAs of eEF2 in vitro. The cell count is shown using percentage (%) of the count of cells into which vectors expressing shRNA of eEF2 are introduced, relative to the count of cells into which control vector shLuc is introduced.

FIG. 28 is a graph showing the results obtained by measuring the interferon-γ activity when pulsed with a modified-type eEF2$_{292-300}$ peptide (eEF2$_{292-300}$ 2M9L peptide).

FIG. 29 is a graph showing the results of interferon-γ activity measurement indicating that seven eEF2 peptides (eEF2$_{292-300}$ peptide, eEF2$_{739-747}$ peptide, eEF2$_{519-527}$ peptide, eEF2$_{671-679}$ peptide, eEF2$_{661-669}$ peptide, eEF2$_{394-402}$ peptide, and eEF2$_{284-292}$ peptide) also serve as an HLA-A*0206-restricted peptide.

FIG. 30 is a graph showing the results obtained by measuring the interferon-γ activity when pulsed with three eEF2 peptides (eEF2$_{409-417}$ peptide, eEF2$_{412-420}$ peptide, and eEF2$_{701-709}$ peptide).

BEST MODE FOR CARRYING OUT THE INVENTION

In an aspect, the present invention provides a method for detecting cancer. Subjects in which cancer can be detected using the method of the present invention may be any animals such as, for example, human, monkey, mouse, rat, hamster, guinea pig, bovine, horse, sheep, goat, pig, dog, cat, and rabbit, and most preferably human. Although the present method can be used even if subject animals are healthy, it is preferably used in subjects having cancer or a possibility of cancer. Also, the present method can be used in prognosis of cancer treatment in subjects. Characteristics of the present invention reside in the fact that it can detect cancer in early stage as compared with CEA used as a conventional cancer marker. For example, the method of the present invention can detect non-small cell lung cancer in early stage, particularly in stage I, in a high sensitivity. In this connection, the stage I refers to a stage representing a tumor state classified into T1 or T2, N0 and M0 in the TNM classification defined by the Union for International Cancer Control which is disease stage classification of malignant tumors.

The present invention can be practiced using samples obtained from the above subjects. The samples used in the present invention may be any samples, and it is possible to use tissues containing cells, for example. The samples used in the present invention are preferably various types of tissue sections or sera. The samples can be acquired from subjects using techniques conventional to those skilled in the art. In case tissue sections are used as the samples used in the present invention, for example, tissues obtained by surgery or biopsy may be fixed overnight in 10% formalin, and then embedded in paraffin to prepare thin-sliced sections. On the other hand, in case sera are used as the samples used in the present invention, peripheral blood of subjects may be coagulated in a test tube containing a separating agent, and then, sera may be acquired by centrifugation.

Cancers which can be detected by the method of the present invention include any cancers expressing an eEF2 protein, and are preferably lung adenocarcinoma, non-small cell lung cancer, small-cell lung cancer, head-and-neck squamous cell cancer, esophageal cancer, esophageal squamous cell cancer, stomach cancer, colon cancer, pancreatic duct cancer, glioblastoma, and malignant lymphoma. In particular, lung adenocarcinoma, small-cell lung cancer, stomach cancer, colon cancer, and malignant lymphoma are preferably detected. Cancers detected in the present invention may be those in any stages. For example, cancers in any stage of stage I, stage II and stage III in the TNM classification defined by the above International Union Against Cancer may be detected. A cancer which can be detected by the method of the present invention particularly early stage is non-small cell lung cancer.

When the detection method of the present invention is practiced in a subject, the presence or amount of an eEF2 polypeptide can be determined in the above samples. The eEF2 polypeptide in the present invention means a polypeptide having an amino acid sequence of an eEF2 protein or a partial sequence thereof, and includes the following variants. Thus, the eEF2 polypeptide in the present invention may have the amino acid sequence of a human eEF2 protein shown in SEQ ID NO:1; or may have an amino acid sequence having deletion, substitution or addition of one or several amino acids in the amino acid sequence shown in SEQ ID NO:1, or an amino acid sequence having deletion, substitution, addition and/or insertion of one or multiple amino acids in the amino acid sequence shown in SEQ ID NO:1, for example, an amino acid sequence having deletion, substitution or addition of 1 to 9, preferably 1 to 5, 1 to 4, 1 to 3, more preferably 1 to 2 amino acids, and still more preferably one amino acid, or an amino acid sequence having deletion, substitution, addition and/or insertion of 1 to 9, preferably 1 to 5, 1 to 4, 1 to 3, more preferably 1 to 2 amino acids, and still more preferably one amino acid; or an amino acid sequence having a homology of 70% or more, preferably a homology of 80% or more, more preferably a homology of 90% or more, and still more preferably a homology of 93%, 95%, or 99% or more as compared with the amino acid sequence shown in SEQ ID NO:1; or an amino acid sequence of a fragment of any one of the above amino acid sequences. The homology of an amino acid sequence can be determined using a conventional sequence analyzing tool such as FASTA and BLAST. The fragment in the present invention refers to a portion of the above eEF2 polypeptides. Also, the eEF2 polypeptide in the present invention includes polypeptides which have properties comparable to those of the eEF2 protein and which have an amino acid sequence encoded by a nucleotide sequence hybridizing with a nucleotide sequence encoding the amino acid sequence shown in SEQ ID NO:1 under a stringent condition. The comparable properties in the present specification refer to biologically, chemically and physically comparable properties as compared with the eEF2 protein. The eEF2 protein in the present invention is derived from human. Even if, however, the eEF2 protein is derived from other animals such as, for example, mouse, monkey, rat, bovine and cat, the eEF2 protein in these animals is included in the eEF2 protein in the present specification.

In the present invention, the conditions of the above hybridization can be selected suitably by those skilled in the art according to the description of J. Sambrook et al., "Molecular Cloning: A Laboratory Manual, Second Edition", 1989, Cold Spring Harbor Laboratory Press. Although the conditions of the hybridization may be a low stringent condition, a high stringent condition is preferable. The low stringent condition is, for example, a condition of 42° C., 0.1×SSC and 0.1% SDS, preferably a condition of 50° C., 0.1×SSC and 0.1% SDS, in a washing step after hybridization in accord with the above reference. The high stringent condition includes, for example, a condition of 65° C., 5×SSC and 0.1% SDS, etc. However, those skilled in the art can realize similar conditions by suitably selecting the above elements.

The detection method of the present invention may be carried out by any methods. For example, the detection method of the present invention can be carried out using an antibody against the above eEF2 polypeptide. An antibody against a polypeptide having an amino acid sequence in an arbitrary region of the above eEF2 polypeptide may be used in the detection method of the present invention. For example, an antibody against a polypeptide having a region of positions 1-417 or positions 411-858 in the amino acid sequence of the human eEF2 protein may be used. The antibody used in the present invention may be any isotype of IgG, IgA, IgM, IgD and IgE. Also, the antibody used in the present invention may be a monoclonal antibody or a polyclonal antibody. The antibody used in the present invention may be prepared using a conventional technique, or may be a marketed product.

Also, the detection method of the present invention can be carried out using an antibody against an eEF2 antibody. The eEF2 antibody which can be detected in the present invention is one produced in vivo, i.e., in the body of a subject. In the detection method of the present invention, an antibody against the above eEF2 antibody can be prepared by a known technique, or may be a marketed product. Preferably, an anti-eEF2 antibody (H-118, Santa Cruz Biotechnology, Santa Cruz, Calif.) may be used.

In order to determine the presence or amount of an eEF2 polypeptide or an eEF2 antibody in a sample, known means and methods can be used in the present invention. Any means and methods may be used so far as they can detect qualitatively or quantitatively an eEF2 polypeptide or an eEF2 antibody. For example, they include immunological detection methods for a protein such as immunostaining, dot blotting, fluorescence antibody technique, complement-binding reaction, neutralizing antibody measurement, immunoprecipitation, western blotting, radioimmunoassay (RIA), ELISA, and two-hybrid system. Preferably, immunostaining or dot blotting may be used in the present invention.

"Positive" evaluation can be determined in the detection method of the present invention by comparing the presence or amount of an eEF2 polypeptide or an eEF2 antibody in a sample obtained from a subject with the presence or amount of the eEF2 polypeptide or eEF2 antibody in a sample obtained from a healthy subject or a subject in a normal phase. In case a serum is used as a sample in the detection method of the present invention, an antibody titer (densitometric units) of an eEF2 antibody in the serum may be used as an indicator. In this case, an antibody titer of an eEF2 antibody in a serum of a subject is measured by dot blotting, and a numerical value higher than that in a serum from a healthy subject, preferably 1,000 or more, more preferably 2,000 or more of an antibody titer (densitometric units) may be determined as "positive". However, the numerical value can vary depending on various factors such as cancer types and tissues, and can be set suitably by those skilled in the art. On the other hand, in case a tissue section is used as a sample, a degree of stain by immunostaining in the tissue section may be used as a criterion. In this case, for example, the presence of cancer cells showing intense stain as compared with corresponding normal cells in an amount of 25% or more of total cancer cells may be determined as "positive". However, the determination may be made suitably by those skilled in the art.

When the detection method of the present invention is practiced in a subject, the presence or amount of a transcript of an eEF2 gene can be determined in a sample. The transcript of an eEF2 gene in the present invention means a product transcribed from a nucleotide sequence encoding an amino acid sequence of the above eEF2 polypeptide or a fragment thereof, and may be, for example, mRNAs or any other types of RNAs as well as their fragments, etc. Also, the presence or amount of a polynucleotide having a nucleotide sequence (for example, DNA sequence) encoding an amino acid sequence of an eEF2 polypeptide or a fragment thereof can be determined in the detection method of the present invention.

In order to determine the presence or amount of the above transcript or polynucleotide in a sample, means and methods conventional to those skilled in the art as a method for detecting a polynucleotide may be used in the present invention. For example, they include methods for detecting a polynucleotide such as in situ hybridization, northern blotting, southern blotting, dot blotting, RNase protection assay, PCR, RT-PCR, and real-time PCR. Also, it may be possible to carry out a gene analyzing method using a microarray (for example, DNA microarray, microRNA microarray, protein microarray, etc.). Furthermore, other methods may be used so far as they can detect the above transcript or polynucleotide qualitatively or quantitatively.

Furthermore, the method of the present invention can be used for diagnosis of prognosis of a subject having cancer. Cancers to which the method of the present invention can be applied may be any cancers expressing an eEF2 protein as described above, and they are preferably lung adenocarcinoma, non-small cell lung cancer, small-cell lung cancer, head-and-neck squamous cell cancer, esophageal cancer, esophageal squamous cell cancer, stomach cancer, colon cancer, pancreatic duct cancer, glioblastoma, malignant lymphoma, and more preferably non-small cell cancer. In the diagnosis of prognosis in the present invention, the higher the value of an antibody titer of an eEF2 antibody in a sample obtained from a subject, the better the prognosis. For example, the antibody titer (densitometric units) of the eEF2 antibody is a value of 1,000 or more, preferably 2,000 or more, and more preferably 4,000 or more, and those skilled in the art can suitably determine the value taking various factors into account.

In another aspect, the present invention relates to a diagnosis kit for detecting cancer, which comprises, as an essential constituent, an antibody against the above eEF2 polypeptide or eEF2 antibody, or a polynucleotide probe complementary to the above transcript of eEF2 gene or a portion thereof. In the present invention, the above antibody or probe is preferably labeled. The above labeling can be carried out by a conventional method. The kit of the present invention contains, for example, a reagent essential to a method for detecting a protein or a polynucleotide, a sampling means, a reaction vessel and the like, in addition to the antibody against the above eEF polypeptide or eEF2 antibody, or the polynucleotide probe complementary to the above transcript of eEF2 gene or a portion thereof. In general, the kit is accompanied with an instruction manual. The kit of the present invention can be used to detect efficiently cancer expressing an eEF2 protein in a serum or a tissue.

In another aspect, the present invention relates to a double-stranded siRNA which inhibits cancer cell proliferation. Cancer cells of which proliferation can be inhibited by the present invention may be any cancers expressing an eEF2 protein, and are preferably lung adenocarcinoma, non-small cell lung cancer, small-cell lung cancer, head-and-neck squamous cell cancer, esophageal cancer, esophageal squamous cell cancer, stomach cancer, colon cancer, pancreatic duct cancer, glioblastoma, and malignant lymphoma. In particular, lung adenocarcinoma, small-cell lung cancer, stomach cancer, colon cancer, and malignant lymphoma are preferably inhibited.

The siRNA of the present invention is a double-stranded siRNA containing a sense strand and an antisense strand targeting at a nucleotide sequence of an mRNA transcribed from a human eEF2 gene. The nucleotide sequence targeted by the siRNA of the present invention may be a partial sequence of a nucleotide sequence encoding the amino acid sequence shown in SEQ ID NO:1. The siRNA of the present invention is preferably a double-stranded siRNA consisting of the sense strand (SEQ ID NO:2) and the antisense strand (SEQ ID NO:3) having the RNA sequences as shown below:

Sense strand of siRNA of the present invention (SEQ ID NO:2);

5'-CAUGGGCAACAUCAUGAUCGAUCCUGUCCU-3'

Antisense strand of siRNA of the present invention (SEQ ID NO:3);

5'-AGGACAGGAUCGAUCAUGAUGUUGCCCAUG-3'.

Although preferred RNA sequences of the siRNA of the present invention are the above sequences shown in SEQ ID NOs:2 and 3, these sequences may have addition, deletion or substitution of one, two or three bases. Also, these sequences may have substitution, deletion, addition and/or insertion of 1 to 3, preferably 1 or 2 bases, and more preferably one base. The hybridization condition in this case is a condition in a living body in case the siRNA of the present invention is used by administering in a living body, and a moderately stringent condition or a high stringent condition in case the siRNA of the present invention is used in vitro as a reagent. Such a condition includes, for example, a hybridization condition of 400 mM NaCl, 40 mM PIPES pH6.4, 1 mM EDTA, at 50° C. to 70° C. for 12 to 16 hours. Also, the sense strand sequence of the siRNA of the present invention has a sequence homology of 90%, or more, preferably 95% or more, and more preferably 95, 96, 97, 98, or 99% or more to a target sequence.

Also, the siRNA of the present invention may have addition of an overhang sequence at 5' end or 3' end. In this connection, the overhang sequence refers to a protruding sequence added to either 5' end or 3' end of a double-stranded sequence consisting of paired sense and antisense strands in order to increase a stability of the double-stranded siRNA. The overhang sequence includes, for example, a sequence such as AG, UA, AUG, UUG and AAGCUU from 5' side, and any sequences can be used. In the double-stranded siRNA of the present invention, UU is preferably added to the 3' end of sense and antisense strands. Also, the above double-stranded siRNA of the present invention may form an shRNA by linking two siRNAs through a loop sequence.

The double-stranded siRNA of the present invention can be prepared by a method conventional to those skilled in the art. For example, it may be synthesized in vitro chemically or enzymatically, or synthesized in vivo, but the method is not limited thereto. A chemically synthesizing method is preferably used. After each strand is synthesized by such a synthetic method, the strands can be paired under a conventional pairing condition. When used, the strands may be purified suitably as needed. Also, the double-stranded siRNA of the present invention may be prepared in the form of a siRNA expression vector expressing the above RNA sequences of the siRNA (SEQ ID NO:2 and SEQ ID NO:3). In this case, for example, tRNA-shRNA expression vector, piGENE tRNA Pur (Clontech, Palo Alto, Calif.) may be used for the preparation. There is no particular limitation on the length of the siRNA used in the present invention, and 15 to 50 mer siRNA can be exemplified as an example of a preferred siRNA of the present invention, 20 to 40 mer siRNA as a more preferred example, and 25 to 35 mer (for example, 30 mer) siRNA as further preferred example. Thus, a double-stranded siRNA which can hybridize with the sequence: 5'-CAUGGGCAACAUCAUGAUCGAUCCU-GUCCU-3' (SEQ ID NO:2) of the eEF2 mRNA and which is 15 to 50 mer, preferably 20 to 40 mer, more preferably 25 to 35 mer (for example, 30 mer) in length of each siRNA can be exemplified as an example of a preferred siRNA of the present invention.

In general, it is known that a siRNA binds to an mRNA of a target gene in cells into which the siRNA is introduced and inhibits expression of the mRNA. Accordingly, the double-stranded siRNA of the present invention has a function of inhibiting expression of an eEF2 gene, thereby being able to inhibit cell proliferation in a subject into which the siRNA is introduced. Methods for introducing or administering the siRNA in the present invention may be those known to those skilled in the art such as a calcium phosphate method using a transfection reagent, a liposome method, anon-liposome method, electroporation, and a magnetic particle method. Alternatively, a method may be adopted in which the siRNA is integrated into a conventional siRNA expression vector and the vector is introduced by a known method as described above. Preferably, a siRNA expression vector expressing the above RNA sequences of the siRNA (SEQ ID NO:2 and SEQ ID NO:3) is introduced by a known method. Also, the siRNA of the present invention may be administered in the form of a pharmaceutical composition as described below.

The present invention provides a pharmaceutical composition for the treatment or prevention of cancer, comprising the above double-stranded siRNA as an active ingredient. The pharmaceutical composition of the present invention may contain a known anticancer drug as an active ingredient, in addition to the above double-stranded siRNA.

The pharmaceutical composition of the present invention may contain a siRNA as an active ingredient in the form of a vector into which the siRNA is integrated. For example, the siRNA may be contained in the form of one cloned into a known siRNA expression vector such as a commercially available siRNA expression vector or a known siRNA expression vector suitably recombined according to an aspect used. Accordingly, the present invention provides a nucleic acid encoding the siRNA of the present invention, and a vector containing the nucleic acid.

The pharmaceutical composition of the present invention may contain a pharmaceutically acceptable carrier. The pharmaceutically acceptable carrier which can be used in the present invention may be one or more components selected from the group consisting of a physiological saline, distilled water, Ringer's solution, a buffered physiological saline, a dextrose solution, a maltodextrose solution, glycerol, ethanol and a liposome, but is not limited thereto. Also, other conventional additives such as an antioxidant, a buffered aqueous solution, and a bacteriostatic agent may be added to the pharmaceutical composition of the present invention. Furthermore, diluents, sprays, surfactants, binders and lubricants may be added to the composition in order to produce an injection solution, pills, capsules, granules or tablets.

The dosage form of the pharmaceutical composition of the present invention may be oral administration or parenteral administration (for example, intravenous administration, intradermal administration, subcutaneous administration, intramuscular administration, transnasal administration or oral administration), and other dosage forms may also be used so far as they can deliver an active ingredient efficiently to an affected part or its neighborhood. The effective amount of the siRNA of the present invention administered through the pharmaceutical composition of the present invention can be determined depending on conditions of subjects such as, for example, weight, age, sex and health state of subjects, as well as amount of food, frequency of administration, method of administration, amount of excretion, seriousness of disease and the like. The effective amount of the siRNA of the present invention administered through the pharmaceutical composition of the present invention is usually from 0.01 to 100 mg/kg per day, and preferably from 0.1 to 10 mg/kg per day.

In another aspect, the present invention relates to a method for the treatment or prevention of cancer, which comprises administering an effective amount of the above pharmaceutical composition to a subject. The cancers to be treated or prevented may be any cancers so far as they express an eEF2 protein, and include, for example, lung adenocarcinoma, non-small cell lung cancer, small-cell lung cancer, head-and-neck squamous cell cancer, esophageal cancer, esophageal squamous cell cancer, stomach cancer, colon cancer, pancreatic duct cancer, glioblastoma, and malignant lymphoma. Preferably, the composition of the present invention may be administered to a subject who is determined as "positive" by the above method for detecting cancer.

In still another aspect, the present invention relates to use of the above double-stranded siRNA for the production of a pharmaceutical for the treatment or prevention of cancer.

In still another aspect, the present invention relates to an shRNA or siRNA which inhibits cancer cell proliferation. In general, the shRNA (short hairpin RNA or small hairpin RNA) is an RNA in which a sense strand and an antisense strand are linked through a loop sequence, and may produce a double-stranded siRNA by intracellular cleavage of the loop structure. The siRNA of the present invention is preferably a double-stranded siRNA. There is no particular limitation on regions in the eEF2 targeted by the shRNA or siRNA of the present invention, and an shRNA or siRNA can be exemplified as a preferred example which targets at an mRNA transcribed from the following DNA sequence:

```
                                        (SEQ ID NO: 18)
    5'-gcc tggccgagga catcgataaa ggcgagg-3';
    or (SEQ ID NO: 19)
    5'-actcaac cataacactt gatgccgttt ctt-3'.
```

The shRNA of the present invention may be one transcribed from a vector containing a DNA sequence consisting of sense sequence-loop sequence-antisense sequence of the above DNA sequence. When transcribed from a vector containing such a DNA sequence to an RNA, RNAs derived from a sense sequence and an antisense sequence bind to each other to form a short hairpin RNA, and are stabilized. In this connection, the loop sequence used in the present invention may be any sequences, which can be selected suitably by those skilled in the art. An siRNA which can hybridize with an mRNA transcribed from 5'-gcc tggccgagga catcgataaa ggcgagg-3' (SEQ ID NO:18) or 5'-actcaac cataacactt gatgccgttt ctt-3' (SEQ ID NO:19) can be exemplified as a preferred example of the siRNA of the present invention. An siRNA which has a sequence complementary to an mRNA transcribed from 5'-gcc tggccgagga catcgataaa ggcgagg-3' (SEQ ID NO:18) or 5'-actcaac cataacactt gatgccgttt ctt-3' (SEQ ID NO:19) can be mentioned as a more specific example of the siRNA of the present invention. Alternatively, the siRNA of the present invention may be a double-stranded siRNA composed of a sense strand and an antisense strand of an mRNA corresponding to the DNA sequence shown in SEQ ID NO:18 or 19. An shRNA containing an RNA which can hybridize with an mRNA transcribed from 5'-gcc tggccgagga catcgataaa ggcgagg-3' (SEQ ID NO:18) and an RNA which can hybridize with the RNA can be exemplified as a preferred example of the shRNA of the present invention. Also, an shRNA containing an RNA which can hybridize with an mRNA transcribed from 5'-actcaac cataacactt gatgccgttt ctt-3' (SEQ ID NO:19) and an RNA which can hybridize with the RNA can be exemplified as a preferred example of the shRNA of the present invention. An shRNA can be mentioned as a more specific example of the shRNA of the present invention, which is transcribed from a nucleic acid having the following DNA sequence:

```
                                        (SEQ ID NO: 20)
5'-gcc tggccgagga catcgatgaa agcgtgg cttcctgtca cctcgcc tttatcgatg tcctcggcca ggc-3';

(SEQ ID NO: 22)
5'-actcaac cataacactt gataccattt gtt cttcctgtca aag aaacggcatc aagtgttatg gttgagt-3';

(SEQ ID NO: 21)
3'-cgg accggctcct gtagctactt tcgcacc gaaggacagt ggagcgg aaatagctac aggagccggt ccg-5';
or
                                        (SEQ ID NO: 23)
3'-tgagttg gtattgtgaa ctatggtaaa caa gaaggacagt ttc tttgccgtag ttcacaatac caactca-5'.
```

In the present invention, the above DNA sequence or RNA sequence may have addition, deletion or substitution of 1, 2, or 3 bases. Alternatively, the sequence in the present invention may have a sequence homology of 90% or more, preferably 95% or more, and more preferably 95, 96, 97, 98, or 99% or more to the above DNA sequence or RNA sequence. In this connection, the homology, condition of hybridization, and length of the siRNA are as described above. Also, in the present invention, the above DNA sequence or RNA sequence may have addition, deletion, substitution and/or insertion of 1, 2, or 3 bases.

The shRNA or siRNA of the present invention can be prepared by a method conventional to those skilled in the art. For example, it may be synthesized in vitro chemically or enzymatically, or synthesized in vivo, but the method is not limited thereto. Also, the shRNA or siRNA of the present invention may be prepared in the form of an shRNA expression vector or a siRNA expression vector containing a DNA sequence as shown in the above SEQ ID NO:20 or 22. In this case, for example, tRNA-shRNA expression vector, piGENE tRNA Pur (Clontech, Palo Alto, Calif.) may be used for the preparation.

Methods for introducing or administering the shRNA or siRNA of the present invention may be those known to those skilled in the art such as a calcium phosphate method using a transfection reagent, a liposome method, a non-liposome method, electroporation, and a magnetic particle method. Alternatively, a method may be adopted in which the RNA is integrated into a conventional siRNA expression vector and the vector is introduced by a known method as described above. The shRNA or siRNA of the present invention may be administered in the form of a pharmaceutical composition as described below.

The present invention provides a pharmaceutical composition for the treatment or prevention of cancer, comprising the above shRNA or siRNA as an active ingredient. The pharmaceutical composition of the present invention may also contain a known anticancer drug.

The pharmaceutical composition of the present invention may contain a nucleic acid encoding the shRNA or siRNA of the present invention (for example, a nucleic acid containing a DNA sequence shown in SEQ ID NO:20 or 22) as an active ingredient. For example, the nucleic acid may be one in which a nucleic acid containing such a DNA sequence is integrated into a commercially available shRNA expression vector or siRNA expression vector. Thus, the present invention provides a nucleic acid encoding the shRNA or siRNA of the present invention, and a vector containing the nucleic acid.

The pharmaceutical composition of the present invention may contain pharmaceutically acceptable conventional carriers and additives. The dosage form of the pharmaceutical composition of the present invention may be oral administration or parenteral administration (for example, intravenous administration, intradermal administration, subcutaneous administration, intramuscular administration, transnasal administration or oral administration). Also, the effective amount of the shRNA or siRNA of the present invention administered through the pharmaceutical composition of the present invention can be determined depending on conditions of subjects such as, for example, weight, age, sex and health state of subjects, as well as amount of food, frequency of administration, method of administration, amount of excretion, seriousness of disease and the like.

In another aspect, the present invention relates to a method for the treatment or prevention of cancer, which comprises administering an effective amount of the above pharmaceutical composition to a subject. Cancers to be treated or prevented may be any cancers so far as they express an eEF2 protein, and include, for example, lung adenocarcinoma, non-small cell lung cancer, small-cell lung cancer, head-and-neck squamous cell cancer, esophageal cancer, esophageal squamous cell cancer, stomach cancer, colon cancer, pancreatic duct cancer, glioblastoma, and malignant lymphoma.

In still another aspect, the present invention relates to use of the above shRNA or siRNA for the production of a pharmaceutical for the treatment or prevention of cancer.

In a further aspect, the present invention relates to a peptide containing contiguous amino acids derived from an eEF2 protein. Examples of the peptide of the present invention are peptides containing an amino acid sequence as described below or peptides consisting of an amino acid sequence described below. Preferably, these peptides have a binding ability to an HLA molecule. Also, these peptides preferably induce a cytotoxic activity. Moreover, these peptides are preferably an HLA-A*2402-restricted eEF2 peptide, an HLA-A*0201-restricted eEF2 peptide, or an HLA-A*0206-restricted eEF2 peptide. Furthermore, these peptides preferably have a length of 9 to 30 amino acids. In addition, the present invention provides a pharmaceutical composition for the treatment or prevention of cancer which comprises these peptides, use of these peptides for the production of a pharmaceutical for the treatment or prevention of cancer, a method for the treatment or prevention of cancer, which comprises administering these peptides to a subject, and others.

Thus, in one aspect, the present invention provides an HLA-A*2402-restricted eEF2 peptide. Also, the present invention provides an HLA-A*2402-restricted eEF2 peptide for the treatment or prevention of cancer in an HLA-A*2402-positive subject, as well as a pharmaceutical composition containing the same. An exemplary HLA-A*2402-restricted eEF2 peptide used in the present invention is a peptide having an amino acid sequence composed of contiguous amino acids derived from an eEF2 protein or a peptide containing an amino acid sequence composed of contiguous amino acids derived from an eEF2 protein, wherein the above amino acid sequence is selected from the group consisting of:

Arg Phe Tyr Ala Phe Gly Arg Val Phe (SEQ ID NO:4);
Ala Phe Gly Arg Val Phe Ser Gly Leu (SEQ ID NO:5);
Arg Phe Asp Val His Asp Val Thr Leu (SEQ ID NO:6);
Ala Tyr Leu Pro Val Asn Glu Ser Phe (SEQ ID NO:7); and an amino acid sequence having substitution or deletion or addition of several amino acids, for example, 1 to 9, preferably 1 to 5, 1 to 4, 1 to 3, more preferably 1 to 2 amino acids, and still more preferably one amino acid in one of the above amino acid sequences; but is not limited to these peptides. Also, a peptide may be contained wherein the above amino acid sequence is selected from the group consisting of amino acid sequences having substitution, deletion, addition and/or insertion of several amino acids, for example, 1 to 9, preferably 1 to 5, 1 to 4, 1 to 3, more preferably 1 to 2 amino acids, and still more preferably one amino acid in one of the above amino acid sequences. In case an amino acid in the above peptides is substituted, preferred substitution sites are an amino acid at position 2 and/or position 9. A preferred example of an amino acid at position 2 in the above peptides is Phe or Tyr. Also, a preferred example of an amino acid at position 9 in the above peptides is Ile, Leu or Phe. Specific examples of such a modified-type peptide are peptides as shown in Table 12 or Table 13. A preferred eEF2 peptide in the present invention is Ala Tyr Leu Pro Val Asn Glu Ser Phe (SEQ ID NO:7). In this regard, however, it is essential for all the above peptides to retain a binding ability to the HLA-A*2402 molecule. In the present specification, a peptide retaining a binding ability to the HLA-A*2402 is referred to as an HLA-A*2402-restricted eEF2 peptide. In addition, the above peptides of the present invention may be used for a subject other than the HLA-A*2402-positive subject. Accordingly, the present invention provides a peptide containing any one of the above amino acid sequences, and a pharmaceutical composition containing the peptide.

In another aspect, the present invention provides an HLA-A*0201-restricted eEF2 peptide. Also, the present invention provides a pharmaceutical composition for the treatment or prevention of cancer in an HLA-A*0201-positive subject, comprising the HLA-A*0201-restricted eEF2 peptide. The HLA-A*0201-restricted eEF2 peptide used in the present invention is a peptide having an amino acid sequence composed of contiguous amino acids derived from an eEF2 protein or a peptide containing an amino acid sequence composed of contiguous amino acids derived from an eEF2 protein. Candidates of the HLA-A*0201-restricted eEF2 peptide used in the present invention are exemplified in the following Tables 1 to 7. Among them, an example of a preferred peptide in the present invention is a peptide wherein the above amino acid sequence is selected from the group consisting of:
Arg Leu Met Glu Pro Ile Tyr Leu Val (SEQ ID NO:8);
Lys Leu Val Glu Gly Leu Lys Arg Leu (SEQ ID NO:9);
Tyr Leu Asn Glu Ile Lys Asp Ser Val (SEQ ID NO:10);
Ile Leu Thr Asp Ile Thr Lys Gly Val (SEQ ID NO:11);
Leu Met Met Tyr Ile Ser Lys Met Val (SEQ ID NO:12);
Lys Leu Pro Arg Thr Phe Cys Gln Leu (SEQ ID NO:13);
Leu Ile Leu Asp Pro Ile Phe Lys Val (SEQ ID NO:14); and
an amino acid sequence having substitution or deletion or addition of several amino acids, for example, 1 to 9, preferably 1 to 5, 1 to 4, 1 to 3, more preferably 1 to 2 amino acids, and still more preferably one amino acid in one of the above amino acid sequences; but is not limited to these peptides. Also, a peptide may be contained wherein the above amino acid sequence is selected from the group consisting of amino acid sequences having substitution, deletion, addition and/or insertion of several amino acids, for example, 1 to 9, preferably 1 to 5, 1 to 4, 1 to 3, more preferably 1 to 2 amino acids, and still more preferably one amino acid in one of the above amino acid sequences. Among them, a particularly preferred HLA-A*0201-restricted eEF2 peptide is Arg Leu Met Glu Pro Ile Tyr Leu Val (SEQ ID NO:8) or Ile Leu Thr Asp Ile Thr Lys Gly Val (SEQ ID NO:11). Also, the HLA-A*0201-restricted eEF2 peptide of the present invention may have a substitution of an amino acid, particularly, at position 2 and/or at position 9 with another amino acid. A preferred example of the amino acid at position 2 in the above peptides is Leu or Met. Also, a preferred example of the amino acid at position 9 in the above peptides is Leu or Val. Examples of such a modified-type peptide are shown in Tables 15 to 21. Preferred examples are peptides having, in the Leu Ile Leu Asp Pro Ile Phe Lys Val (SEQ ID NO:14), a substitution of the amino acid Ile at position 2 with Leu or Met, and/or a substitution of the amino acid Val at position 9 with Leu. Particularly preferred examples are Leu Leu Leu Asp Pro Ile Phe Lys Val (SEQ ID NO:15), Leu Met Leu Asp Pro Ile Phe Lys Val (SEQ ID NO:16), Leu Leu Leu Asp Pro Ile Phe Lys Leu (SEQ ID NO:17), or Leu Met Leu Asp Pro Ile Phe Lys Leu (SEQ ID NO:24). In this regard, however, it is essential for all the above peptides to retain a binding ability to the HLA-A*0201 molecule. In the present specification, a peptide retaining a binding ability to the HLA-A*0201 is referred to as an HLA-A*0201-restricted eEF2 peptide.

Also, the HLA-A*0201-restricted eEF2 peptide of the present invention may have an action of increasing an interferon-γ activity. In addition, the above peptides of the present invention may be used for a subject other than the HLA-A*0201-positive subject. Accordingly, the present invention provides a peptide containing any one of the above amino acid sequences, and a pharmaceutical composition containing the peptide.

In still another aspect, the present invention provides an HLA-A*0206-restricted eEF2 peptide. Also, the present invention provides a pharmaceutical composition for the treatment or prevention of cancer in an HLA-A*0206-positive subject which comprises the HLA-A*0206-restricted eEF2 peptide. The HLA-A*0206-restricted eEF2 peptide used in the present invention is a peptide having an amino acid sequence composed of contiguous amino acids derived from an eEF2 protein or a peptide containing an amino acid sequence composed of contiguous amino acids derived from an eEF2 protein. A preferred example of the HLA-A*0206-restricted eEF2 peptide used in the present invention is a peptide wherein the above amino acid sequence is selected from the group consisting of:
Arg Leu Met Glu Pro Ile Tyr Leu Val (SEQ ID NO:8);
Lys Leu Val Glu Gly Leu Lys Arg Leu (SEQ ID NO:9);
Tyr Leu Asn Glu Ile Lys Asp Ser Val (SEQ ID NO:10);
Ile Leu Thr Asp Ile Thr Lys Gly Val (SEQ ID NO:11);
Leu Met Met Tyr Ile Ser Lys Met Val (SEQ ID NO:12);
Lys Leu Pro Arg Thr Phe Cys Gln Leu (SEQ ID NO:13);
Leu Ile Leu Asp Pro Ile Phe Lys Val (SEQ ID NO:14); and
an amino acid sequence having substitution or deletion or addition of several amino acids, for example, 1 to 9, preferably 1 to 5, 1 to 4, 1 to 3, more preferably 1 to 2 amino acids, and still more preferably one amino acid in one of the above amino acid sequences; but is not limited to these peptides. Also, a peptide may be contained wherein the above amino acid sequence is selected from the group consisting of amino acid sequences having substitution, deletion, addition and/or insertion of several amino acids, for example, 1 to 9, preferably 1 to 5, 1 to 4, 1 to 3, more preferably 1 to 2 amino acids, and still more preferably one amino acid in one of the above amino acid sequences. In this regard, however, it is essential for all the above peptides to retain a binding ability to the HLA-A*0206 molecule. In the present specification, a peptide retaining a binding ability to the HLA-A*0206 is referred to as an HLA-A*0206-restricted eEF2 peptide. Also, the HLA-A*0206-restricted eEF2 peptide of the present invention may have an action of increasing an interferon-γ activity. In addition, the above peptides of the present invention may be used for a subject other than the HLA-A*0206-positive subject. Accordingly, the present invention provides a peptide containing any one of the above amino acid sequences, and a pharmaceutical composition containing the peptide.

TABLE 1

| Candidate peptide number | Amino acid sequence | Starting residue number (Amino acid residue number in SEQ ID NO: 1) |
|---|---|---|
| 1 | LILDPIFKV (SEQ ID NO: 14) | 292 |
| 2 | RLMEPIYLV (SEQ ID NO: 8) | 739 |

TABLE 1-continued

| Candidate peptide number | Amino acid sequence | Starting residue number (Amino acid residue number in SEQ ID NO: 1) |
|---|---|---|
| 3 | KLVEGLKRL (SEQ ID NO: 9) | 519 |
| 4 | YLNEIKDSV (SEQ ID NO: 10) | 671 |
| 5 | ILTDITKGV (SEQ ID NO: 11) | 661 |
| 6 | LMMYISKMV (SEQ ID NO: 12) | 394 |
| 7 | KLPRTFCQL (SEQ ID NO: 13) | 284 |
| 8 | GLHGWAFTL (SEQ ID NO: 50) | 217 |
| 9 | GLVGVDQFL (SEQ ID NO: 51) | 471 |
| 10 | WLPAGDALL (SEQ ID NO: 52) | 343 |
| 11 | VVVDCVSGV (SEQ ID NO: 53) | 127 |
| 12 | AIAERIKPV (SEQ ID NO: 54) | 146 |
| 13 | IMIDPVLGT (SEQ ID NO: 55) | 203 |
| 14 | RLAKSDPMV (SEQ ID NO: 56) | 526 |
| 15 | GLVSTGLKV (SEQ ID NO: 57) | 419 |

TABLE 2

| Candidate peptide number | Amino acid sequence | Starting residue number (Amino acid residue number in SEQ ID NO: 1) |
|---|---|---|
| 16 | LVGVDQFLA (SEQ ID NO: 58) | 472 |
| 17 | KMDRALLEL (SEQ ID NO: 59) | 159 |
| 18 | FVVKAYLPV (SEQ ID NO: 60) | 782 |
| 19 | TILMMGRYV (SEQ ID NO: 61) | 450 |
| 20 | NLIDSPGHV (SEQ ID NO: 62) | 101 |
| 21 | ALDNFLDKL (SEQ ID NO: 63) | 850 |
| 22 | CLYASVLTA (SEQ ID NO: 64) | 728 |
| 23 | LLQMITIHL (SEQ ID NO: 65) | 350 |

TABLE 2-continued

| Candidate peptide number | Amino acid sequence | Starting residue number (Amino acid residue number in SEQ ID NO: 1) |
|---|---|---|
| 24 | QVAGTPMFV (SEQ ID NO: 66) | 775 |
| 25 | VVAGFQWAT (SEQ ID NO: 67) | 679 |
| 26 | LMMNKMDRA (SEQ ID NO: 68) | 155 |
| 27 | NMRVMKFSV (SEQ ID NO: 69) | 696 |
| 28 | NMRVMKFSV (SEQ ID NO: 70) | 493 |
| 29 | AIMDKKANI (SEQ ID NO: 71) | 11 |
| 30 | CVFDWQIL (SEQ ID NO: 72) | 812 |

TABLE 3

| Candidate peptide number | Amino acid sequence | Starting residue number (Amino acid residue number in SEQ ID NO: 1) |
|---|---|---|
| 31 | GIPALDNFL (SEQ ID NO: 73) | 847 |
| 32 | VLNRKRGHV (SEQ ID NO: 74) | 762 |
| 33 | MMGRYVEPI (SEQ ID NO: 75) | 453 |
| 34 | FLVKTGTIT (SEQ ID NO: 76) | 478 |
| 35 | QVVGGIYGV (SEQ ID NO: 77) | 754 |
| 36 | RVTDGALVV (SEQ ID NO: 78) | 120 |
| 37 | FQWATKEGA (SEQ ID NO: 79) | 683 |
| 38 | VAGTPMFVV (SEQ ID NO: 80) | 776 |
| 39 | GLKEGIPAL (SEQ ID NO: 81) | 843 |
| 40 | SVLTAQPRL (SEQ ID NO: 82) | 732 |
| 41 | PMFVVKAYL (SEQ ID NO: 83) | 780 |
| 42 | VMKFSVSPV (SEQ ID NO: 84) | 496 |
| 43 | WAFTLKQFA (SEQ ID NO: 85) | 221 |
| 44 | FEHAHNMRV (SEQ ID NO: 86) | 488 |

TABLE 3-continued

| Candidate peptide number | Amino acid sequence | Starting residue number (Amino acid residue number in SEQ ID NO: 1) |
|---|---|---|
| 45 | KQFAEMYVA (SEQ ID NO: 87) | 226 |

TABLE 4

| Candidate peptide number | Amino acid sequence | Starting residue number (Amino acid residue number in SEQ ID NO: 1) |
|---|---|---|
| 46 | RVFSGLVST (SEQ ID NO: 88) | 415 |
| 47 | RIVENVNVI (SEQ ID NO: 89) | 180 |
| 48 | MMNKMDRAL (SEQ ID NO: 90) | 156 |
| 49 | EMYVAKFAA (SEQ ID NO: 91) | 230 |
| 50 | FSVSPVVRV (SEQ ID NO: 92) | 499 |

TABLE 4-continued

| Candidate peptide number | Amino acid sequence | Starting residue number (Amino acid residue number in SEQ ID NO: 1) |
|---|---|---|
| 51 | ELYQTFQRI (SEQ ID NO: 93) | 173 |
| 52 | SVVAGFQWA (SEQ ID NO: 94) | 678 |
| 53 | IMNFKKEET (SEQ ID NO: 95) | 304 |
| 54 | GALVVVDCV (SEQ ID NO: 96) | 124 |
| 55 | KVEDMMKKL (SEQ ID NO: 97) | 252 |
| 56 | RNMSVIAHV (SEQ ID NO: 98) | 20 |
| 57 | KANIRNMSV (SEQ ID NO: 99) | 16 |
| 58 | TVSEESNVL (SEQ ID NO: 100) | 582 |
| 59 | GVCVQTETV (SEQ ID NO: 101) | 134 |
| 60 | DITKGVQYL (SEQ ID NO: 102) | 664 |

TABLE 5

| Candidate peptide number | Amino acid sequence | Starting residue number (Amino acid residue number in SEQ ID NO: 1) |
|---|---|---|
| 61 | AVMRRWLPA (SEQ ID NO: 103) | 338 |
| 62 | FSSEVTAAL (SEQ ID NO: 104) | 111 |
| 63 | KLWGDRYFD (SEQ ID NO: 105) | 259 |
| 64 | LEPEELYQT (SEQ ID NO: 106) | 169 |
| 65 | GVDQFLVKT (SEQ ID NO: 107) | 474 |
| 66 | FTLKQFAEM (SEQ ID NO: 108) | 223 |
| 67 | AEMYVAKFA (SEQ ID NO: 109) | 229 |
| 68 | FTADLRSNT (SEQ ID NO: 110) | 796 |
| 69 | MIDPVLGTV (SEQ ID NO: 111) | 204 |
| 70 | YLPVNESFG (SEQ ID NO: 112) | 787 |
| 71 | NPADLPKLV (SEQ ID NO: 113) | 513 |
| 72 | GPAERAKKV (SEQ ID NO: 114) | 245 |
| 73 | DLPKLVEGL (SEQ ID NO: 115) | 516 |
| 74 | MVNFTVDQI (SEQ ID NO: 116) | 1 |
| 75 | GGQAFPQCV (SEQ ID NO: 117) | 805 |

TABLE 6

| Candidate peptide number | Amino acid sequence | Starting residue number (Amino acid residue number in SEQ ID NO: 1) |
|---|---|---|
| 76 | VLTAQPRLM (SEQ ID NO: 118) | 733 |
| 77 | SGLHGWAFT (SEQ ID NO: 119) | 216 |
| 78 | ITIHLPSPV (SEQ ID NO: 120) | 354 |
| 79 | KSTLTDSLV (SEQ ID NO: 121) | 32 |
| 80 | GELHLEICL (SEQ ID NO: 122) | 550 |
| 81 | CITIKSTAI (SEQ ID NO: 123) | 67 |
| 82 | SEVTAALRV (SEQ ID NO: 124) | 113 |
| 83 | FTVDQIRAI (SEQ ID NO: 125) | 4 |
| 84 | AQPRLMEPI (SEQ ID NO: 126) | 736 |
| 85 | YLAEKYEWD (SEQ ID NO: 127) | 634 |
| 86 | KIWCFGPDG (SEQ ID NO: 128) | 648 |
| 87 | GTVGFGSGL (SEQ ID NO: 129) | 210 |
| 88 | VEIQCPEQV (SEQ ID NO: 130) | 747 |
| 89 | KNPADLPKL (SEQ ID NO: 131) | 512 |
| 90 | GVRFDVHDV (SEQ ID NO: 132) | 699 |

TABLE 7

| Candidate peptide number | Amino acid sequence | Starting residue number (Amino acid residue number in SEQ ID NO: 1) |
|---|---|---|
| 91 | TTFEHAHNM (SEQ ID NO: 133) | 486 |
| 92 | GNIVGLVGV (SEQ ID NO: 134) | 467 |
| 93 | IIPTARRCL (SEQ ID NO: 135) | 721 |
| 94 | PLMMYISKM (SEQ ID NO: 136) | 393 |
| 95 | GQLGPAERA (SEQ ID NO: 137) | 242 |
| 96 | LKQFAEMYV (SEQ ID NO: 138) | 225 |
| 97 | MGNIMIDPV (SEQ ID NO: 139) | 200 |
| 98 | KVFDAIMNF (SEQ ID NO: 140) | 299 |
| 99 | MEPIYLVEI (SEQ ID NO: 141) | 741 |

The peptide used in the present invention is derived from an eEF2 protein, and may consist of the above contiguous amino acid sequence or a modified sequence thereof, or contain such a sequence. In case the peptide contains the above amino acid sequence, there is no particular limitation on the length of the peptide, and the peptide may have any length. Preferred examples of the peptide containing the above contiguous amino acid sequence are peptides having 9 to 30 amino acids, preferably peptides having 9 to 15 amino acids, and more preferably peptides having 9 to 12 amino acids. Thus, the peptide used in the present invention may be, for example, the peptide itself consisting of the above amino acid sequence, or an eEF2 protein containing the above amino acid sequence or a portion thereof. In a peptide used in the present invention, a variety of substances can also be bound to an N-end and/or a C-end of a peptide containing the above amino acid sequence. For example, amino acids, peptides, and analogues thereof may be bound to the peptide. In case these substances are bound to a peptide used in the present invention, they are treated, for example, by an enzyme and the like in the body or through a process such as intracellular processing, and a peptide consisting of the above amino acid sequence is finally produced. The peptide is presented on a cell surface as a complex with an HLA-A*2402 molecule or HLA-A*0201 molecule, thereby being able to produce an induction effect of cytotoxic T cells (CTL). These substances may be those which regulate solubility of a peptide used in the present invention, or improve stability of the peptide (e.g. protease-resistant effect), or, for example, specifically deliver a peptide used in the present invention to a given tissue or organ, or have an enhancing action of an uptake efficiency of antigen-presenting cells and the like. Also, these substances may be a substance which increases an ability to induce the CTL, for example, a helper peptide and the like.

The peptide used in the present invention can be synthesized using a method usually used in this art or a modified method thereof. Such a synthetic method is described, for example, in Peptide Synthesis, Interscience, New York, 1966; The Proteins, Vol. 2, Academic Press Inc., New York, 1976; Peptide Synthesis, Maruzen Company Ltd., 1975; Basis and Experiment of Peptide Synthesis, Maruzen Company Ltd., 1985; Development of Medicine, Sequel, Vol. 14, Peptide Synthesis, Hirokawa Shoten Co., 1991 and others.

Also, the peptide used in the present invention can be prepared using a genetic engineering technique on the basis of the information on a nucleotide sequence encoding the peptide used in the present invention. Such a genetic engineering technique is well known to those skilled in the art.

The present invention relates to a pharmaceutical composition for the treatment or prevention of cancer, comprising the above eEF2 peptide. Since the eEF2 gene is highly expressed, for example, in lung adenocarcinoma, small-cell lung cancer, esophageal cancer, stomach cancer, colon cancer, pancreatic duct cancer, malignant glioblastoma, malignant lymphoma, head-and-neck squamous cell cancer, and the like, the pharmaceutical composition of the present invention can be used for the treatment or prevention of cancer expressing the eEF2 gene. When the pharmaceutical composition of the present invention is administered to an HLA-A*2402- or HLA-A*0201-positive subject, an eEF2-specific CTL is induced by an HLA-A*2402-restricted eEF2 peptide or an HLA-A*0201-restricted eEF2 peptide contained in the pharmaceutical composition, and cancer cells in the subject are impaired by such a CTL.

The pharmaceutical composition of the present invention may contain, for example, carriers, excipients and the like, in addition to the above eEF2 peptide as an active ingredient. Since the HLA-A*2402-restricted eEF2 peptide or HLA-A*0201-restricted eEF2 peptide contained in the pharmaceutical composition of the present invention induces an eEF2-specific CTL, the pharmaceutical composition of the present invention may contain a suitable adjuvant, or may be administered together with a suitable adjuvant in order to enhance its induction efficiency. Preferred adjuvants are, for example, a complete or incomplete Freund's adjuvant, aluminum hydroxide and the like, but are not limited thereto. Also, the pharmaceutical composition of the present invention may contain a known peptide, for example, WT1 peptide and the like, as an active ingredient, in addition to the above eEF2 peptide.

The administration method of the pharmaceutical composition of the present invention can be selected suitably depending on conditions such as types of diseases, a state of subjects, and targeted sites. The method may be, for example, intradermal administration, subcutaneous administration, intramuscular administration, intravenous administration, transnasal administration, or oral administration, but is not limited thereto. Furthermore, the method may be a lymphocyte therapy or a DC (dendritic cell) therapy. The amount of a peptide contained in the pharmaceutical composition of the present invention, dosage form of the pharmaceutical composition, number of doses and the like may be selected suitably depending on conditions such as types of diseases, a state of subjects, and targeted sites. The amount of a peptide administered per one dose is usually from 0.0001 mg to 1000 mg, and preferably from 0.001 mg to 10,000 mg.

In another aspect, the present invention relates to a method for the treatment or prevention of cancer, which comprises administering an effective amount of the above pharmaceutical composition to an HLA-A*2402-positive subject or an HLA-A*0201-positive subject. Cancers to be treated or prevented may be any cancers, and include, for example, lung adenocarcinoma, non-small cell lung cancer, small-cell lung cancer, head-and-neck squamous cell cancer, esophageal squamous cell cancer, stomach cancer, colon cancer, pancreatic duct cancer, glioblastoma and malignant lymphoma.

In still another aspect, the present invention relates to use of an eEF2 peptide for the production of the above pharmaceutical composition.

In still another aspect, the present invention relates to a polynucleotide encoding the above eEF2 peptide (hereinafter, also referred to as eEF2 polynucleotide). The polynucleotide of the present invention may be a DNA or an RNA. The base sequence of the polynucleotide of the present invention can be determined on the basis of the amino acid sequence of the above eEF2 peptide. The above polynucleotide can be prepared, for example, by a DNA or RNA synthetic method, a PCR method and the like.

In another aspect, the present invention relates to an expression vector containing the above polynucleotide (hereinafter, also referred to as eEF2 expression vector). The types of expression vectors, sequences contained in addition to the above polynucleotide sequence and the like can be selected suitably depending on types of hosts into which the expression vector is introduced, the purpose of introducing the expression vector and the like. The expression vector of the present invention is administered to a subject to produce an eEF2 peptide in a living body and to induce an eEF2-specific CTL. The CTL impairs hematopoietic organ tumor cells, solid cancer cells and the like in a subject, thereby allowing the hematopoietic organ tumor and solid cancer to be treated or prevented.

In still another aspect, the present invention relates to a pharmaceutical composition for the treatment or prevention of cancer, comprising the above eEF2 polynucleotide or the above eEF2 expression vector. Composition, administration method and the like of the pharmaceutical composition of the present invention in this aspect are as described above.

In another aspect, the present invention relates to a method for the treatment or prevention of cancer, which comprises administering a pharmaceutical composition containing an effective amount of the above eEF2 polynucleotide or eEF2 expression vector to a subject. Cancers to be treated or prevented include, for example, lung adenocarcinoma, non-small cell lung cancer, small-cell lung cancer, head-and-neck squamous cell cancer, esophageal squamous cell cancer, stomach cancer, colon cancer, pancreatic duct cancer, glioblastoma, malignant lymphoma and the like.

In still another aspect, the present invention relates to use of an eEF2 polynucleotide or an eEF2 expression vector for the production of a pharmaceutical composition containing the above eEF2 polynucleotide or eEF2 expression vector.

In another aspect, the present invention relates to cells containing the above eEF2 expression vector. The cells of the present invention can be prepared, for example, by transforming host cells such as E. coli, yeast, insect, and animal cells using the above expression vector. A method for introducing the expression vector into the host cells can be selected suitably from various methods. It is also possible to prepare the peptide of the present invention by culturing transformed cells, and recovering and purifying an eEF2 peptide produced.

In a further aspect, the present invention relates to an eEF2-specific CTL which is induced by the above eEF2 peptide. The CTL of the present invention recognizes a complex of an eEF2 peptide with an HLA-A*2402 molecule or an HLA-A*0201 molecule. Accordingly, HLA-A*2402-positive or HLA-A*0201-positive and highly eEF2-expressing tumor cells can be impaired specifically using the CTL of the present invention.

In another aspect, the present invention relates to a method for the treatment or prevention of cancer, which comprises administering an eEF2-specific CTL to an HLA-A*2402 positive or HLA-A*0201-positive subject. The administration method of the eEF2-specific CTL can be selected suitably depending on conditions such as types of diseases, a state of subjects, and targeted sites. The method may be, for example, intravenous administration, intradermal administration, subcutaneous administration, intramuscular administration, transnasal administration, or oral administration, but is not limited thereto.

In another aspect, the present invention relates to a method for inducing an eEF2-specific CTL, which comprises culturing peripheral blood mononuclear cells in the presence of the above HLA-A*2402-restricted eEF2 peptide or HLA-A*0201-restricted eEF2 peptide, and the eEF2-specific CTL is induced from the peripheral blood mononuclear cells. Subjects from which the peripheral blood mononuclear cells are derived may be any subjects so far as they have an HLA-A*2402 molecule or an HLA-A*0201 molecule. By culturing the peripheral blood mononuclear cells in the presence of the HLA-A*2402-restricted eEF2 peptide or HLA-A*0201-restricted eEF2 peptide, the eEF2-specific CTL is induced from CTL precursor cells in the peripheral blood mononuclear cells. By administering the eEF2-specific CTL obtained by the present invention to an HLA-A*2402-positive subject or an HLA-A*0201-positive subject, it is possible to treat or prevent a hematopoietic organ tumor and a solid cancer in the subject. In this connection, the peripheral blood mononuclear cells in the present specification include immature antigen-presenting cells (for example, precursors of dendritic cells, B-lymphocytes, macrophages, etc.) which are precursors of antigen-presenting cells. Since the immature antigen-presenting cells are contained, for example, in peripheral blood mononuclear cells and the like, such cells may be cultured in the presence of the above eEF2 peptide.

In still another aspect, the present invention relates to a kit for inducing an eEF2-specific CTL, comprising an HLA-A*2402-restricted eEF2 peptide or an HLA-A*0201-restricted eEF2 peptide as an essential constituent. Preferably, the kit is used in a method for inducing the above eEF2-specific CTL. The kit of the present invention may contain, for example, a sampling means of peripheral blood mononuclear cells, an adjuvant, a reaction vessel and the like, in addition to the above HLA-A*2402-restricted eEF2 peptide or HLA-A*0201-restricted eEF2 peptide. In general, the kit is accompanied with an instruction manual. The kit of the present invention can be used to induce efficiently the eEF2-specific CTL.

In a further aspect, the present invention relates to antigen-presenting cells (for example, dendritic cells, B-lymphocytes, macrophages, etc.) which present the above eEF2 peptide through an HLA-A*2402 molecule or an HLA-A*0201 molecule. The antigen-presenting cells of the present invention are induced by the above HLA-A*2402-restricted eEF2 peptide or HLA-A*0201-restricted eEF2 peptide. The above eEF2-specific CTL is efficiently induced using the antigen-presenting cells of the present invention.

In another aspect, the present invention relates to a method for the treatment or prevention of cancer, which comprises administering antigen-presenting cells, which present the above eEF2 peptide through an HLA-A*2402 molecule or an HLA-A*0201 molecule, to an HLA-A*2402-positive subject or an HLA-A*0201-positive subject. The administration method of the antigen-presenting cells can be selected suitably depending on conditions such as types of diseases, a state of subjects, and targeted sites. The method may be, for example, intravenous administration, intradermal administration, subcutaneous administration, intramuscular administration, transnasal administration, or oral administration, but is not limited thereto.

In a further aspect, the present invention relates to a method for preventing or treating cancer, which comprises inducing antigen-presenting cells which present an eEF2 peptide through an HLA-A*2402 molecule or an HLA-A*0201 molecule, the method comprising the steps of:
 (a) reacting a sample with a nucleic acid having a nucleotide sequence encoding an amino acid sequence (SEQ ID NO:1) of an eEF2 protein or a partial sequence thereof, or the above eEF2 peptide,
 (b) obtaining antigen-presenting cells which present the eEF2 peptide contained in the sample through the HLA-A*2402 molecule or HLA-A*0201 molecule, and
 (c) administering the antigen-presenting cells to an HLA-A*2402-positive subject or an HLA-A*0201-positive subject. The sample in the above method may be any samples so far as they have a possibility of inclusion of lymphocytes or dendritic cells, and includes, for example, samples from a subject such as blood, cell culture media and the like. The reaction in the above method may be carried out using a conventional technique, preferably using an electroporation technique. The obtainment of the antigen-presenting cells can be carried out using a method known to those skilled in the art. The culture conditions of cells in a sample in each step can be determined suitably by those skilled in the art. The administration method of the antigen-presenting cells may be as described above.

Furthermore, the present invention relates to a kit for preventing or treating cancer, comprising, as an essential constituent, a nucleic acid having a nucleotide sequence encoding an amino acid sequence (SEQ ID NO:1) of an eEF2 protein or a partial sequence thereof, or an eEF2 peptide. The kit comprises antigen-presenting cells which present the above eEF2 peptide through an HLA-A*2402 molecule or an HLA-A*0201 molecule. Also, the kit of the present invention may contain, for example, a sampling means, a reaction vessel and the like, in addition to the above essential constituent. In general, the kit is accompanied with an instruction manual. The antigen-presenting cells which present an eEF2 peptide through an HLA-A*2402 molecule or an HLA-A*0201 molecule can be obtained efficiently using the kit of the present invention, and cancer can be treated or prevented by administering the antigen-presenting cells.

In another aspect, the present invention relates to an antibody against an HLA-A*2402-restricted eEF2 peptide or an HLA-A*0201-restricted eEF2 peptide, or an antibody against a polynucleotide encoding the peptide. The antibody of the present invention may be either a polyclonal antibody or a monoclonal antibody.

In a further aspect, the present invention relates to a method for diagnosing cancer, characterized by the use of the above eEF2-specific CTL, antigen-presenting cells which present the above eEF2 peptide through an HLA-A*2402 molecule or an MLA-A*0201 molecule, or an antibody against an HLA-A*2402-restricted eEF2 peptide or an HLA-A*0201-restricted eEF2 peptide or an antibody against a polynucleotide encoding the peptide. The eEF2-specific CTL is preferably used in the diagnosis method of the present invention. For example, cancer can be diagnosed by incubating the above CTL, antigen-presenting cells or antibody with a sample from an HLA-A*2402-positive subject or an HLA-A*0201-positive subject, or administering the above CTL, antigen-presenting cells or antibody to an HLA-A*2402-positive subject or an HLA-A*0201-positive subject, and then determining, for example, the position, site, amount or the like of the CTL, antigen-presenting cells or antibody. The above CTL, antigen-presenting cells or antibody may be labeled. By such labeling, the diagnosis method of the present invention can be carried out efficiently.

In another aspect, the present invention relates to a kit for diagnosis of cancer, comprising, as an essential constituent, the above eEF2-specific CTL, antigen-presenting cells which present an eEF2 peptide through an HLA-A*2402 molecule or an HLA-A*0201 molecule, or an antibody against an HLA-A*2402-restricted eEF2 peptide or an HLA-A*0201-restricted eEF2 peptide or an antibody against a polynucleotide encoding the peptide.

In a further aspect, the present invention relates to a method for determining the presence or amount of an eEF2-specific CTL in an HLA-A*2402-positive subject or an HLA-A*0201-positive subject, which comprises the steps of:
(a) reacting a complex of an eEF2 peptide and an HLA-A*2402 molecule or an HLA-A*0201 molecule with a sample from the subject, and then
(b) determining the presence or amount of the CTL recognizing the complex contained in the sample.

The sample from the subject may be any samples so far as they have a possibility of inclusion of lymphocytes, and includes, for example, body fluid such as blood and lymph fluid, tissues and the like. The complex of an eEF2 peptide and an HLA-A*2402 molecule or an HLA-A*0201 molecule may be, for example, in the form of a tetramer, pentamer and the like, for example, using a method known to those skilled in the art such as a biotin-streptavidin method. The presence or amount of the CTL recognizing such a complex can be determined by a method known to those skilled in the art. In this aspect of the present invention, the above complex may be labeled. A known label such as a fluorescence label and a radioactive label can be used. By such labeling, the presence or amount of the CTL can be determined easily and rapidly. This aspect of the method of the present invention allows diagnosis of cancer, prognostic diagnosis and the like.

Thus, the present invention also provides a composition comprising a complex of an eEF2 peptide and an HLA-A*2402 molecule or an HLA-A*0201 molecule for determining the presence or amount of an eEF2-specific CTL in an HLA-A*2402-positive subject or an HLA-A*0201-positive subject.

Also, the present invention provides a kit for determining the presence or amount of an eEF2-specific CTL in an HLA-A*2402-positive subject or an HLA-A*0201-positive subject, comprising a complex of an eEF2 peptide and an HLA-A*2402 molecule or an HLA-A*0201 molecule.

In a further aspect, the present invention relates to a method for obtaining an eEF2-specific CTL using a complex of an eEF2 peptide and an HLA-A*2402 molecule or an HLA-A*0201 molecule, which comprises the steps of:
(a) reacting a sample with the complex, and
(b) obtaining the CTL which recognizes the complex contained in the sample.

The complex of an eEF2 peptide and an HLA-A*2402 molecule or an HLA-A*0201 molecule is as described above. The sample may be any samples so far as they have a possibility of inclusion of lymphocytes, and includes, for example, samples from a subject such as blood, cell culture media and the like. The obtainment of the CTL recognizing the complex can be carried out using a method known to those skilled in the art, for example, using FACS, MACS and the like. The eEF2-specific CTL obtained can be cultured to use for the treatment or prevention of a variety of cancers.

Thus, the present invention also relates to an eEF2-specific CTL, which can be obtained by a method for obtaining the eEF2-specific CTL using a complex of an eEF2 peptide and an HLA-A*2402 molecule or an HLA-A*0201 molecule.

Furthermore, the present invention relates to a kit for obtaining an eEF2-specific CTL, comprising a complex of an eEF2 peptide and an HLA-A*2402 molecule or an HLA-A*0201 molecule.

In one aspect, the present invention provides a kit for tumorigenesis characterized in that an eEF2 polypeptide is expressed. Thus, the kit of the present invention comprises, as an essential constituent, the step of expressing the eEF2 polypeptide in cells or non-human animals. Accordingly, a polynucleotide encoding an amino acid sequence of the polypeptide or a vector into which the polynucleotide is integrated is an essential constituent. In the present specification, the non-human animals refer to animals other than human. The kit of the present invention is based on a finding that forced expression of an eEF2 protein accelerates a G2/M phase in a cell cycle. The kit of the present invention may also contain, for example, a means for introducing the above polynucleotide or vector into cells or non-human animal tissues, a reagent for introduction, a reaction vessel and the like, in addition to the above polynucleotide or vector. In general, the kit is accompanied with an instruction manual. The kit of the present invention can be used for forming a tumor in vivo or in vitro, and then, for testing effects of candidate molecules against tumorigenesis or cell proliferation, for example.

In this regard, the method of the present invention may be carried out in vivo or in vitro.

EXAMPLES

The present invention is illustrated particularly and specifically by referring to the following examples, which should not be construed as limiting the present invention.

Example 1

Detection of EEF2 IgG Antibody in Sera of Cancer Patients

Cells of lung cancer cell lines PC14 and LU-993, and leukemia cell line K562 were lysed in an SDS-sample buffer. Proteins contained in the buffer were separated by SDS-PAGE, and then transferred to a PVDF membrane. Solutions prepared by diluting sera obtained from 10 patients having lung cancer and 10 healthy subjects by 1500:1 were used as a primary antibody, and IgG antibodies bound to the membrane were visualized using an anti-human IgG antibody. As a result, a protein of about 100 kDa was found which was specifically recognized by the sera from the patients having lung cancer (FIG. 1). FIG. 1 is a typical example of a western blot. Subsequently, the protein was separated and identified as eEF2 by a mass spectrometric technique.

Excessive Expression of EEF2 in Various Cancers

Thin-sliced sections were prepared from paraffin-embedded blocks. After de-paraffin treatment, the sections were subjected to antigen-activating treatment in a citrate buffer (pH 6.0), reacted with an anti-eEF2 antibody (H-118, Santa Cruz Biotechnology, Santa Cruz, Calif., 1:100 dilution) at 4° C. overnight, and then reacted with Envision kit/HRP (Dako Cytomation) at room temperature for 30 minutes. After reacting with 0.7% of an $H_2O_2$ solution, the sections were color-developed using DAB as a substrate, and nuclear-staining was then carried out using hematoxylin. As a result, antibody-positive cells were observed in each affected tissue of patients having lung adenocarcinoma, small-cell lung cancer, head-and-neck squamous cell cancer, esophageal cancer, stomach cancer and colon cancer (FIGS. 2 to 4).

Detection of EEF2 Antibody in Various Types of Cancers

Peripheral blood was obtained from 72 patients having non-small cell lung cancer, 42 patients having colon cancer, 20 patients having head-and-neck squamous cell cancer, 18 patients having glioblastoma, and 17 healthy subjects in agreement. The blood was coagulated and sera were then obtained by centrifugation. A vector pGEX-5X-3 (GE) for expression of a recombinant protein was prepared by inserting a gene sequence encoding an amino acid sequence at positions 411-858 of eEF2. The recombinant GST-eEF2$_{411-858}$ protein purified was adjusted to 150 ng/lane and SDS-PAGE was carried out. The protein on the SDS-PAGE was electrically transferred to a PVDF membrane. The protein was reacted with sera diluted by 1500:1 at room temperature overnight, and IgG antibodies bound to the membrane were visualized using an anti-human IgG antibody. Density of the bands was measured and used as an anti-eEF2 antibody titer. Since the median value of the antibody titer in 17 healthy subjects was 500 densitometric units and the standard deviation was 500, the cutoff level was set to 2,000 densitometric units which was median+3 SD. As a result, it was found that, at a specificity of 94.7%, the eEF2 IgG antibody was positive in 66.7% of non-small cell lung cancer, 71.8% of colon cancer, 60.0% of head-and-neck squamous cell cancer, and 88.9% of glioblastoma (FIG. 5). Expression of the eEF2 protein in various cancers was analyzed by immunostaining. When the percentage of cancer cells showing intense stain as compared with corresponding normal cells was 25% or more of total cancer cells, the expression was judged to be positive (Table 8).

TABLE 8

Excessive expression of eEF2 in various cancers

| Cancer | Positive rate of excessive expression of eEF2 |
| --- | --- |
| Lung adenocarcinoma | 100% (15/15) |
| Small-cell lung cancer | 95.0% (19/20) |
| Esophageal cancer | 58.3% (7/12) |
| Stomack cancer | 92.9% (13/14) |
| Colon cancer | 91.7% (22/24) |
| Pancreatic duct cancer | 55.6% (5/9) |
| Malignant glioblastoma | 50.6% (6/12) |

TABLE 8-continued

Excessive expression of eEF2 in various cancers

| Cancer | Positive rate of excessive expression of eEF2 |
| --- | --- |
| Malignant lymphoma | 94.0% (47/50) |
| Head-and-neck squamous cell cancer | 45.5% (5/11) |

Early Stage Detection of Cancer by EEF2 Antibody

The positive rate of eEF2 antibody titer was compared with the positive rate of CEA in 70 patients (44 in stage I, 13 in stage 11, and 13 in stage III) having non-small cell lung cancer and having a clear serum CEA value. In this connection, the classification of stage I, stage II, and stage III was carried out according to the TNM classification defined by the International Union Against Cancer. The eEF2 antibody titer was determined by dot blotting. As a result, it was found that the positive rate of the eEF2 IgG antibody in each disease stage of non-small cell lung cancer was high even from stage I (Table 9).

TABLE 9

| | | Stage | | |
| --- | --- | --- | --- | --- |
| | | I | II | III |
| Anti-eEF2 IgG antibody | Positive rate | 81.8% | 61.5% | 61.5% |
| CEA | Positive rate | 13.6% | 23.1% | 46.2% |

Relationship Between EEF2 Antibody Titer and Disease-Free Survival Rate

Relationship between the eEF2 antibody titer in non-small cell lung cancer and disease-free survival rate was analyzed. Among 44 patients, the group (11 patients) having an eEF2 antibody titer of 4,000 or more densitometric units has a significantly high disease-free survival rate as compared with the group (26 patients) having an eEF2 antibody titer of 2,000 to 4,000 densitometric units and the group (7 patients) having an eEF2 antibody titer of less than 2,000 densitometric units (log rank test, FIG. 6).

Example 2

Inhibition of Cell Proliferation in Various Cell Lines

A vector expressing a siRNA which targets at sequence: 5'-caugggcaacaucaugaucgauccuguccu-3' of an eEF2 mRNA (hereinafter, referred to as shEF2) was prepared using a tRNA-shRNA expression vector, piGENE tRNA Pur (Clontech, Palo Alto, Calif.). Subsequently, 10 μg of shEF2 or a vacant shRNA vector (shMock) was introduced by electroporation into stomach cancer cell lines AZ-521 and MKN28, colon cancer cell line SW620, lung cancer cell lines LU99B and PC-14, pancreatic cancer cell lines MiaPaCa2 and PCI6, glioblastoma cell lines A172 and U87MG, as well as malignant lymphoma cell lines 134 and YT (each $5 \times 10^5$ cells) expressing the eEF2 using Gene Pulser Xcell (trademark) system (Bio Rad, Hercules, Calif.) under a condition of 165 V and 1000 μF. After 24, 48, 72 and 96 hours of the introduction, cells were treated with trypsin and the number of surviving cells was counted. The experiments were carried out separately 3 times in duplicate. In all cases, the shEF2 significantly inhibited cell proliferation (FIGS. 7 and 8).

Example 3

Selection of EEF2 Peptide

Firstly, 4 peptides were selected by predicting sequences which can bind to an HLA-A*2402 molecule in an amino acid sequence of an eEF2 protein using ProPred-I website. The results are shown in Table 10 below.

(Table 10: Candidate eEF2 peptides having a high binding affinity to HLA-A*2402 molecule, selected using various programs (NetMHC3.0, Rankpep and SYFPEITHI))

TABLE 10

| NetMHC3.0 | | | | Rankpep | | SYFPEITHI | |
|---|---|---|---|---|---|---|---|
| Starting residue number | Affinity (nM) | Binding level | Log score | Starting residue number | Score | Starting residue number | Score |
| 786 | 20 | SB | 0.721 | 633 | 18.484 | 786 | 25 |
| 633 | 188 | WB | 0.516 | 342 | 17.792 | 78 | 20 |
| 220 | 380 | WB | 0.451 | 477 | 15.220 | 265 | 19 |
| 342 | 416 | WB | 0.442 | 786 | 14.930 | 477 | 19 |
| 477 | 671 | | 0.398 | 174 | 13.101 | 412 | 18 |
| 409 | 964 | | 0.365 | 817 | 11.358 | 701 | 17 |
| 174 | 1130 | | 0.350 | 684 | 11.215 | 409 | 16 |
| 684 | 1250 | | 0.341 | 220 | 10.709 | 308 | 15 |
| 177 | 1611 | | 0.317 | 409 | 10.641 | 311 | 15 |
| 265 | 1930 | | 0.301 | 701 | 9.634 | 470 | 15 |
| 78 | 1958 | | 0.299 | 714 | 9.556 | 512 | 15 |
| 412 | 2551 | | 0.275 | 78 | 9.315 | 516 | 15 |
| 231 | 2665 | | 0.271 | 412 | 8.827 | 594 | 15 |
| 729 | 2691 | | 0.270 | 443 | 8.652 | 73 | 14 |
| 744 | 2829 | | 0.265 | 364 | 8.246 | 252 | 14 |
| 73 | 3045 | | 0.259 | 456 | 8.229 | 284 | 14 |
| 70 | 4080 | | 0.232 | 213 | 8.072 | 328 | 14 |
| 644 | 4396 | | 0.225 | 605 | 7.603 | 343 | 14 |
| 701 | 5322 | | 0.207 | 265 | 7.401 | 434 | 14 |
| 759 | 6139 | | 0.194 | 363 | 7.190 | 442 | 14 |
| 638 | 6593 | | | 491 | 7.188 | 456 | 14 |
| 602 | 6673 | | | 177 | 6.847 | 491 | 14 |
| 396 | 7134 | | | 442 | 6.419 | 509 | 14 |
| 284 | 7142 | | | 73 | 6.112 | 537 | 14 |
| 774 | 7954 | | | 850 | 6.015 | 657 | 14 |
| 736 | 8076 | | | 293 | 5.071 | 62 | 13 |
| 442 | 8141 | | | 166 | 4.961 | 70 | 13 |
| 290 | 8704 | | | 763 | 4.815 | 92 | 13 |
| 394 | 8917 | | | 670 | 4.451 | 95 | 13 |
| 300 | 8973 | | | 290 | 4.265 | 111 | 13 |
| 456 | 9299 | | | 285 | 4.229 | 180 | 13 |
| 227 | 9749 | | | 90 | 4.062 | 191 | 13 |
| 180 | 9862 | | | 335 | 4.016 | 201 | 13 |
| 578 | 9900 | | | 396 | 3.935 | 228 | 13 |
| 264 | 10704 | | | 453 | 3.878 | 258 | 13 |
| 491 | 11038 | | | 289 | 3.877 | 277 | 13 |
| 529 | 11225 | | | 1 | 3.85 | 293 | 13 |
| 293 | 12329 | | | 744 | 3.694 | 296 | 13 |
| 811 | 12728 | | | 649 | 3.487 | 299 | 13 |
| 299 | 12938 | | | 38 | 3.281 | 307 | 13 |

The starting residue number is the number shown in SEQ ID NO:1. All candidate eEF2 peptides are composed of 9 residues of amino acids. For example, a peptide having the starting residue number of 786 is a peptide composed of 9 amino acid residues from 786th residue A to 794th residue F in SEQ ID NO:1.

Next, a binding ability to an HLA-A2402 molecule was actually analyzed by an MHC stabilization assay. Briefly, T2-2402 cells (1×10$^6$ cells), receiving forced expression of a human HLA-A*2402 molecule, not having an antigen-presenting ability to an HLA molecule, were incubated in an RPMI1640 medium containing 10 μM of a synthesized peptide and not containing a serum at 27° C. for 16 hours, and then allowed to stand at 37° C. for 3 hours. Since expression of an HLA-A24 molecule on a cell surface is stabilized by binding of a peptide, the expression of the HLA-A24 molecule on a cell surface after treatment with each peptide was analyzed by flow cytometry, and binding ability of each peptide to the HLA-A2402 molecule was evaluated.

As a result, it was found that eEF2$_{409\text{-}417}$ (SEQ ID NO:4), eEF2$_{412\text{-}420}$ (SEQ ID NO:5), eEF2$_{701\text{-}709}$ (SEQ ID NO:6) and eEF2$_{786\text{-}794}$ (SEQ ID NO:7) peptides show a binding ability to the HLA-A2402 molecule (Table 11).

TABLE 11

Identification of HLA-A2402-restricted eEF2 peptide

| eEF2 Peptide | Binding ability to HLA-A2402 molecule |
|---|---|
| eEF2$_{409\text{-}417}$ | + |
| eEF2$_{412\text{-}420}$ | + |
| eEF2$_{701\text{-}709}$ | + |
| eEF2$_{786\text{-}794}$ | + |

Determination of Interferon Activity

T cells were incubated together with HLA-A*2402 molecule-expressing T2 cells pulsed with eEF2 peptides (eEF2$_{409\text{-}417}$, eEF2$_{412\text{-}420}$ and eEF2$_{701\text{-}709}$ peptides) in the presence of brefeldin A (Sigma) at 37° C. for 5 hours. After washing with PBS, CD3 and CD8 molecules which are cell surface antigens were stained by PerCP-conjugated anti-CD3 (BD Biosciences) and PE-conjugated anti-CD8 (Caltag, Burlingame, Calif.) antibodies on ice for 15 minutes. Subsequently, cells were fixed using Cytofix (BD Biosciences) on ice for 20 minutes, and intracellular IFN-γ was reacted with an FITC-conjugated anti-IFN-γ antibody (BD Biosciences) on ice for 30 minutes. Frequency of IFN-γ-positive cells present in CD8-positive T cells was analyzed using a flow cytometer. As a result, it was found that eEF2$_{409\text{-}417}$, eEF2$_{412\text{-}420}$ and eEF2$_{701\text{-}709}$ peptides increase the interferon-γ activity, and is therefore represent an HLA-A*2402-restricted peptide (FIG. 30).

Binding Affinity of Modified-Type EEF2 Peptides to HLA-A*2402 Molecule

Furthermore, a binding affinity of modified-type eEF2 peptides, in which an amino acid at position 2 (hereinafter, also referred to as P2) and/or at position 9 (hereinafter, also referred to as P9) in the amino acid sequences of eEF2$_{786\text{-}794}$ (SEQ ID NO:7) and eEF2$_{409\text{-}417}$ (SEQ ID NO:4) peptides among the above peptides was altered to another amino acid, was predicted as described above.

(Table 12: Prediction of binding affinity of modified-type eEF2$_{786\text{-}794}$ peptides (SEQ ID NOs:25 and 26) to HLA-A*2402 molecule)

TABLE 12

| Candidate peptide | Amino acid sequence | Binding | Binding level | Log score | Score |
|---|---|---|---|---|---|
| 786 | AYLPVNESF | 20 | SB | 0.721 | 14.930 |
| 786 | I AYLPVNESI (SEQ ID NO: 25) | 43 | SB | 0.652 | 15.164 |
| 786 | L AYLPVNESL (SEQ ID NO: 25) | 143 | WB | 0.541 | 14.547 |

TABLE 13

(Table 13: Prediction of binding affinity of modified-type eEF2$_{409-417}$ peptides (SEQ ID NOs: 27 to 31) to HLA-A*2402 molecule)

| | Candidate peptide | | Amino acid sequence | Binding | Binding level | Log score | Score |
|---|---|---|---|---|---|---|---|
| | 409 | | RFYAFGRVF | | | 0.365 | 10.641 |
| Y | 409 | | RFYAFGRVF (SEQ ID NO: 27) | | SB | 0.641 | 15.653 |
| | 409 | I | RFYAFGRVI (SEQ ID NO: 28) | | | 0.252 | 10.875 |
| Y | 409 | I | RFYAFGRVI (SEQ ID NO: 29) | | WB | 0.556 | 15.887 |
| | 409 | L | RFYAFGRVL (SEQ ID NO: 30) | | | 0.164 | 10.258 |
| Y | 409 | L | RFYAFGRVL (SEQ ID NO: 31) | | WB | 0.434 | 15.270 |

Since the eEF2$_{786-794}$ (SEQ ID NO:7) peptide has Y at P2 and F at P9 and the Y and F are anchor residues, improvement of the binding affinity was not recognized even if the original residue is altered to another residue (Table 12). On the other hand, remarkable improvement of the binding affinity was recognized in the eEF2$_{409-417}$ (SEQ ID NO:4) peptide when the residue at P2 is altered to anchor residue Y (Table 13).

Induction of EEF2-specific Killer T Cells

From peripheral blood mononuclear cells obtained from a donor having an HLA-A*2402 molecule, CD4$^+$ CD25$^+$ Treg cells were removed using CD25 MicroBeads (Miltenyi Biotech, Auburn, Calif.). Subsequently, monocytes of the donor were isolated using BD IMag CD14 isolation kit (BD Bioscience), and cultured in X-VIVO15 (Bio Whittaker, Walkersville, Md.) containing IL-4 and GM-CSF and supplemented with 1% human AB serum. Next day, IL-1β, IL-6, TNF-α and PGE-2 were added for maturation of dendritic cells, and culture was continued for further 3 days. The dendritic cells were irradiated (30 G), and then cultured in a medium containing 10 μg/mL of a peptide for 2 hours to pulse the dendritic cells with a peptide. The mononuclear cells (2×10$^6$ cells) having Treg cells removed were then co-cultured with the dendritic cells pulsed with a peptide in a ratio of 10:1 to carry out stimulation by a peptide, and IL-2 was added to the medium on the next day. Subsequently, restimulation was carried out every 10 days by the donor mononuclear cells irradiated and pulsed with a peptide. After carrying out several times of stimulation, the cells were cultured in a medium containing IL-7 and IL-15, and T cell clones are established.

Determination of Cytotoxic Activity

From T cell clones established as described above, CD8-positive T cells were purified using CD8 Microbeads to prepare effector cells. Subsequently, target cells were incubated with $^{51}$Cr-labeled sodium chromate (Amersham Biosciences Corp., NJ) for 1 hour to label the cells. They were then mixed with the effector cells so that the ratio of cell count was 1:1, 3:1 and 9:1 of CTL/target cell (E/T) ratio, and the mixture was allowed to stand for 4 hours. The percentage of cells lysed was calculated according to the following equation:

Specific lysis %=[(cpm experimental release−cpm spontaneous release)/(cpm maximal release−cpm spontaneous release)]×100.

T2-2402 cells pulsed with an eEF2$_{786-794}$ peptide were used as the target cells, and T2-2402 cells not pulsed with the eEF2$_{786-794}$ peptide (SEQ ID NO:7) as a negative control. As a result, it was shown that the specific lysis % of T2-2402 cells pulsed with the eEF2$_{786-794}$ peptide remarkably increases with the increase of the E/T ratio (FIG. 9). Also, colon cancer SW480 cells which show endogenous eEF2 expression and show HLA-A*2402 expression on a cell surface were used as the target cells, and stomach cancer AZ-521 cells and pancreatic cancer MiaPaCa2 cells which show endogenous eEF2 expression but do not show HLA-A*2402 expression on a cell surface as a negative control. As a result, it was shown that cytotoxic T cells activated by the eEF2$_{786-794}$ peptide specifically impair the cells which express the eEF2 and have the HLA-A*2402 molecule (FIG. 10).

Example 4

Selection of EEF2 Peptide

Peptides were selected by predicting sequences which can bind to an HLA-A*0201 molecule in an amino acid sequence of an eEF2 protein using ProPred-I website (Tables 1 to 7). Next, a binding ability to an HLA-A0201 molecule was actually analyzed by an MHC stabilization assay. Briefly, T2-0201 cells ($1\times10^6$ cells), receiving forced expression of a human HLA-A*0201 molecule, not having an antigen-presenting ability to an HLA molecule, were incubated in an RPMI1640 medium containing 10 μM of a synthesized peptide and not containing a serum at 27° C. for 16 hours, and then allowed to stand at 37° C. for 3 hours. Since expression of an HLA-A*0201 molecule on a cell surface is stabilized by binding of a peptide, the expression of the HLA-A0201 molecule on a cell surface after treatment with each peptide was analyzed by flow cytometry, and binding ability of each peptide to the HLA-A0201 molecule was evaluated. As a result, it was found that $eEF2_{284-292}$ (SEQ ID NO:13), $eEF2_{394-402}$ (SEQ ID NO:12), $eEF2_{519-527}$ (SEQ ID NO:9), $eEF2_{661-669}$ (SEQ ID NO:11), $eEF2_{671-679}$ (SEQ ID NO:10) and $eEF2_{739-747}$ (SEQ ID NO:8) peptides show a binding ability to the HLA-A*0201 molecule (Table 14).

TABLE 14

Binding ability of candidate peptide to HLA-A0201 class I molecule

| Candidate peptide | | Amino acid sequence | MFI | % MFI increase |
|---|---|---|---|---|
| NS | | | 5.8 | |
| Non-peptide | | | 275.7 | |
| $eEF2_{292-300}$ | (SEQ ID NO: 14) | LILDPIFKV | 781.03 | 183.3 |
| $eEF2_{739-747}$ | (SEQ ID NO: 8) | RLMEPIYLV | 664.83 | 141.1 |
| $eEF2_{519-527}$ | (SEQ ID NO: 9) | KLVEGLKRL | 437.97 | 58.9 |
| $eEF2_{611-679}$ | (SEQ ID NO: 10) | YLNEIKDSV | 522.71 | 89.6 |
| $eEF2_{661-669}$ | (SEQ ID NO: 11) | ILTDITKGV | 828.16 | 200.4 |
| $eEF2_{394-402}$ | (SEQ ID NO: 12) | LMMYISKMV | 448.41 | 62.6 |
| $eEF2_{284-292}$ | (SEQ ID NO: 13) | KLPRTFCQL | 448.82 | 62.8 |

Determination of Interferon Activity

T cells were incubated together with HLA-A*0201 molecule-expressing T2 cells pulsed with HLA-A*0201-restricted eEF2 peptides in the presence of brefeldin A (Sigma) at 37° C. for 5 hours. After washing with PBS, CD3 and CD8 molecules which are cell surface antigens were stained by PerCP-conjugated anti-CD3 (BD Biosciences) and PE-conjugated anti-CD8 (Caltag, Burlingame, Calif.) antibodies on ice for 15 minutes. Subsequently, cells were fixed using Cytofix (BD Biosciences) on ice for 20 minutes, and intracellular IFN-γ was reacted with an FITC-conjugated anti-IFN-γ antibody (BD Biosciences) on ice for 30 minutes. Frequency of IFN-γ-positive cells present in CD8-positive T cells was analyzed using a flow cytometer. An $eEF2_{739-747}$ peptide was used in FIG. 11, and an $eEF2_{661-669}$ peptide in FIG. 12. As a result, it was found that $eEF2_{661-669}$ (SEQ ID NO:11) and $eEF2_{739-747}$ (SEQ ID NO:8) peptides increase the interferon-γ activity (FIGS. 11 and 12).

Determination of Cytotoxic Activity

Next, evaluation was carried out as to whether the six candidate peptides [$eEF2_{739-747}$ (SEQ ID NO:8), $eEF2_{519-527}$ (SEQ ID NO:9), $eEF2_{672-679}$ (SEQ ID NO:10), $eEF2_{661-669}$ (SEQ ID NO:11), $eEF2_{394-402}$ (SEQ ID NO:12) and $eEF2_{284-292}$ (SEQ ID NO:13), excepting $eEF2_{292-300}$ (SEQ ID NO:14)] selected as described above actually have a cytotoxic activity. The experiments were carried out in much the same way as in the above Example 3. Thus, blood was taken from healthy donors having an HLA-A*0201 molecule, peripheral blood mononuclear cells were separated, and the first stimulation was carried out using the six candidate peptides (stimulator: self-PBMC). Subsequently, the peptide stimulation on the second day and later was carried out at intervals of 8 to 13 days (stimulator: allo B-LCL 3 mg/ml). Furthermore, IL-2 was added every 2 days after the second stimulation at a final concentration of 20 IU/ml. Cytotoxicity was measured on the 6th day after the final peptide stimulation. As a result, increase of cytotoxic activity was observed in the above 6 peptides (FIGS. 16 to 21). From the above fact, it was found that the above 6 peptides [$eEF2_{739-747}$ (SEQ ID NO:8), $eEF2_{519-527}$ (SEQ ID NO:9), $eEF2_{671-679}$ (SEQ ID NO:10), $eEF2_{661-669}$ (SEQ ID NO:11), $eEF2_{394-402}$ (SEQ ID NO:12) and $eEF2_{284-292}$ (SEQ ID NO:13)] bind to the HLA-A*0201 molecule and have a cytotoxic activity.

Next, evaluation was carried out as to whether the above 6 peptides and the $eEF2_{292-300}$ peptide (SEQ ID NO:14) can bind to an HLA-A*0206 molecule and produce interferon-γ. The experiments were carried out in the same way as in the above method, except that donors having the HLA-A*0206 molecule were used. As a result, it was found that all peptides tested increase the production of interferon-γ(FIG. 29).

Binding Affinity of Modified-Type EEF2 Peptides to HLA-A*0201 Molecule

Next, a binding affinity of modified-type eEF2 peptides, in which an amino acid at position 2 and/or position 9 in the above 6 peptides ($eEF2_{739-747}$, $eEF2_{519-527}$, $eEF2_{671-679}$, $eEF2_{661-669}$, $eEF2_{394-402}$ and $eEF2_{284-292}$ as well as $eEF2_{292-300}$ peptide (SEQ ID NO:14) was altered to another amino acid, was predicted using a program as described above (Tables 15 to 21).

TABLE 15

Prediction of binding affinity of modified-type (SEQ ID NOs: 32 to 34) of eEF2$_{739-747}$ peptide (SEQ ID NO: 8) to HLA-A*0201 molecule using two program (NetMHC3.0 and ProPred)

| Peptide | Amino acid sequence | NetMHC3.0 | | | ProPred | |
| --- | --- | --- | --- | --- | --- | --- |
| | | Affinity (nM) | Binding level | Log score | Real score | Log score |
| eEF2$_{739-747}$ | RLMEPIYLV | 3 | SB | 0.880 | 2426.739 | 7.7943 |
| eEF2$_{739-747}$ 2M | RMMEPIYLV (SEQ ID NO: 32) | 3 | SB | 0.897 | 1752.645 | 7.4689 |
| eEF2$_{739-747}$ 9L | RLMEPIYLL (SEQ ID NO: 33) | 4 | SB | 0.860 | 745.355 | 6.6139 |
| eEF2$_{739-747}$ 2M9L | RMMEPIYLL (SEQ ID NO: 34) | 3 | SB | 0.877 | 538.312 | 6.2884 |

TABLE 16

Prediction of binding affinity of modified-type (SEQ ID NOs: 35 to 37) of eEF2$_{519-527}$ peptide (SEQ ID NO: 9) to HLA-A*0201 molecule using two program (NetMHC3.0 and ProPred)

| Peptide | Amino acid sequence | NetMHC3.0 | | | ProPred | |
| --- | --- | --- | --- | --- | --- | --- |
| | | Affinity (nM) | Binding level | Log score | Real score | Log score |
| eEF2$_{519-527}$ | KLVEGLKRL | 289 | WB | 0.476 | 705.066 | 6.5583 |
| eEF2$_{519-527}$2M | KMVEGLKRL (SEQ ID NO: 35) | 201 | WB | 0.510 | 509.214 | 6.2329 |
| eEF2$_{519-527}$9V | KLVEGLKRV (SEQ ID NO: 36) | 178 | WB | 0.521 | 2295.564 | 7.7387 |
| eEF2$_{519-527}$2M9V | KMVEGLKRV (SEQ ID NO: 37) | 112 | WB | 0.563 | 1657.907 | 7.4133 |

TABLE 17

Prediction of binding affinity of modified-type (SEQ ID NOs: 38 to 40) of eEF2$_{671-679}$ peptide (SEQ ID NO: 10) to HLA-A*0201 molecule using two program (NetMHC3.0 and ProPred)

| Peptide | Amino acid sequence | NetMHC3.0 | | | ProPred | |
| --- | --- | --- | --- | --- | --- | --- |
| | | Affinity (nM) | Binding level | Log score | Real score | Log score |
| eEF2$_{671-679}$ | YLNEIKDSV | 11 | SB | 0.778 | 642.758 | 6.4658 |
| eEF2$_{611-679}$2M | YMNEIKDSV (SEQ ID NO: 38) | 10 | SB | 0.780 | 464.214 | 6.1403 |
| eEF2$_{671-679}$9L | YLNEIKDSL (SEQ ID NO: 39) | 20 | SB | 0.723 | 197.418 | 5.2853 |
| eEF2$_{611-679}$2M9L | YMNEIKDSL (SEQ ID NO: 40) | 21 | SB | 0.718 | 142.580 | 4.9599 |

TABLE 18

Prediction of binding affinity of modified-type (SEQ ID NOs: 41 to 43) of eEF2$_{661-669}$ peptide (SEQ ID NO: 11) to HLA-A*0201 molecule using two program (NetMHC3.0 and ProPred)

| Peptide | Amino acid sequence | NetMHC3.0 | | | ProPred | |
|---|---|---|---|---|---|---|
| | | Affinity (nM) | Binding level | Log score | Real score | Log score |
| eEF2$_{661-669}$ | ILTDITKGV | 46 | SB | 0.644 | 484.777 | 6.1837 |
| eEF2$_{661-669}$2M (SEQ ID NO: 41) | IMTDITKGV | 44 | SB | 0.649 | 350.117 | 5.8583 |
| eEF2$_{661-669}$9L (SEQ ID NO: 42) | ILTDITKGL | 82 | WB | 0.592 | 148.896 | 5.0032 |
| eEF2$_{661-669}$2M9L (SEQ ID NO: 43) | IMTDITKGL | 88 | WB | 0.585 | 107.536 | 4.6778 |

TABLE 19

Prediction of binding affinity of modified-type (SEQ ID NOs: 44 to 46) of eEF2$_{394-402}$ peptide (SEQ ID NO: 12) to HLA-A*0201 molecule using two program (NetMHC3.0 and ProPred)

| Peptide | Amino acid sequence | NetMHC3.0 | | | ProPred | |
|---|---|---|---|---|---|---|
| | | Affinity (nM) | Binding level | Log score | Real score | Log score |
| eEF2$_{394-402}$ | LMMYISKMV | 24 | SB | 0.704 | 315.959 | 5.7556 |
| eEF2$_{394-402}$2L (SEQ ID NO: 44) | LLMYISKMV | 44 | SB | 0.648 | 437.482 | 6.0810 |
| eEF2$_{394-402}$9V (SEQ ID NO: 45) | LMMYISKML | 83 | WB | 0.591 | 97.045 | 4.5752 |
| eEF2$_{394-402}$2L9L (SEQ ID NO: 46) | LLMYISKML | 139 | WB | 0.544 | 134.369 | 4.9006 |

TABLE 20

Prediction of binding affinity of modified-type (SEQ ID NOs: 47 to 49) of eEF2$_{284-292}$ peptide (SEQ ID NO: 13) to HLA-A*0201 molecule using two program (NetMHC3.0 and ProPred)

| Peptide | Amino acid sequence | NetMHC3.0 | | | ProPred | |
|---|---|---|---|---|---|---|
| | | Affinity (nM) | Binding level | Log score | Real score | Log score |
| eEF2$_{284-292}$ | KLPRTFCQL | 1145 | | 0.705 | 142.060 | 4.9562 |
| eEF2$_{284-292}$2M (SEQ ID NO: 47) | KMPRTFCQL | 983 | | 0.363 | 102.599 | 4.6308 |
| eEE2$_{284-292}$9V (SEQ ID NO: 48) | KLPRTFCQV | 331 | WB | 0.463 | 462.521 | 6.1367 |
| eEF2$_{284-292}$2M9L (SEQ ID NO: 49) | KMPRTFCQV | 228 | WB | 0.498 | 334.043 | 5.8113 |

TABLE 21

Prediction of binding affinity of modified-type (SEQ ID NOs: 15 to 17 and 24) of eEF2$_{292-300}$ peptide (SEQ ID NO: 14) to HLA-A*0201 molecule using two program (NetMHC3.0 and ProPred)

| Peptide | Amino acid sequence | NetMHC3.0 | | | ProPred | |
|---|---|---|---|---|---|---|
| | | Real score | Log score | Affinity (nm) | Binding level | Log score |
| eEF2$_{292-300}$ | LILDPIFKV | 3290.05 | 8.10 | 8 | SB | 0.802 |
| eEF2$_{292-300}$2L | LLLDPIFKV (SEQ ID NO: 15) | 23927.65 | 10.08 | 3 | SB | 0.898 |
| eEF2$_{292-300}$2M | LMLDPIFKV (SEQ ID NO: 16) | 17281.08 | 9.76 | 3 | SB | 0.898 |
| eEF2$_{292-300}$2L9L | LLLDPIFKL (SEQ ID NO: 17) | 7349.21 | 8.90 | 3 | SB | 0.872 |
| eEF2$_{292-300}$2M9L | LMLDPIFKL (SEQ ID NO: 18) | 5307.76 | 8.58 | 3 | SB | 0.872 |

In addition, on modified-type peptides (SEQ ID NOs:15 to 17 and 24) of eEF2$_{292-300}$ (SEQ ID NO:14) among the above peptides, a binding affinity to the HLA-A*0201 molecule (Table 22), cytotoxicity (FIGS. 22 to 25) and an interferon-γ activity (FIG. 26) were actually evaluated using a method as described above.

TABLE 22

Binding assay (stabilization assay) of modified-type eEF2$_{292-300}$ peptides

| Peptide | Amino acid sequence | MIF | % MIF increase |
|---|---|---|---|
| Ns | | 4.96 | |
| Non-peptide | | 84.50 | |
| eEF2$_{292-300}$ | LILDPIFKV | 311.69 | 268.86 |
| eEF2$_{292-300}$ 2L | LLLDPIFKV | 338.80 | 300.95 |
| eEF2$_{292-300}$ 2M | LMLDPIFKV | 313.14 | 270.58 |
| eEF2$_{292-300}$ 2L9L | LLLDPIFKL | 319.26 | 277.82 |
| eEF2$_{292-300}$ 2M9L | LMLDPIFKL | 275.42 | 225.94 |

As a result, it was found that, among the modified-type eEF2$_{292-300}$ peptides, eEF2$_{292-300}$ 2L (a peptide having alteration of from I to L in an amino acid at position 2 in the eEF2$_{292-300}$ peptide, SEQ ID NO:15), eEF2$_{292-300}$ 2M (a peptide having alteration of from I to M in an amino acid at position 2 in the eEF2$_{292-300}$ peptide, SEQ ID NO:16), eEF2$_{292-300}$ 2L9L (a peptide having alteration of from I to L in an amino acid at position 2 and of from V to L in an amino acid at position 9 in the eEF2$_{292-300}$ peptide, SEQ ID NO:17) and eEF2$_{292-300}$ 2M9L (a peptide having alteration of from I to M in an amino acid at position 2 and of from V to L in an amino acid at position 9 in the eEF2$_{292-300}$ peptide, SEQ ID NO:24) have a binding affinity to the HLA-A*0201 molecule higher than that of the original eEF2$_{292-300}$ peptide (Table 22), and increase cytotoxicity and interferon-γ activity in human (FIGS. 22 to 26, and 28).

Example 5

Forced Expression of EEF2 in Cancer Cell Line

Cell clones were established in which an eEF2 expression vector or a vacant expression vector was expressed in stomach cancer cell line AZ-521. The eEF2 expression vector is one in which a nucleotide sequence of an eEF2 gene is inserted into a restriction enzyme cleavage site: EcoRI of pcDNA3.1 (+) (Invitrogen). These cells were cultured without synchronization, and doubling time of the cells was calculated from cell counts after 48 and 72 hours from the beginning of culture. Furthermore, 1×10$^5$ cells were fixed with 80% ethanol and then allowed to stand in PBS containing propidium iodide (PI, 5 μg/ml) and RNaseA (200 μg/ml) for 30 minutes, and distribution of each phase of cell cycle was analyzed by flow cytometry (FIG. 13, left upper graph). Since the doubling time of cells corresponds to length of the cell cycle, the time was then multiplied by proportional distribution of each phase of cell cycle to calculate progression time of each phase (FIG. 13, right upper graph and lower table). As a result, it was observed that the cell count in a G2/M phase decreases and the progression time is shortened in cells having eEF2 expressed (FIG. 13). This suggests that the eEF2 accelerates progression of the G2/M phase.

Each of 5×10$^6$ cells of stomach cancer cell line AZ-521 having eEF2 forcibly expressed (2 clones) and AZ-521 having a control vacant vector expressed (2 clones) established as described above was mixed with Matrigel (Becton Dickinson), and the mixture was subcutaneously injected into left and right abdominal regions of nude mice to form a tumor. The size of the tumor was measured twice a week, and observed for 34 days. Volume (mm$^3$) of the tumor was calculated by (minor axis)$^2$×(major axis)$^2$/2. The results of three experiments carried out separately on each clone are shown (FIG. 14). From the results, it was shown that the volume of the tumor remarkably increases in mice injected with cells having eEF2 forcibly expressed as compared with a control. FIG. 15 shows a typical example. The left tumor is caused by AZ-521 cells having a vacant vector expressed, and the right tumor by AZ-521 cells having eEF2 forcibly expressed.

Example 6

Identification of Novel Target Sequence of ShRNA Targeting at EEF2

In order to develop an shRNA (hereinafter, referred to as shEF2) which can efficiently inhibit expression of eEF2 by targeting at the eEF2 and inhibit growth of cancer, two sequences (hereinafter, referred to as shEF-1918 and shEF-2804) were newly selected which can be targets in an eEF2 sequence.

A target sequence at positions 1918-1947 (positions 1918-1947 from the 5' end of a DNA sequence encoding an eEF2 protein) in an eEF2 gene: 5'-gcc tggccgagga catcgataaa ggcgagg-3' (SEQ ID NO:18).

A target sequence at positions 2804-2833 (positions 2804-2833 from the 5' end of a DNA sequence encoding an eEF2 protein) in an eEF2 gene: 5'-actcaac cataacactt gatgccgttt ctt-3' (SEQ ID NO:19).

Construction of ShRNA

In order to construct an shRNA for the above sequences (SEQ ID NOs:18 and 19), a DNA sequence [shEF-1918 or shEF-2804 (sense strand)] consisting of a sense sequence of a target sequence (30 bases)–a loop sequence (10 bases)–an antisense sequence (30 bases), and its complementary DNA sequence [shEF-1918 or shEF-2804 (antisense strand)] were chemically synthesized and then annealed, and the product was inserted into SacI and KpnI recognition sites of tRNA-shRNA expression vector, piGENE tRNA Pur (Clontech, Palo Alto, Calif.). Such DNA sequences inserted are shown below. In this connection, variations were added to a portion of a sense sequence of a target sequence so that an antisense strand is efficiently taken into RISC when an RNA having a sequence transcribed is cleaved (shown by underlines in the following sequences).

shEF-1918 (sense strand):
(SEQ ID NO: 20)
5'-(gcc tggccgagga catcgatgaa agcgtgg) cttcctgtca (cctcgcc tttatcgatg tcctcggcca ggc)-3' shEF-1918 (antisense strand):
(SEQ ID NO: 21)
3'-(cgg accggctcct gtagctactt tcgcacc) gaaggacagt (ggagcgg aaatagctac aggagccggt ccg)-5' shEF-2804 (sense strand):
(SEQ ID NO: 22)
5'-(actcaac cataacactt gataccattt gtt) cttcctgtca (aagaaacggcatc aagtgttatg gttgagt)-3' shEF-2804 (antisense strand):
(SEQ ID NO: 23)
3'-(tgagttg gtattgtgaa ctatggtaaa caa) gaaggacagt (ttctttgccgtag ttcacaatac caactca)-5'

Cell Culture and Introduction of ShRNA

Lung cancer cell PC-14, pancreatic cancer cell PCI6, fibrosarcoma cell HT-1080 and malignant glioma cell A172 were cultured in DMEM containing 10% FBS. In order to introduce an shRNA, cells ($1 \times 10^5$) were washed twice with PBS and then suspended in 250 μL of an FBS-free RPMI1640 medium, each 10 μg of shEF-1918, shEF-2804, or a shRNA vector for Luciferase, shLuc dissolved in 50 μL of an FBS-free RPMI1640 medium was added to the suspension, and electroporation was carried out using Gene Pulsor II (BioRad) under a condition of 950 μFD and 175 V. Survival rate of cells was about 90% under this condition. After the introduction of the shRNA, the number of living cells was counted, the cells were seeded at a density of $1 \times 10^5$ cells/mL, trypsin treatment was carried out after 72 hours, and the number of cells was counted. As a result, shEF-1918 and shEF-2804 significantly inhibited cell proliferation in all four types of cells analyzed as compared with shLuc (FIG. 27).

INDUSTRIAL APPLICABILITY

The present invention provides a method for detecting cancer using eEF2 as a marker, a pharmaceutical composition for treatment or prevention targeting at eEF2, an HLA-A*2402-restricted or HLA-A*0201-restricted eEF2 peptide, a pharmaceutical composition containing them, and others, and is therefore applicable in the field of pharmaceuticals, for example, in the field of development and production of preventive or therapeutic pharmaceuticals for various hematopoietic organ tumors or solid cancers highly expressing an eEF2 gene.

Sequence Listing Free Text
SEQ ID NO:2: eEF2 siRNA
SEQ ID NO:3: eEF2 siRNA
SEQ ID NO:18: eEF2 1918-1947
SEQ ID NO:19: eEF2 2804-2833
SEQ ID NO:20: shEF-1918 sense
SEQ ID NO:21: shEF-1918 antisense
SEQ ID NO:22: shEF-2804 sense
SEQ ID NO:23: shEF-2804 antisense
Sequence Listing

---

The invention claimed is:

1. A method for the treatment of a cancer in an HLA-A*0201-positive subject, comprising administering to said subject an effective amount of an eEF2 peptide consisting of an amino acid sequence composed of contiguous amino acids of an eEF2 protein, wherein the amino acid sequence is selected from the group consisting of:
   (a) Leu Ile Leu Asp Pro Ile Phe Lys Val (SEQ ID NO:14); and
   (b) the amino acid sequence of SEQ ID NO: 14 having a substitution or substitutions of the amino acid Ile at position 2 with Leu or Met and/or a substitution of the amino acid Val at position 9 with Leu, wherein the eEF2 peptide retains a binding ability to the HLA-A*0201 molecule.

2. The method for the treatment of a cancer according to claim 1, wherein the amino acid sequence has, in the Leu Ile Leu Asp Pro Ile Phe Lys Val (SEQ ID NO:14), a substitution of the amino acid Ile at position 2 with Leu or Met, and/or a substitution of the amino acid Val at position 9 with Leu.

3. The method for the treatment of a cancer according to any one of claims 1 or 2, wherein the composition includes a further anticancer drug.

4. The method according to any one of claims 1 or 2, wherein the cancer is chosen from the group of lung adenocarcinoma, small-cell lung cancer, esophageal cancer, stomach cancer, colon cancer, pancreatic duct cancer, malignant glioblastoma, malignant lymphoma and head-and-neck squamous cell cancer.

5. The method according to claim 3, wherein the cancer is chosen from the group of lung adenocarcinoma, small-cell lung cancer, esophageal cancer, stomach cancer, colon cancer, pancreatic duct cancer, malignant glioblastoma, malignant lymphoma and head-and-neck squamous cell cancer.

* * * * *

SEQUENCE LISTING

<160> NUMBER OF SEQ ID NOS: 141

<210> SEQ ID NO 1
<211> LENGTH: 858
<212> TYPE: PRT
<213> ORGANISM: Homo sapiens

<400> SEQUENCE: 1

Met Val Asn Phe Thr Val Asp Gln Ile Arg Ala Ile Met Asp Lys Lys
1               5                   10                  15

Ala Asn Ile Arg Asn Met Ser Val Ile Ala His Val Asp His Gly Lys
            20                  25                  30

```
Ser Thr Leu Thr Asp Ser Leu Val Cys Lys Ala Gly Ile Ala Ser
        35              40              45
Ala Arg Ala Gly Glu Thr Arg Phe Thr Asp Thr Arg Lys Asp Glu Gln
 50              55              60
Glu Arg Cys Ile Thr Ile Lys Ser Thr Ala Ile Ser Leu Phe Tyr Glu
 65              70              75              80
Leu Ser Glu Asn Asp Leu Asn Phe Ile Lys Gln Ser Lys Asp Gly Ala
                85              90              95
Gly Phe Leu Ile Asn Leu Ile Asp Ser Pro Gly His Val Asp Phe Ser
                100             105             110
Ser Glu Val Thr Ala Ala Leu Arg Val Thr Asp Gly Ala Leu Val Val
        115             120             125
Val Asp Cys Val Ser Gly Val Cys Val Gln Thr Glu Thr Val Leu Arg
130             135             140
Gln Ala Ile Ala Glu Arg Ile Lys Pro Val Leu Met Met Asn Lys Met
145             150             155             160
Asp Arg Ala Leu Leu Glu Leu Gln Leu Glu Pro Glu Glu Leu Tyr Gln
                165             170             175
Thr Phe Gln Arg Ile Val Glu Asn Val Asn Val Ile Ile Ser Thr Tyr
                180             185             190
Gly Glu Gly Glu Ser Gly Pro Met Gly Asn Ile Met Ile Asp Pro Val
        195             200             205
Leu Gly Thr Val Gly Phe Gly Ser Gly Leu His Gly Trp Ala Phe Thr
        210             215             220
Leu Lys Gln Phe Ala Glu Met Tyr Val Ala Lys Phe Ala Ala Lys Gly
225             230             235             240
Glu Gly Gln Leu Gly Pro Ala Glu Arg Ala Lys Lys Val Glu Asp Met
                245             250             255
Met Lys Lys Leu Trp Gly Asp Arg Tyr Phe Asp Pro Ala Asn Gly Lys
                260             265             270
Phe Ser Lys Ser Ala Thr Ser Pro Glu Gly Lys Lys Leu Pro Arg Thr
        275             280             285
Phe Cys Gln Leu Ile Leu Asp Pro Ile Phe Lys Val Phe Asp Ala Ile
        290             295             300
Met Asn Phe Lys Lys Glu Glu Thr Ala Lys Leu Ile Glu Lys Leu Asp
305             310             315             320
Ile Lys Leu Asp Ser Glu Asp Lys Asp Lys Glu Gly Lys Pro Leu Leu
                325             330             335
Lys Ala Val Met Arg Arg Trp Leu Pro Ala Gly Asp Ala Leu Leu Gln
                340             345             350
Met Ile Thr Ile His Leu Pro Ser Pro Val Thr Ala Gln Lys Tyr Arg
        355             360             365
Cys Glu Leu Leu Tyr Glu Gly Pro Pro Asp Asp Glu Ala Ala Met Gly
370             375             380
Ile Lys Ser Cys Asp Pro Lys Gly Pro Leu Met Met Tyr Ile Ser Lys
385             390             395             400
Met Val Pro Thr Ser Asp Lys Gly Arg Phe Tyr Ala Phe Gly Arg Val
                405             410             415
Phe Ser Gly Leu Val Ser Thr Gly Leu Lys Val Arg Ile Met Gly Pro
        420             425             430
Asn Tyr Thr Pro Gly Lys Lys Glu Asp Leu Tyr Leu Lys Pro Ile Gln
        435             440             445
Arg Thr Ile Leu Met Met Gly Arg Tyr Val Glu Pro Ile Glu Asp Val
```

```
                    450                 455                 460
        Pro Cys Gly Asn Ile Val Gly Leu Val Gly Val Asp Gln Phe Leu Val
        465                 470                 475                 480

Lys Thr Gly Thr Ile Thr Thr Phe Glu His Ala His Asn Met Arg Val
                            485                 490                 495

Met Lys Phe Ser Val Ser Pro Val Val Arg Val Ala Val Glu Ala Lys
                        500                 505                 510

Asn Pro Ala Asp Leu Pro Lys Leu Val Glu Gly Leu Lys Arg Leu Ala
                        515                 520                 525

Lys Ser Asp Pro Met Val Gln Cys Ile Ile Glu Glu Ser Gly Glu His
                    530                 535                 540

Ile Ile Ala Gly Ala Gly Glu Leu His Leu Glu Ile Cys Leu Lys Asp
        545                 550                 555                 560

Leu Glu Glu Asp His Ala Cys Ile Pro Ile Lys Lys Ser Asp Pro Val
                            565                 570                 575

Val Ser Tyr Arg Glu Thr Val Ser Glu Glu Ser Asn Val Leu Cys Leu
                        580                 585                 590

Ser Lys Ser Pro Asn Lys His Asn Arg Leu Tyr Met Lys Ala Arg Pro
                        595                 600                 605

Phe Pro Asp Gly Leu Ala Glu Asp Ile Asp Lys Gly Glu Val Ser Ala
                    610                 615                 620

Arg Gln Glu Leu Lys Gln Arg Ala Arg Tyr Leu Ala Glu Lys Tyr Glu
        625                 630                 635                 640

Trp Asp Val Ala Glu Ala Arg Lys Ile Trp Cys Phe Gly Pro Asp Gly
                            645                 650                 655

Thr Gly Pro Asn Ile Leu Thr Asp Ile Thr Lys Gly Val Gln Tyr Leu
                        660                 665                 670

Asn Glu Ile Lys Asp Ser Val Val Ala Gly Phe Gln Trp Ala Thr Lys
                        675                 680                 685

Glu Gly Ala Leu Cys Glu Glu Asn Met Arg Gly Val Arg Phe Asp Val
                    690                 695                 700

His Asp Val Thr Leu His Ala Asp Ala Ile His Arg Gly Gly Gly Gln
        705                 710                 715                 720

Ile Ile Pro Thr Ala Arg Arg Cys Leu Tyr Ala Ser Val Leu Thr Ala
                            725                 730                 735

Gln Pro Arg Leu Met Glu Pro Ile Tyr Leu Val Glu Ile Gln Cys Pro
                        740                 745                 750

Glu Gln Val Val Gly Gly Ile Tyr Gly Val Leu Asn Arg Lys Arg Gly
                        755                 760                 765

His Val Phe Glu Glu Ser Gln Val Ala Gly Thr Pro Met Phe Val Val
                    770                 775                 780

Lys Ala Tyr Leu Pro Val Asn Glu Ser Phe Gly Phe Thr Ala Asp Leu
        785                 790                 795                 800

Arg Ser Asn Thr Gly Gly Gln Ala Phe Pro Gln Cys Val Phe Asp His
                            805                 810                 815

Trp Gln Ile Leu Pro Gly Asp Pro Phe Asp Asn Ser Ser Arg Pro Ser
                        820                 825                 830

Gln Val Val Ala Glu Thr Arg Lys Arg Lys Gly Leu Lys Glu Gly Ile
                        835                 840                 845

Pro Ala Leu Asp Asn Phe Leu Asp Lys Leu
            850                 855

<210> SEQ ID NO 2
```

```
<211> LENGTH: 30
<212> TYPE: RNA
<213> ORGANISM: Artificial Sequence
<220> FEATURE:
<223> OTHER INFORMATION: eEF2 siRNA

<400> SEQUENCE: 2
caugggcaac aucaugaucg auccuguccu                                        30

<210> SEQ ID NO 3
<211> LENGTH: 30
<212> TYPE: RNA
<213> ORGANISM: Artificial Sequence
<220> FEATURE:
<223> OTHER INFORMATION: eEF2 siRNA

<400> SEQUENCE: 3
aggacaggau cgaucaugau guugcccaug                                        30

<210> SEQ ID NO 4
<211> LENGTH: 9
<212> TYPE: PRT
<213> ORGANISM: Homo sapiens

<400> SEQUENCE: 4

Arg Phe Tyr Ala Phe Gly Arg Val Phe
1               5

<210> SEQ ID NO 5
<211> LENGTH: 9
<212> TYPE: PRT
<213> ORGANISM: Homo sapiens

<400> SEQUENCE: 5

Ala Phe Gly Arg Val Phe Ser Gly Leu
1               5

<210> SEQ ID NO 6
<211> LENGTH: 9
<212> TYPE: PRT
<213> ORGANISM: Homo sapiens

<400> SEQUENCE: 6

Arg Phe Asp Val His Asp Val Thr Leu
1               5

<210> SEQ ID NO 7
<211> LENGTH: 9
<212> TYPE: PRT
<213> ORGANISM: Homo sapiens

<400> SEQUENCE: 7

Ala Tyr Leu Pro Val Asn Glu Ser Phe
1               5

<210> SEQ ID NO 8
<211> LENGTH: 9
<212> TYPE: PRT
<213> ORGANISM: Homo sapiens

<400> SEQUENCE: 8

Arg Leu Met Glu Pro Ile Tyr Leu Val
1               5

<210> SEQ ID NO 9
```

```
<211> LENGTH: 9
<212> TYPE: PRT
<213> ORGANISM: Homo sapiens

<400> SEQUENCE: 9

Lys Leu Val Glu Gly Leu Lys Arg Leu
1               5

<210> SEQ ID NO 10
<211> LENGTH: 9
<212> TYPE: PRT
<213> ORGANISM: Homo sapiens

<400> SEQUENCE: 10

Tyr Leu Asn Glu Ile Lys Asp Ser Val
1               5

<210> SEQ ID NO 11
<211> LENGTH: 9
<212> TYPE: PRT
<213> ORGANISM: Homo sapiens

<400> SEQUENCE: 11

Ile Leu Thr Asp Ile Thr Lys Gly Val
1               5

<210> SEQ ID NO 12
<211> LENGTH: 9
<212> TYPE: PRT
<213> ORGANISM: Homo sapiens

<400> SEQUENCE: 12

Leu Met Met Tyr Ile Ser Lys Met Val
1               5

<210> SEQ ID NO 13
<211> LENGTH: 9
<212> TYPE: PRT
<213> ORGANISM: Homo sapiens

<400> SEQUENCE: 13

Lys Leu Pro Arg Thr Phe Cys Gln Leu
1               5

<210> SEQ ID NO 14
<211> LENGTH: 9
<212> TYPE: PRT
<213> ORGANISM: Homo sapiens

<400> SEQUENCE: 14

Leu Ile Leu Asp Pro Ile Phe Lys Val
1               5

<210> SEQ ID NO 15
<211> LENGTH: 9
<212> TYPE: PRT
<213> ORGANISM: Homo sapiens

<400> SEQUENCE: 15

Leu Leu Leu Asp Pro Ile Phe Lys Val
1               5

<210> SEQ ID NO 16
<211> LENGTH: 9
<212> TYPE: PRT
```

<213> ORGANISM: Homo sapiens

<400> SEQUENCE: 16

Leu Met Leu Asp Pro Ile Phe Lys Val
1               5

<210> SEQ ID NO 17
<211> LENGTH: 9
<212> TYPE: PRT
<213> ORGANISM: Homo sapiens

<400> SEQUENCE: 17

Leu Leu Leu Asp Pro Ile Phe Lys Leu
1               5

<210> SEQ ID NO 18
<211> LENGTH: 30
<212> TYPE: DNA
<213> ORGANISM: Artificial Sequence
<220> FEATURE:
<223> OTHER INFORMATION: eEF2 1918-1947

<400> SEQUENCE: 18
gcctggccga ggacatcgat aaaggcgagg                                       30

<210> SEQ ID NO 19
<211> LENGTH: 30
<212> TYPE: DNA
<213> ORGANISM: Artificial Sequence
<220> FEATURE:
<223> OTHER INFORMATION: eEF2 2804-2833

<400> SEQUENCE: 19
actcaaccat aacacttgat gccgtttctt                                       30

<210> SEQ ID NO 20
<211> LENGTH: 70
<212> TYPE: DNA
<213> ORGANISM: Artificial Sequence
<220> FEATURE:
<223> OTHER INFORMATION: shEF-1918 sense

<400> SEQUENCE: 20
gcctggccga ggacatcgat gaaagcgtgg cttcctgtca cctcgccttt atcgatgtcc      60
tcggccaggc                                                             70

<210> SEQ ID NO 21
<211> LENGTH: 70
<212> TYPE: DNA
<213> ORGANISM: Artificial Sequence
<220> FEATURE:
<223> OTHER INFORMATION: shEF-1918 antisense

<400> SEQUENCE: 21
gcctggccga ggacatcgat aaaggcgagg tgacaggaag ccacgctttc atcgatgtcc      60
tcggccaggc                                                             70

<210> SEQ ID NO 22
<211> LENGTH: 70
<212> TYPE: DNA
<213> ORGANISM: Artificial Sequence
<220> FEATURE:
<223> OTHER INFORMATION: shEF-2804 sense

<400> SEQUENCE: 22

-continued

```
actcaaccat aacacttgat accatttgtt cttcctgtca agaaacggc atcaagtgtt      60 atggttgagt                                                            70
```

<210> SEQ ID NO 23
<211> LENGTH: 70
<212> TYPE: DNA
<213> ORGANISM: Artificial Sequence
<220> FEATURE:
<223> OTHER INFORMATION: shEF-2804 antisense

<400> SEQUENCE: 23

```
actcaaccat aacacttgat gccgtttctt tgacaggaag aacaaatggt atcaagtgtt     60
atggttgagt                                                            70
```

<210> SEQ ID NO 24
<211> LENGTH: 9
<212> TYPE: PRT
<213> ORGANISM: Homo sapiens

<400> SEQUENCE: 24

```
Leu Met Leu Asp Pro Ile Phe Lys Leu
1               5
```

<210> SEQ ID NO 25
<211> LENGTH: 9
<212> TYPE: PRT
<213> ORGANISM: Homo sapiens

<400> SEQUENCE: 25

```
Ala Tyr Leu Pro Val Asn Glu Ser Ile
1               5
```

<210> SEQ ID NO 26
<211> LENGTH: 9
<212> TYPE: PRT
<213> ORGANISM: Homo sapiens

<400> SEQUENCE: 26

```
Ala Tyr Leu Pro Val Asn Glu Ser Leu
1               5
```

<210> SEQ ID NO 27
<211> LENGTH: 9
<212> TYPE: PRT
<213> ORGANISM: Homo sapiens

<400> SEQUENCE: 27

```
Arg Tyr Tyr Ala Phe Gly Arg Val Phe
1               5
```

<210> SEQ ID NO 28
<211> LENGTH: 9
<212> TYPE: PRT
<213> ORGANISM: Homo sapiens

<400> SEQUENCE: 28

```
Arg Phe Tyr Ala Phe Gly Arg Val Ile
1               5
```

<210> SEQ ID NO 29
<211> LENGTH: 9
<212> TYPE: PRT
<213> ORGANISM: Homo sapiens

<400> SEQUENCE: 29

Arg Tyr Tyr Ala Phe Gly Arg Val Ile
1               5

<210> SEQ ID NO 30
<211> LENGTH: 9
<212> TYPE: PRT
<213> ORGANISM: Homo sapiens

<400> SEQUENCE: 30

Arg Phe Tyr Ala Phe Gly Arg Val Leu
1               5

<210> SEQ ID NO 31
<211> LENGTH: 9
<212> TYPE: PRT
<213> ORGANISM: Homo sapiens

<400> SEQUENCE: 31

Arg Tyr Tyr Ala Phe Gly Arg Val Leu
1               5

<210> SEQ ID NO 32
<211> LENGTH: 9
<212> TYPE: PRT
<213> ORGANISM: Homo sapiens

<400> SEQUENCE: 32

Arg Met Met Glu Pro Ile Tyr Leu Val
1               5

<210> SEQ ID NO 33
<211> LENGTH: 9
<212> TYPE: PRT
<213> ORGANISM: Homo sapiens

<400> SEQUENCE: 33

Arg Leu Met Glu Pro Ile Tyr Leu Leu
1               5

<210> SEQ ID NO 34
<211> LENGTH: 9
<212> TYPE: PRT
<213> ORGANISM: Homo sapiens

<400> SEQUENCE: 34

Arg Met Met Glu Pro Ile Tyr Leu Leu
1               5

<210> SEQ ID NO 35
<211> LENGTH: 9
<212> TYPE: PRT
<213> ORGANISM: Homo sapiens

<400> SEQUENCE: 35

Lys Met Val Glu Gly Leu Lys Arg Leu
1               5

<210> SEQ ID NO 36
<211> LENGTH: 9
<212> TYPE: PRT
<213> ORGANISM: Homo sapiens

<400> SEQUENCE: 36

```
Lys Leu Val Glu Gly Leu Lys Arg Val
1               5

<210> SEQ ID NO 37
<211> LENGTH: 9
<212> TYPE: PRT
<213> ORGANISM: Homo sapiens

<400> SEQUENCE: 37

Lys Met Val Glu Gly Leu Lys Arg Val
1               5

<210> SEQ ID NO 38
<211> LENGTH: 9
<212> TYPE: PRT
<213> ORGANISM: Homo sapiens

<400> SEQUENCE: 38

Tyr Met Asn Glu Ile Lys Asp Ser Val
1               5

<210> SEQ ID NO 39
<211> LENGTH: 9
<212> TYPE: PRT
<213> ORGANISM: Homo sapiens

<400> SEQUENCE: 39

Tyr Leu Asn Glu Ile Lys Asp Ser Leu
1               5

<210> SEQ ID NO 40
<211> LENGTH: 9
<212> TYPE: PRT
<213> ORGANISM: Homo sapiens

<400> SEQUENCE: 40

Tyr Met Asn Glu Ile Lys Asp Ser Leu
1               5

<210> SEQ ID NO 41
<211> LENGTH: 9
<212> TYPE: PRT
<213> ORGANISM: Homo sapiens

<400> SEQUENCE: 41

Ile Met Thr Asp Ile Thr Lys Gly Val
1               5

<210> SEQ ID NO 42
<211> LENGTH: 9
<212> TYPE: PRT
<213> ORGANISM: Homo sapiens

<400> SEQUENCE: 42

Ile Leu Thr Asp Ile Thr Lys Gly Leu
1               5

<210> SEQ ID NO 43
<211> LENGTH: 9
<212> TYPE: PRT
<213> ORGANISM: Homo sapiens

<400> SEQUENCE: 43

Ile Met Thr Asp Ile Thr Lys Gly Leu
```

```
<210> SEQ ID NO 44
<211> LENGTH: 9
<212> TYPE: PRT
<213> ORGANISM: Homo sapiens

<400> SEQUENCE: 44

Leu Leu Met Tyr Ile Ser Lys Met Val
1               5

<210> SEQ ID NO 45
<211> LENGTH: 9
<212> TYPE: PRT
<213> ORGANISM: Homo sapiens

<400> SEQUENCE: 45

Leu Met Met Tyr Ile Ser Lys Met Leu
1               5

<210> SEQ ID NO 46
<211> LENGTH: 9
<212> TYPE: PRT
<213> ORGANISM: Homo sapiens

<400> SEQUENCE: 46

Leu Leu Met Tyr Ile Ser Lys Met Leu
1               5

<210> SEQ ID NO 47
<211> LENGTH: 9
<212> TYPE: PRT
<213> ORGANISM: Homo sapiens

<400> SEQUENCE: 47

Lys Met Pro Arg Thr Phe Cys Gln Leu
1               5

<210> SEQ ID NO 48
<211> LENGTH: 9
<212> TYPE: PRT
<213> ORGANISM: Homo sapiens

<400> SEQUENCE: 48

Lys Leu Pro Arg Thr Phe Cys Gln Val
1               5

<210> SEQ ID NO 49
<211> LENGTH: 9
<212> TYPE: PRT
<213> ORGANISM: Homo sapiens

<400> SEQUENCE: 49

Lys Met Pro Arg Thr Phe Cys Gln Val
1               5

<210> SEQ ID NO 50
<211> LENGTH: 9
<212> TYPE: PRT
<213> ORGANISM: Homo sapiens

<400> SEQUENCE: 50

Gly Leu His Gly Trp Ala Phe Thr Leu
1               5
```

```
<210> SEQ ID NO 51
<211> LENGTH: 9
<212> TYPE: PRT
<213> ORGANISM: Homo sapiens

<400> SEQUENCE: 51

Gly Leu Val Gly Val Asp Gln Phe Leu
1               5

<210> SEQ ID NO 52
<211> LENGTH: 9
<212> TYPE: PRT
<213> ORGANISM: Homo sapiens

<400> SEQUENCE: 52

Trp Leu Pro Ala Gly Asp Ala Leu Leu
1               5

<210> SEQ ID NO 53
<211> LENGTH: 9
<212> TYPE: PRT
<213> ORGANISM: Homo sapiens

<400> SEQUENCE: 53

Val Val Val Asp Cys Val Ser Gly Val
1               5

<210> SEQ ID NO 54
<211> LENGTH: 9
<212> TYPE: PRT
<213> ORGANISM: Homo sapiens

<400> SEQUENCE: 54

Ala Ile Ala Glu Arg Ile Lys Pro Val
1               5

<210> SEQ ID NO 55
<211> LENGTH: 9
<212> TYPE: PRT
<213> ORGANISM: Homo sapiens

<400> SEQUENCE: 55

Ile Met Ile Asp Pro Val Leu Gly Thr
1               5

<210> SEQ ID NO 56
<211> LENGTH: 9
<212> TYPE: PRT
<213> ORGANISM: Homo sapiens

<400> SEQUENCE: 56

Arg Leu Ala Lys Ser Asp Pro Met Val
1               5

<210> SEQ ID NO 57
<211> LENGTH: 9
<212> TYPE: PRT
<213> ORGANISM: Homo sapiens

<400> SEQUENCE: 57

Gly Leu Val Ser Thr Gly Leu Lys Val
1               5

<210> SEQ ID NO 58
```

```
<211> LENGTH: 9
<212> TYPE: PRT
<213> ORGANISM: Homo sapiens

<400> SEQUENCE: 58

Leu Val Gly Val Asp Gln Phe Leu Val
1               5

<210> SEQ ID NO 59
<211> LENGTH: 9
<212> TYPE: PRT
<213> ORGANISM: Homo sapiens

<400> SEQUENCE: 59

Lys Met Asp Arg Ala Leu Leu Glu Leu
1               5

<210> SEQ ID NO 60
<211> LENGTH: 9
<212> TYPE: PRT
<213> ORGANISM: Homo sapiens

<400> SEQUENCE: 60

Phe Val Val Lys Ala Tyr Leu Pro Val
1               5

<210> SEQ ID NO 61
<211> LENGTH: 9
<212> TYPE: PRT
<213> ORGANISM: Homo sapiens

<400> SEQUENCE: 61

Thr Ile Leu Met Met Gly Arg Tyr Val
1               5

<210> SEQ ID NO 62
<211> LENGTH: 9
<212> TYPE: PRT
<213> ORGANISM: Homo sapiens

<400> SEQUENCE: 62

Asn Leu Ile Asp Ser Pro Gly His Val
1               5

<210> SEQ ID NO 63
<211> LENGTH: 9
<212> TYPE: PRT
<213> ORGANISM: Homo sapiens

<400> SEQUENCE: 63

Ala Leu Asp Asn Phe Leu Asp Lys Leu
1               5

<210> SEQ ID NO 64
<211> LENGTH: 9
<212> TYPE: PRT
<213> ORGANISM: Homo sapiens

<400> SEQUENCE: 64

Cys Leu Tyr Ala Ser Val Leu Thr Ala
1               5

<210> SEQ ID NO 65
<211> LENGTH: 9
<212> TYPE: PRT
```

```
<213> ORGANISM: Homo sapiens

<400> SEQUENCE: 65

Leu Leu Gln Met Ile Thr Ile His Leu
1               5

<210> SEQ ID NO 66
<211> LENGTH: 9
<212> TYPE: PRT
<213> ORGANISM: Homo sapiens

<400> SEQUENCE: 66

Gln Val Ala Gly Thr Pro Met Phe Val
1               5

<210> SEQ ID NO 67
<211> LENGTH: 9
<212> TYPE: PRT
<213> ORGANISM: Homo sapiens

<400> SEQUENCE: 67

Val Val Ala Gly Phe Gln Trp Ala Thr
1               5

<210> SEQ ID NO 68
<211> LENGTH: 9
<212> TYPE: PRT
<213> ORGANISM: Homo sapiens

<400> SEQUENCE: 68

Leu Met Met Asn Lys Met Asp Arg Ala
1               5

<210> SEQ ID NO 69
<211> LENGTH: 9
<212> TYPE: PRT
<213> ORGANISM: Homo sapiens

<400> SEQUENCE: 69

Asn Met Arg Gly Val Arg Phe Asp Val
1               5

<210> SEQ ID NO 70
<211> LENGTH: 9
<212> TYPE: PRT
<213> ORGANISM: Homo sapiens

<400> SEQUENCE: 70

Asn Met Arg Val Met Lys Phe Ser Val
1               5

<210> SEQ ID NO 71
<211> LENGTH: 9
<212> TYPE: PRT
<213> ORGANISM: Homo sapiens

<400> SEQUENCE: 71

Ala Ile Met Asp Lys Lys Ala Asn Ile
1               5

<210> SEQ ID NO 72
<211> LENGTH: 9
<212> TYPE: PRT
<213> ORGANISM: Homo sapiens
```

```
<400> SEQUENCE: 72

Cys Val Phe Asp His Trp Gln Ile Leu
1               5

<210> SEQ ID NO 73
<211> LENGTH: 9
<212> TYPE: PRT
<213> ORGANISM: Homo sapiens

<400> SEQUENCE: 73

Gly Ile Pro Ala Leu Asp Asn Phe Leu
1               5

<210> SEQ ID NO 74
<211> LENGTH: 9
<212> TYPE: PRT
<213> ORGANISM: Homo sapiens

<400> SEQUENCE: 74

Val Leu Asn Arg Lys Arg Gly His Val
1               5

<210> SEQ ID NO 75
<211> LENGTH: 9
<212> TYPE: PRT
<213> ORGANISM: Homo sapiens

<400> SEQUENCE: 75

Met Met Gly Arg Tyr Val Glu Pro Ile
1               5

<210> SEQ ID NO 76
<211> LENGTH: 9
<212> TYPE: PRT
<213> ORGANISM: Homo sapiens

<400> SEQUENCE: 76

Phe Leu Val Lys Thr Gly Thr Ile Thr
1               5

<210> SEQ ID NO 77
<211> LENGTH: 9
<212> TYPE: PRT
<213> ORGANISM: Homo sapiens

<400> SEQUENCE: 77

Gln Val Val Gly Gly Ile Tyr Gly Val
1               5

<210> SEQ ID NO 78
<211> LENGTH: 9
<212> TYPE: PRT
<213> ORGANISM: Homo sapiens

<400> SEQUENCE: 78

Arg Val Thr Asp Gly Ala Leu Val Val
1               5

<210> SEQ ID NO 79
<211> LENGTH: 9
<212> TYPE: PRT
<213> ORGANISM: Homo sapiens

<400> SEQUENCE: 79
```

Phe Gln Trp Ala Thr Lys Glu Gly Ala
1               5

<210> SEQ ID NO 80
<211> LENGTH: 9
<212> TYPE: PRT
<213> ORGANISM: Homo sapiens

<400> SEQUENCE: 80

Val Ala Gly Thr Pro Met Phe Val Val
1               5

<210> SEQ ID NO 81
<211> LENGTH: 9
<212> TYPE: PRT
<213> ORGANISM: Homo sapiens

<400> SEQUENCE: 81

Gly Leu Lys Glu Gly Ile Pro Ala Leu
1               5

<210> SEQ ID NO 82
<211> LENGTH: 9
<212> TYPE: PRT
<213> ORGANISM: Homo sapiens

<400> SEQUENCE: 82

Ser Val Leu Thr Ala Gln Pro Arg Leu
1               5

<210> SEQ ID NO 83
<211> LENGTH: 9
<212> TYPE: PRT
<213> ORGANISM: Homo sapiens

<400> SEQUENCE: 83

Pro Met Phe Val Val Lys Ala Tyr Leu
1               5

<210> SEQ ID NO 84
<211> LENGTH: 9
<212> TYPE: PRT
<213> ORGANISM: Homo sapiens

<400> SEQUENCE: 84

Val Met Lys Phe Ser Val Ser Pro Val
1               5

<210> SEQ ID NO 85
<211> LENGTH: 9
<212> TYPE: PRT
<213> ORGANISM: Homo sapiens

<400> SEQUENCE: 85

Trp Ala Phe Thr Leu Lys Gln Phe Ala
1               5

<210> SEQ ID NO 86
<211> LENGTH: 9
<212> TYPE: PRT
<213> ORGANISM: Homo sapiens

<400> SEQUENCE: 86

Phe Glu His Ala His Asn Met Arg Val
1               5

```
<210> SEQ ID NO 87
<211> LENGTH: 9
<212> TYPE: PRT
<213> ORGANISM: Homo sapiens

<400> SEQUENCE: 87

Lys Gln Phe Ala Glu Met Tyr Val Ala
1               5

<210> SEQ ID NO 88
<211> LENGTH: 9
<212> TYPE: PRT
<213> ORGANISM: Homo sapiens

<400> SEQUENCE: 88

Arg Val Phe Ser Gly Leu Val Ser Thr
1               5

<210> SEQ ID NO 89
<211> LENGTH: 9
<212> TYPE: PRT
<213> ORGANISM: Homo sapiens

<400> SEQUENCE: 89

Arg Ile Val Glu Asn Val Asn Val Ile
1               5

<210> SEQ ID NO 90
<211> LENGTH: 9
<212> TYPE: PRT
<213> ORGANISM: Homo sapiens

<400> SEQUENCE: 90

Met Met Asn Lys Met Asp Arg Ala Leu
1               5

<210> SEQ ID NO 91
<211> LENGTH: 9
<212> TYPE: PRT
<213> ORGANISM: Homo sapiens

<400> SEQUENCE: 91

Glu Met Tyr Val Ala Lys Phe Ala Ala
1               5

<210> SEQ ID NO 92
<211> LENGTH: 9
<212> TYPE: PRT
<213> ORGANISM: Homo sapiens

<400> SEQUENCE: 92

Phe Ser Val Ser Pro Val Val Arg Val
1               5

<210> SEQ ID NO 93
<211> LENGTH: 9
<212> TYPE: PRT
<213> ORGANISM: Homo sapiens

<400> SEQUENCE: 93

Glu Leu Tyr Gln Thr Phe Gln Arg Ile
1               5
```

```
<210> SEQ ID NO 94
<211> LENGTH: 9
<212> TYPE: PRT
<213> ORGANISM: Homo sapiens

<400> SEQUENCE: 94

Ser Val Val Ala Gly Phe Gln Trp Ala
1               5

<210> SEQ ID NO 95
<211> LENGTH: 9
<212> TYPE: PRT
<213> ORGANISM: Homo sapiens

<400> SEQUENCE: 95

Ile Met Asn Phe Lys Lys Glu Glu Thr
1               5

<210> SEQ ID NO 96
<211> LENGTH: 9
<212> TYPE: PRT
<213> ORGANISM: Homo sapiens

<400> SEQUENCE: 96

Gly Ala Leu Val Val Val Asp Cys Val
1               5

<210> SEQ ID NO 97
<211> LENGTH: 9
<212> TYPE: PRT
<213> ORGANISM: Homo sapiens

<400> SEQUENCE: 97

Lys Val Glu Asp Met Met Lys Lys Leu
1               5

<210> SEQ ID NO 98
<211> LENGTH: 9
<212> TYPE: PRT
<213> ORGANISM: Homo sapiens

<400> SEQUENCE: 98

Arg Asn Met Ser Val Ile Ala His Val
1               5

<210> SEQ ID NO 99
<211> LENGTH: 9
<212> TYPE: PRT
<213> ORGANISM: Homo sapiens

<400> SEQUENCE: 99

Lys Ala Asn Ile Arg Asn Met Ser Val
1               5

<210> SEQ ID NO 100
<211> LENGTH: 9
<212> TYPE: PRT
<213> ORGANISM: Homo sapiens

<400> SEQUENCE: 100

Thr Val Ser Glu Glu Ser Asn Val Leu
1               5

<210> SEQ ID NO 101
<211> LENGTH: 9
```

<212> TYPE: PRT
<213> ORGANISM: Homo sapiens

<400> SEQUENCE: 101

Gly Val Cys Val Gln Thr Glu Thr Val
1               5

<210> SEQ ID NO 102
<211> LENGTH: 9
<212> TYPE: PRT
<213> ORGANISM: Homo sapiens

<400> SEQUENCE: 102

Asp Ile Thr Lys Gly Val Gln Tyr Leu
1               5

<210> SEQ ID NO 103
<211> LENGTH: 9
<212> TYPE: PRT
<213> ORGANISM: Homo sapiens

<400> SEQUENCE: 103

Ala Val Met Arg Arg Trp Leu Pro Ala
1               5

<210> SEQ ID NO 104
<211> LENGTH: 9
<212> TYPE: PRT
<213> ORGANISM: Homo sapiens

<400> SEQUENCE: 104

Phe Ser Ser Glu Val Thr Ala Ala Leu
1               5

<210> SEQ ID NO 105
<211> LENGTH: 9
<212> TYPE: PRT
<213> ORGANISM: Homo sapiens

<400> SEQUENCE: 105

Lys Leu Trp Gly Asp Arg Tyr Phe Asp
1               5

<210> SEQ ID NO 106
<211> LENGTH: 9
<212> TYPE: PRT
<213> ORGANISM: Homo sapiens

<400> SEQUENCE: 106

Leu Glu Pro Glu Glu Leu Tyr Gln Thr
1               5

<210> SEQ ID NO 107
<211> LENGTH: 9
<212> TYPE: PRT
<213> ORGANISM: Homo sapiens

<400> SEQUENCE: 107

Gly Val Asp Gln Phe Leu Val Lys Thr
1               5

<210> SEQ ID NO 108
<211> LENGTH: 9
<212> TYPE: PRT
<213> ORGANISM: Homo sapiens

<400> SEQUENCE: 108

Phe Thr Leu Lys Gln Phe Ala Glu Met
1               5

<210> SEQ ID NO 109
<211> LENGTH: 9
<212> TYPE: PRT
<213> ORGANISM: Homo sapiens

<400> SEQUENCE: 109

Ala Glu Met Tyr Val Ala Lys Phe Ala
1               5

<210> SEQ ID NO 110
<211> LENGTH: 9
<212> TYPE: PRT
<213> ORGANISM: Homo sapiens

<400> SEQUENCE: 110

Phe Thr Ala Asp Leu Arg Ser Asn Thr
1               5

<210> SEQ ID NO 111
<211> LENGTH: 9
<212> TYPE: PRT
<213> ORGANISM: Homo sapiens

<400> SEQUENCE: 111

Met Ile Asp Pro Val Leu Gly Thr Val
1               5

<210> SEQ ID NO 112
<211> LENGTH: 9
<212> TYPE: PRT
<213> ORGANISM: Homo sapiens

<400> SEQUENCE: 112

Tyr Leu Pro Val Asn Glu Ser Phe Gly
1               5

<210> SEQ ID NO 113
<211> LENGTH: 9
<212> TYPE: PRT
<213> ORGANISM: Homo sapiens

<400> SEQUENCE: 113

Asn Pro Ala Asp Leu Pro Lys Leu Val
1               5

<210> SEQ ID NO 114
<211> LENGTH: 9
<212> TYPE: PRT
<213> ORGANISM: Homo sapiens

<400> SEQUENCE: 114

Gly Pro Ala Glu Arg Ala Lys Lys Val
1               5

<210> SEQ ID NO 115
<211> LENGTH: 9
<212> TYPE: PRT
<213> ORGANISM: Homo sapiens

<400> SEQUENCE: 115

Asp Leu Pro Lys Leu Val Glu Gly Leu
1               5

<210> SEQ ID NO 116
<211> LENGTH: 9
<212> TYPE: PRT
<213> ORGANISM: Homo sapiens

<400> SEQUENCE: 116

Met Val Asn Phe Thr Val Asp Gln Ile
1               5

<210> SEQ ID NO 117
<211> LENGTH: 9
<212> TYPE: PRT
<213> ORGANISM: Homo sapiens

<400> SEQUENCE: 117

Gly Gly Gln Ala Phe Pro Gln Cys Val
1               5

<210> SEQ ID NO 118
<211> LENGTH: 9
<212> TYPE: PRT
<213> ORGANISM: Homo sapiens

<400> SEQUENCE: 118

Val Leu Thr Ala Gln Pro Arg Leu Met
1               5

<210> SEQ ID NO 119
<211> LENGTH: 9
<212> TYPE: PRT
<213> ORGANISM: Homo sapiens

<400> SEQUENCE: 119

Ser Gly Leu His Gly Trp Ala Phe Thr
1               5

<210> SEQ ID NO 120
<211> LENGTH: 9
<212> TYPE: PRT
<213> ORGANISM: Homo sapiens

<400> SEQUENCE: 120

Ile Thr Ile His Leu Pro Ser Pro Val
1               5

<210> SEQ ID NO 121
<211> LENGTH: 9
<212> TYPE: PRT
<213> ORGANISM: Homo sapiens

<400> SEQUENCE: 121

Lys Ser Thr Leu Thr Asp Ser Leu Val
1               5

<210> SEQ ID NO 122
<211> LENGTH: 9
<212> TYPE: PRT
<213> ORGANISM: Homo sapiens

<400> SEQUENCE: 122

Gly Glu Leu His Leu Glu Ile Cys Leu

```
1               5

<210> SEQ ID NO 123
<211> LENGTH: 9
<212> TYPE: PRT
<213> ORGANISM: Homo sapiens

<400> SEQUENCE: 123

Cys Ile Thr Ile Lys Ser Thr Ala Ile
1               5

<210> SEQ ID NO 124
<211> LENGTH: 9
<212> TYPE: PRT
<213> ORGANISM: Homo sapiens

<400> SEQUENCE: 124

Ser Glu Val Thr Ala Ala Leu Arg Val
1               5

<210> SEQ ID NO 125
<211> LENGTH: 9
<212> TYPE: PRT
<213> ORGANISM: Homo sapiens

<400> SEQUENCE: 125

Phe Thr Val Asp Gln Ile Arg Ala Ile
1               5

<210> SEQ ID NO 126
<211> LENGTH: 9
<212> TYPE: PRT
<213> ORGANISM: Homo sapiens

<400> SEQUENCE: 126

Ala Gln Pro Arg Leu Met Glu Pro Ile
1               5

<210> SEQ ID NO 127
<211> LENGTH: 9
<212> TYPE: PRT
<213> ORGANISM: Homo sapiens

<400> SEQUENCE: 127

Tyr Leu Ala Glu Lys Tyr Glu Trp Asp
1               5

<210> SEQ ID NO 128
<211> LENGTH: 9
<212> TYPE: PRT
<213> ORGANISM: Homo sapiens

<400> SEQUENCE: 128

Lys Ile Trp Cys Phe Gly Pro Asp Gly
1               5

<210> SEQ ID NO 129
<211> LENGTH: 9
<212> TYPE: PRT
<213> ORGANISM: Homo sapiens

<400> SEQUENCE: 129

Gly Thr Val Gly Phe Gly Ser Gly Leu
1               5
```

```
<210> SEQ ID NO 130
<211> LENGTH: 9
<212> TYPE: PRT
<213> ORGANISM: Homo sapiens

<400> SEQUENCE: 130

Val Glu Ile Gln Cys Pro Glu Gln Val
1               5

<210> SEQ ID NO 131
<211> LENGTH: 9
<212> TYPE: PRT
<213> ORGANISM: Homo sapiens

<400> SEQUENCE: 131

Lys Asn Pro Ala Asp Leu Pro Lys Leu
1               5

<210> SEQ ID NO 132
<211> LENGTH: 9
<212> TYPE: PRT
<213> ORGANISM: Homo sapiens

<400> SEQUENCE: 132

Gly Val Arg Phe Asp Val His Asp Val
1               5

<210> SEQ ID NO 133
<211> LENGTH: 9
<212> TYPE: PRT
<213> ORGANISM: Homo sapiens

<400> SEQUENCE: 133

Thr Thr Phe Glu His Ala His Asn Met
1               5

<210> SEQ ID NO 134
<211> LENGTH: 9
<212> TYPE: PRT
<213> ORGANISM: Homo sapiens

<400> SEQUENCE: 134

Gly Asn Ile Val Gly Leu Val Gly Val
1               5

<210> SEQ ID NO 135
<211> LENGTH: 9
<212> TYPE: PRT
<213> ORGANISM: Homo sapiens

<400> SEQUENCE: 135

Ile Ile Pro Thr Ala Arg Arg Cys Leu
1               5

<210> SEQ ID NO 136
<211> LENGTH: 9
<212> TYPE: PRT
<213> ORGANISM: Homo sapiens

<400> SEQUENCE: 136

Pro Leu Met Met Tyr Ile Ser Lys Met
1               5

<210> SEQ ID NO 137
```

```
<211> LENGTH: 9
<212> TYPE: PRT
<213> ORGANISM: Homo sapiens

<400> SEQUENCE: 137

Gly Gln Leu Gly Pro Ala Glu Arg Ala
1               5

<210> SEQ ID NO 138
<211> LENGTH: 9
<212> TYPE: PRT
<213> ORGANISM: Homo sapiens

<400> SEQUENCE: 138

Leu Lys Gln Phe Ala Glu Met Tyr Val
1               5

<210> SEQ ID NO 139
<211> LENGTH: 9
<212> TYPE: PRT
<213> ORGANISM: Homo sapiens

<400> SEQUENCE: 139

Met Gly Asn Ile Met Ile Asp Pro Val
1               5

<210> SEQ ID NO 140
<211> LENGTH: 9
<212> TYPE: PRT
<213> ORGANISM: Homo sapiens

<400> SEQUENCE: 140

Lys Val Phe Asp Ala Ile Met Asn Phe
1               5

<210> SEQ ID NO 141
<211> LENGTH: 9
<212> TYPE: PRT
<213> ORGANISM: Homo sapiens

<400> SEQUENCE: 141

Met Glu Pro Ile Tyr Leu Val Glu Ile
1               5
```